United States Patent
Strano et al.

(10) Patent No.: US 12,055,493 B2
(45) Date of Patent: Aug. 6, 2024

(54) FLUORESCENCE-BASED DETECTION OF PROTEIN AGGREGATION AND FIBER OPTIC-BASED BENCHTOP INSTRUMENT

(71) Applicant: MASSACHUSETTS INSTITUTE OF TECHNOLOGY, Cambridge, MA (US)

(72) Inventors: Michael Strano, Lexington, MA (US); Daichi Kozawa, Cambridge, MA (US); Xun Gong, Boston, MA (US); Daniel Salem, Liverpool, NY (US); Sooyeon Cho, Cambridge, MA (US); Freddy T. Nguyen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/991,013

(22) Filed: Aug. 11, 2020

(65) Prior Publication Data
US 2021/0048392 A1    Feb. 18, 2021

Related U.S. Application Data

(60) Provisional application No. 62/885,529, filed on Aug. 12, 2019.

(51) Int. Cl.
*G01N 21/64* (2006.01)
*G01N 33/68* (2006.01)

(52) U.S. Cl.
CPC ..... *G01N 21/6486* (2013.01); *G01N 33/6809* (2013.01); *G01N 2021/6484* (2013.01)

(58) Field of Classification Search
CPC ....... G01N 21/6486; G01N 2021/6484; G02N 33/6809
See application file for complete search history.

(56) References Cited

U.S. PATENT DOCUMENTS

| | | | | |
|---|---|---|---|---|
| 4,943,364 A | * | 7/1990 | Koch | G01N 21/7703 204/415 |
| 10,024,797 B2 | * | 7/2018 | Reardon | C12Q 1/005 |
| 2004/0064018 A1 | * | 4/2004 | Dunki-Jacobs | A61B 1/07 600/178 |
| 2004/0211271 A1 | * | 10/2004 | Han | G01Q 70/12 73/866.5 |
| 2005/0043894 A1 | * | 2/2005 | Fernandez | A61B 5/686 128/920 |
| 2005/0069572 A1 | * | 3/2005 | Williams | A61L 27/3895 424/426 |
| 2006/0231399 A1 | * | 10/2006 | Smalley | G01N 21/6428 204/450 |
| 2007/0147738 A1 | * | 6/2007 | Wang | G01N 21/45 385/12 |
| 2008/0116361 A1 | * | 5/2008 | Sanders | G01D 5/35345 250/227.18 |

(Continued)

OTHER PUBLICATIONS

Helmchen, F., "Miniaturization of fluorescence microscopes using fibre optics", Experimental Physiology 87.6, 737-745 (Year: 2002).*

(Continued)

*Primary Examiner* — Blake C Riddick
(74) *Attorney, Agent, or Firm* — Honigman LLP

(57) ABSTRACT

A sensor can include a nanostructure in a housing configured to contact a sample.

15 Claims, 57 Drawing Sheets

(56) References Cited

U.S. PATENT DOCUMENTS

| | | | |
|---|---|---|---|
| 2008/0171383 A1* | 7/2008 | Selker | C12M 41/32 435/288.7 |
| 2008/0205833 A1* | 8/2008 | Fu | A61B 5/0062 385/117 |
| 2009/0140167 A1* | 6/2009 | Ward | G01N 21/65 250/458.1 |
| 2011/0053270 A1* | 3/2011 | Chang | G03F 7/095 435/402 |
| 2011/0212440 A1* | 9/2011 | Viovy | G01N 33/5008 435/6.1 |
| 2011/0226962 A1* | 9/2011 | Boudreau | G02B 21/16 250/459.1 |
| 2012/0100631 A1* | 4/2012 | Dillmore | G01N 33/92 436/501 |
| 2013/0035567 A1* | 2/2013 | Strano | A61B 5/14532 600/316 |
| 2013/0156697 A1* | 6/2013 | Vitaliano | B82Y 5/00 424/1.69 |
| 2014/0234856 A1* | 8/2014 | Reuel | G01N 33/5436 435/7.1 |
| 2014/0332407 A1* | 11/2014 | Mai | G01N 33/5438 205/777.5 |
| 2014/0363808 A1* | 12/2014 | Gu | G01N 33/57488 435/5 |
| 2015/0133752 A1* | 5/2015 | Iverson | B82Y 15/00 600/316 |
| 2015/0147756 A1* | 5/2015 | Vollmer | C12Q 1/6825 435/287.2 |
| 2016/0097764 A1* | 4/2016 | Taslim | G01N 33/5308 422/82.01 |
| 2016/0266105 A1* | 9/2016 | Ismagilov | B01L 3/502715 |
| 2018/0136163 A1* | 5/2018 | Chang | G01N 27/127 |
| 2019/0079068 A1* | 3/2019 | Taslim | C01B 32/194 |
| 2019/0170739 A1* | 6/2019 | Garner | C12Q 1/006 |
| 2019/0358387 A1* | 11/2019 | Elbadry | A61M 1/3663 |

OTHER PUBLICATIONS

International Search Report issued Nov. 20, 2020 in corresponding International Patent Application No. PCT/US2020/045827.

Written Opinion of the International Search Authority issued Nov. 20, 2020 in corresponding International Patent Application No. PCT/US2020/045827.

* cited by examiner

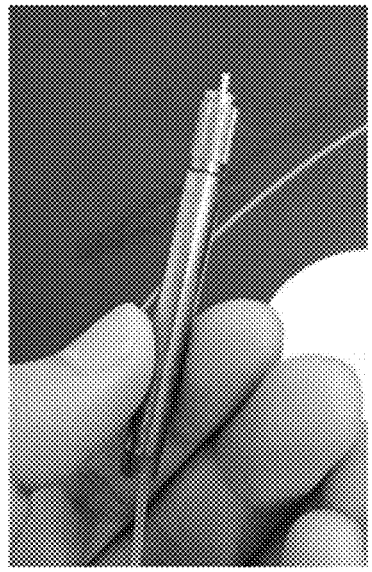 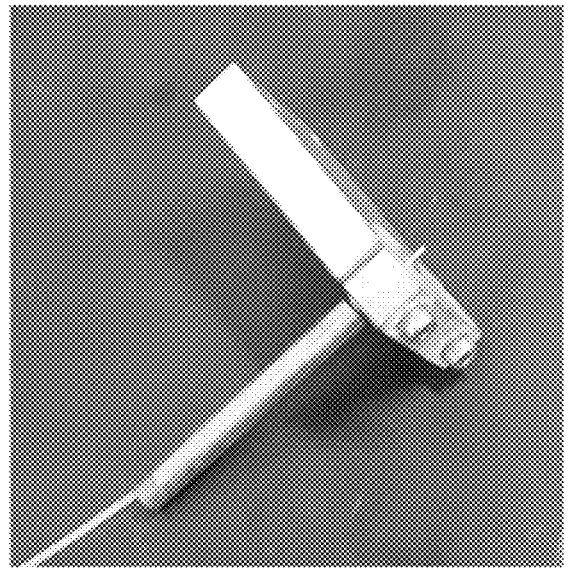
FIG. 26A    FIG. 26B
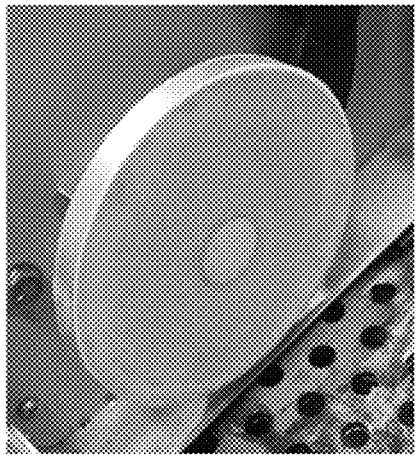 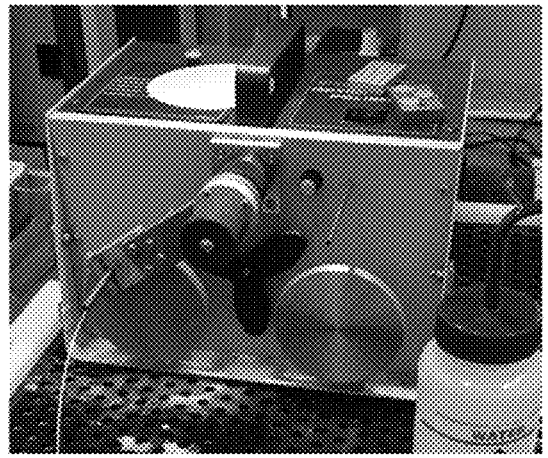
FIG. 26C    FIG. 26D

Fiber Optic Probe Tip Interface to Hydrogel

Excitation Fiber (Center)

Fluorescence Collection
Fiber Bundle
(Outer Ring)

FLUORESCENCE-BASED DETECTION OF PROTEIN AGGREGATION AND FIBER OPTIC-BASED BENCHTOP INSTRUMENT

CLAIM OF PRIORITY

This applications claims priority to U.S. Provisional Patent Application No. 62/885,529, filed Aug. 12, 2019, which is incorporated by reference in its entirety.

TECHNICAL FIELD

This invention relates to a nanotube array for optical detection of protein-protein interactions.

BACKGROUND

The biopharmaceutical industry faces several challenges during drug discovery, manufacturing, and scaling processes to produce high quality, reproducible, and effective drugs. New techniques are needed to provide the pharmaceutical industry with the real-time analytical tools needed to accomplish these goals. During the drug manufacturing process, there is an increased need from both a safety and regulatory point of view to ensure the high quality and purity of samples throughout the process and to rapidly discern monomers from aggregates such as dimers, trimers, and polymers of the drug. Protein aggregation in manufacturing poses an enormous challenge as it can decrease the efficacy of the formulations, decrease the product yield, and potentially introduce immunogenicity.

SUMMARY

Hydrogel-encapsulated, label-free fluorescent nanosensors can be used for the characterization of protein aggregation. For example, the nanosensors can detect the presence of high molecular weight protein species at a concentration as low as one percent. In addition, an apparatus for signal detection, for example, a fiber optic-based benchtop instrument that interfaces with the hydrogels described herein. The instrument allows for a small form factor that is portable and can easily be integrated into different areas of research, for example, a biopharmaceutical synthesis processes.

In one aspect, a sensor can include a housing including a chamber, a light port and a sample contact port, and a sensor composition including a nanostructure, the nanostructure configured to interact with a protein, the composition being in contact with the light port and a sample contact surface adjacent to the sample contact port.

In another aspect, a method for detecting a protein aggregate can include providing the sensor as described herein, exposing the sensor to a sample, monitoring a property of the composition, and determining the presence of protein aggregate in the sample based on the monitored property.

In another aspect, a sensor device includes a housing including a chamber, a light port and a sample contact port; and a fiber optic including an excitation fiber configured to provide an excitation wavelength and a detection fiber configured to detect an emission wavelength. The chamber is configured to contain a sensor composition described herein.

In certain circumstances, the nanostructure can be supported in or on a first hydrogel.

In certain circumstances, the nanostructure can be in or on a solid.

In certain circumstances, the nanostructure can be in a liquid within the chamber.

In certain circumstances, the nanostructure can be supported on the first hydrogel.

In certain circumstances, the sensor can include a second hydrogel between the first hydrogel and the sample contact port.

In certain circumstances, the second hydrogel can have a predetermined thickness.

In certain circumstances, the first hydrogel can be a polymeric hydrogel, for example, agarose or other organic hydrogel material.

In certain circumstances, the second hydrogel can be the same material as the first hydrogel.

In certain circumstances, the nanostructure can include a linker associated with the nanostructure, wherein the linker is configured to interact with a capture protein.

In certain circumstances, the nanostructure can be a photoluminescent carbon nanotube.

In certain circumstances, the linker can include a polymer, for example, a polypeptide, a polynucleotide or a polysaccharide.

In certain circumstances, the polysaccharide can be chitosan.

In certain circumstances, the light port can be configured to attach to a fiber optic.

In certain circumstances, the fiber optic can include an excitation fiber configured to provide an excitation wavelength to the nanostructure. The fiber optic can provide a fiber based excitation-emission system for fluorescence detection. The nanostructure can be nanoparticles in any situation: gel, liquid, dried, coated, or aerosolized.

In certain circumstances, the fiber optic can include a detection fiber configured to detect an emission wavelength from the nanostructure. The fiber optic can include an optical source, for example, a laser or light emitting diode. The fiber optic also can include a detector, for example, a single channel detector or a spectrophotometer.

Other features or advantages will be apparent from the following detailed description of several embodiments, and also from the appended claims.

BRIEF DESCRIPTION OF THE DRAWINGS

FIG. 2A depicts a picture of hydrogel sensors held in 96-well plate under 532 nm-excitation through the fiber optic. FIG. 2B depicts a schematic of sensor configurations without an extra agarose hydrogel layer on SWCNT sensors. FIG. 2C depicts purified (6,5) chirality SWCNT (CHASM) and FIG. 2D depicts HiPCO loading protein A showing sensor responses to 10 mg/mL unstressed human $IgG_1$ without the tunable layer.

FIG. 5A shows a schematic of nIR fluorescent sensor detection mechanism. FIG. 5B shows a custom-built instrument used for performing inverted fluorescence excitation with a high-powered LED (880 mW) at 565 nm and collecting fluorescence from the underside of a standard 96 well plate into which the sensor and hydrogel are cast for each well; LP and SP denote long-pass and short-pass, respectively. FIG. 5C shows experimental design to detect protein aggregation where a tunable hydrogel layer influences diffusion of analyte to the sensors. Normalized nIR fluorescence sensor response, $R/R_{max}$, to (FIG. 5D) 10 mg/ml human IgG$_1$ in PBS and (FIG. 5E) 10 mM EDTA in PBS with (blue) and without (red) an extra hydrogel layer of 0.2% agarose.

(FIG. 11D) Fitted L$_1$ and L$_2$ values for each dataset obtained by specifying the composition from the SE-UPLC data. Error bars represent the standard deviation from four replicates. (FIG. 11E) Fitted mole fractions of monomer, LMW, and HMW species using the L$_1$ and L$_2$ values fitted to the unstressed data. Error bars represent the 95% confidence intervals.

FIG. 18A depicts schematics and photo-images of the optode fiber configurations with commercial. FIG. 18B depicts optical microscope images of probe fiber tips with excitation and fluorescence collection components (inset: sapphire half ball lens included with custom-built variants). FIG. 18C depicts fluorescence collection performance comparison between commercial and custom-built optode fibers.

FIG. 19A depicts UV-vis-nIR absorbance spectrum of chitosan-wrapped SWNT nanosensors (inset: photo-image of the nanosensor dispersion). FIG. 19B depicts hydrogel signal modulation with and without SWNT sensor encapsulation following protein A and unstressed human antibody IgG injections.

FIG. 20A depicts schematics of IgG aggregation behavior with UV exposure of 3, 7, and 74 hr. FIG. 20B depicts schematics of the SWNT/hydrogel sensing system described by a multi-layer diffusion model with two different hydrogel thickness $L_1$ and $L_2$. FIG. 20C depicts statistics of model extracted mole fraction of monomer ($\alpha$MP) and dimer ($\alpha$HMW) IgG. The error bars are standard deviations of experiments with triplicated sensor synthesis.

FIG. 21A depicts a CAD of sensor tip. FIG. 21B depicts a real-time sensor response and model fitting of a sensor tip coupled with optode fiber to un stressed IgG (10 μL of 10 mg/mL). FIG. 21C depicts a photo-image of the SWNT/hydrogel sensing layer synthesized in large-scale (5.5 cm petri dish). FIG. 21D depicts a magnified nIR image of the large-area synthesized SWNT/hydrogel sensing layer with maximum beam size exposure. FIG. 21E depicts a multiple pre-fabricated sensing tip array for readily interfaced with optode fiber. FIG. 21F depicts a real-time fluorescence signal of fully-integrated lab-on-fiber system with varied mechanical distortions during measurement. (Scale bars: 1 cm).

FIG. 22A depicts schematics and CAD for the miniaturized sensor tip configuration for liquid phase nanosensor detection, absent the hydrogel interface. FIG. 22B depicts an image of assembled nanosensor tip with O-ring and glass slide. FIG. 22C depicts a fully-integrated sensor tip for liquid phase bioanalytes detection (inset: nIR image of sensor tip with excitation laser). Real-time lab-on-fiber monitoring of various bioanalytes (5 μL) including (FIG. 22D) serotonin (5-HT) (1 mM), (FIG. 22E) norepinephrine (NE) (1 mM), (f) epinephrine (adrenaline) (1 mM), and (FIG. 22G) hydrogen peroxide ($H_2O_2$) (10 mM). (FIG. 22H) Maximum sensor response following 2 min exposure with each analyte. (FIG. 22I) Normalized sensor response of 3D sensing tip w/ and w/o hydrogel for 1 mM serotonin. (Scale bars: 1 cm).

FIGS. 26A-26D show fiber optic probe placed inside a holding jig (FIG. 26A) and mounted inside an aluminum block (FIG. 26B). The polisher (FIGS. 26C and 26D) is used to polish the end of the fiber optic probe using from coarse grained sand paper to fine grained sand paper from 30 μm to 1 μm size.

(FIG. 27A) before the end was polished (FIG. 27B) after the 30 μm polish (FIG. 27C) after the last 1 μm polish. As the end gets more and more polished, each fiber end becomes more distinct and the light transmission is higher.

FIG. 30A depicts a photo-image of experimental setup for power-meter monitoring. FIG. 30B depicts a real-time raw and noise-corrected fluorescence data.

DETAILED DESCRIPTION

Figure 1A:
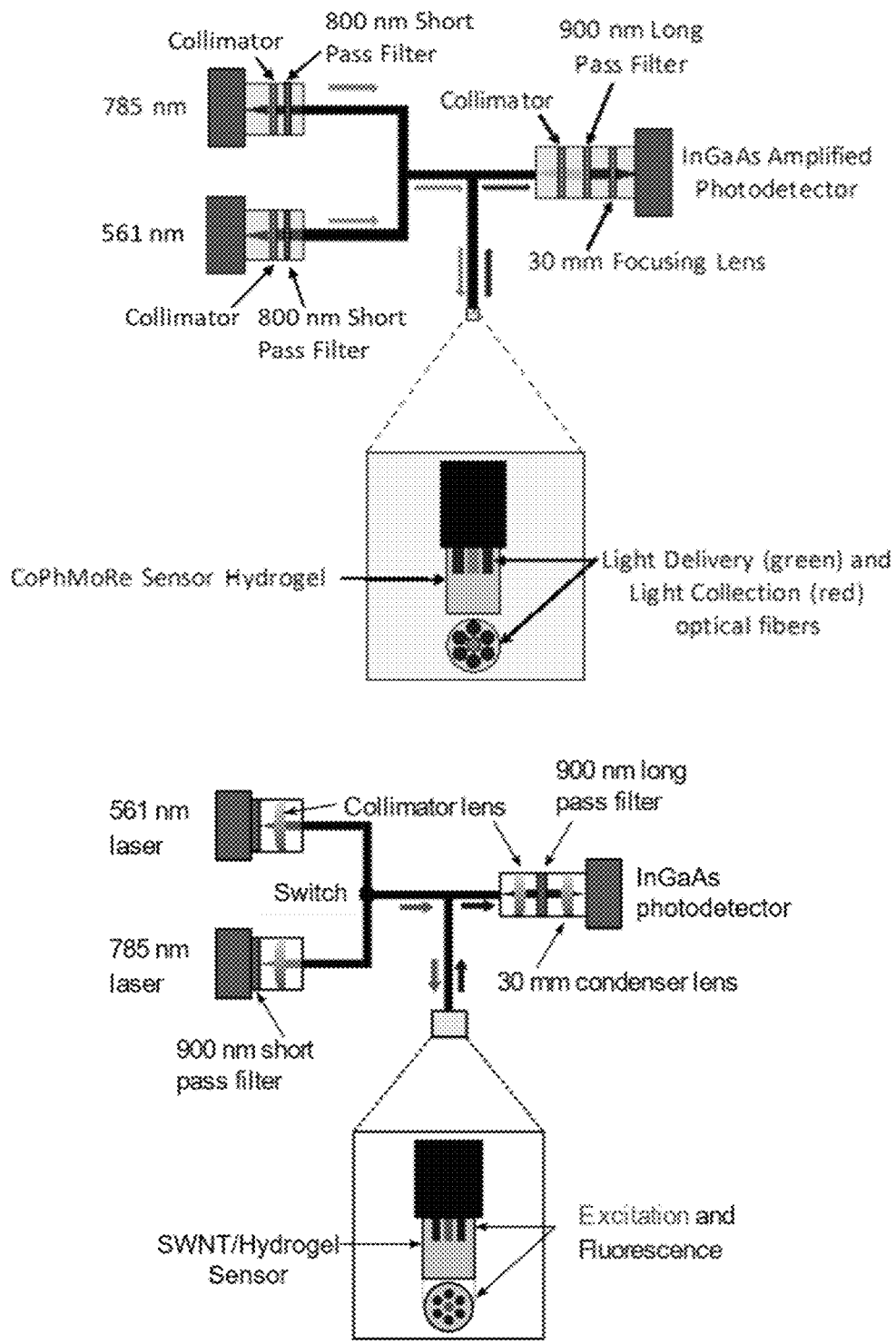
FIG. 1A depicts a fiber-based near-infrared fluorescence spectroscopy (optode) and nanosensor hydrogel combined system. 785 nm and 561 nm light were delivered via optical fibers (green) to the nanosensor hydrogel which coats the tip of the optical fibers. The outer ring of fibers (red) collects the near-infrared fluorescence signal from the sensor hydrogel. The light was collimated out of the fiber, passed through a 900 nm long pass filter to remove any excitation light, and focused onto the InGaAs amplified photodetector.

There is a high need for a low-cost, rapid, analytical tool that can identify protein aggregates to allow for the monitoring of the purity, quality, and effectiveness of biologic drugs throughout the purification and manufacturing processes. Current inline analytical technologies can be limited in their characterization ability, and traditional offline methods are time-consuming. Nanosensors, specifically label-free, selective transducers of molecular recognition, constitute an emerging technology with specific advantages for quality assurance and process control applications in the pharmaceutical industry. The sensors have been demonstrated to achieve single molecule detection, with rapid response times (minutes to seconds depending on sensor and gel configuration), and can be multiplexed. Nanosensors can also support new molecular recognition technologies such as CoPhMoRe (Corona Phase Molecular Recognition), that generates synthetic, non-biological recognition sites.

Label-free nanosensors described herein can rapidly characterize protein samples for the presence of aggregates. The approach to developing the nanosensors uses several strategies to design selective molecular sensors using near-infrared (NR) fluorescent single-walled carbon nanotubes (SWNTs). Upon molecular recognition and analyte binding, the SWNT fluorescence signal is modulated and optically measured via an IR detector. The rapid optical readout and long-term fluorescence stability of the SWNT sensors allow for scaling of the label-free technology for a high degree of multiplexation. The ability to collect dynamic real-time binding data provides a significant advantage over conventional fluorescence-based detection platforms that require labeling via irreversible antibody binding and are susceptible to photobleaching.

The approach also provides for a fiber optic-based system that interfaces with the hydrogels described herein. This allows for a small form factor that is portable and can easily be integrated into different areas of the drug processing steps. This technique increases the portability and decreases the size of the ultimate form factor.

This technique is capable of characterizing drug product in several different scenarios and form factors during the processing steps. This could be applied to bioreactor fluid at-line flow-over configurations. Real-time measurements obtained from bioreactor fluid will allow for the implementation of feedback control techniques in the biopharmaceutical industry.

The monitoring of biopharmaceutical critical quality attributes (CQAs) in-process, at both the process development and manufacturing stages, can be necessary for the implementation of process analytical technology (PAT) and quality-by-design (QbD) principles. Macromolecular therapeutics are much more challenging to characterize than traditional small molecule drugs, as each analytical technique deployed provides a limited snapshot of the molecule's physical/chemical structure and function. In addition, there remains limited first-principles understanding of the complex bioprocesses taking place during biopharmaceutical manufacturing, including how critical process parameters ultimately influence properties of the final product. Over the last twenty years, a great deal of research effort has focused on transitioning biopharmaceutical manufacturing processes from batch-based to continuous. This shift has the potential to significantly reduce the footprint of manufacturing facilities while enabling a more modular process design that provides more flexibility for manufacturers. However, realization of continuous manufacturing, in addition to real-time release, requires rapid analytical technologies that can enable the implementation of process control strategies and evaluate the quality of the produced drug on-line, in-line, or at-line. Here, the development of a novel nanosensor platform consisting of hydrogel-encapsulated near-infrared (nIR)-fluorescent nanoparticles for the rapid (<20 minutes) characterization of protein aggregation is reported. This tunable hydrogel influences the diffusion of analyte to the sensors, allowing us to identify the presence of aggregate species through changes in the sensor response dynamics. See, for example, Undey, C., Ertunc, S., Mistretta, T. & Looze, B. Applied advanced process analytics in biopharmaceutical manufacturing: Challenges and prospects in real-time monitoring and control. *J Process Contr* 20, 1009-1018, (2010); Guidance for industry: PAT—a framework for innovative pharmaceutical development, manufacturing and quality assurance. (Food and Drug Administration, 2004); Glassey, J. et al. Process analytical technology (PAT) for biopharmaceuticals. *Biotechnol J* 6, 369-377, (2011); Rathore, A. S., Bhambure, R. & Ghare, V. Process analytical technology (PAT) for biopharmaceutical products. *Anal Bioanal Chem* 398, 137-154, (2010); Berkowitz, S. A., Engen, J. R., Mazzeo, J. R. & Jones, G. B. Analytical tools for characterizing biopharmaceuticals and the implications for biosimilars. *Nat Rev Drug Discov* 11, 527-540; Croughan, M. S., Konstantinov, K. B. & Cooney, C. The Future of Industrial Bioprocessing: Batch or Continuous? *Biotechnol Bioeng* 112, 648-651, (2015); Warikoo, V. et al. Integrated continuous production of recombinant therapeutic proteins. *Biotechnol Bioeng* 109, 3018-3029, doi:10.1002/bit.24584 (2012); Crowell, L. E. et al. On-demand manufacturing of clinical-quality biopharmaceuticals. *Nat Biotechnol* 36, 988-+, doi:10.1038/nbt.4262 (2018); and Hong, M. S. et al. Challenges and opportunities in biopharmaceutical manufacturing control. *Comput Chem Eng* 110, 106-114, (2018), each of which is incorporated by reference in its entirety.

The aggregation state of protein therapeutics is a CQA that must be monitored and controlled throughout the manufacturing process as well as during storage. Proteins exhibit limited stability in solution and can undergo aggregation in response to various stressors including temperature, light, shear, and changes in solution conditions (e.g., ionic strength, pH). In addition to influencing the viscosity of the protein formulation, protein aggregates may induce immunogenic responses upon administration in patients and negatively impact drug deliverability. As a result, the concentration of microscopically visible and sub-visible particles must be carefully monitored, and protein formulations must be designed to limit the extent of protein aggregation when properly stored. See, for example, Joubert, M. K., Luo, Q. Z., Nashed-Samuel, Y., Wypych, J. & Narhi, L. O. Classification and Characterization of Therapeutic Antibody Aggregates. *J Biol Chem* 286, 25118-25133, (2011); Roberts, C. J. Therapeutic protein aggregation: mechanisms, design, and control. *Trends Biotechnol* 32, 372-380, (2014); Wang, W. Protein aggregation and its inhibition in biopharmaceutics. *Int J Pharmaceut* 289, 1-30, (2005); Luo, Q. Z. et al. Chemical Modifications in Therapeutic Protein Aggregates Generated under Different Stress Conditions. *J Biol Chem* 286, 25134-25144 (2011); Mahler, H. C., Friess, W., Grauschopf, U. & Kiese, S. Protein Aggregation: Pathways, Induction Factors and Analysis. *J Pharm Sci-Us* 98, 2909-2934 (2009); Hawe, A., Kasper, J. C., Friess, W. & Jiskoot, W. Structural properties of monoclonal antibody aggregates induced by freeze-thawing and thermal stress. *Eur J Pharm Sci* 38, 79-87 (2009); Amin, S., Barnett, G. V., Pathak, J. A., Roberts, C. J. & Sarangapani, P. S. Protein aggregation, particle formation, characterization & rheology. *Curr Opin Colloid In* 19, 438-449, (2014); Pathak, J. A., Sologuren, R. R. & Narwal, R. Do Clustering Monoclonal Antibody Solutions Really Have a Concentration Dependence of Viscosity? *Biophys J* 104, 913-923, (2013); Rosenberg, A. S.

Effects of protein aggregates: An immunologic perspective. *Aaps J* 8, E501-E507 (2006); Demeule, B., Gumy, R. & Arvinte, T. Where disease pathogenesis meets protein formulation: Renal deposition of immunoglobulin aggregates. *Eur J Pharm Biopharm* 62, 121-130, (2006); and Ripple, D. C. & Dimitrova, M. N. Protein particles: What we know and what we do not know. *J Pharm Sci-Us* 101, 3568-3579, doi:10.1002/jps.23242 (2012), each of which is incorporated by reference in its entirety.

Proteins can undergo aggregation via a series of different reaction mechanisms, which ultimately determine the size and shape of the resulting particles. The reaction mechanism that dominates within a particular system is influenced by the protein itself as well as the stressors at play. In general, physical aggregation involves a series of reversible and irreversible steps that include the unfolding of protein regions and the formation of non-covalent protein bonds via the interaction of hydrophobic sections of amino acids. The resulting size distribution is a product of competing reactions ranging from monomer-monomer nucleation to aggregate-aggregate coalescence, where aggregate particles can range from 10 nm to greater than 10 μm. See, for example, Roberts, C. J. Therapeutic protein aggregation: mechanisms, design, and control. *Trends Biotechnol* 32, 372-380, (2014); Wang, W. Protein aggregation and its inhibition in biopharmaceutics. *Int J Pharmaceut* 289, 1-30, (2005); Hawe, A., Kasper, J. C., Friess, W. & Jiskoot, W. Structural properties of monoclonal antibody aggregates induced by freeze-thawing and thermal stress. *Eur J Pharm Sci* 38, 79-87, (2009); and Amin, S., Barnett, G. V., Pathak, J. A., Roberts, C. J. & Sarangapani, P. S. Protein aggregation, particle formation, characterization & rheology. *Curr Opin Colloid In* 19, 438-449, (2014), each of which is incorporated by reference in its entirety.

There are many analytical techniques used to characterize protein aggregation with differing levels of complexity and assay time including size-exclusion chromatography, capillary electrophoresis, and dynamic light scattering. These techniques vary in the amount and resolution of structural and size information that they provide, with no single analytical technique being capable of fully elucidating the protein size distribution. Nevertheless, there remains a need for new analytical technologies capable of rapid and/or continuous monitoring of protein aggregation for deployment within the biopharmaceutical manufacturing process in-line, on-line, or at-line. Such technologies would assist in the understanding and development of new bioprocesses, in addition to enabling feedback process control techniques to be implemented at the manufacturing level. See, for example, den Engelsman, J. et al. Strategies for the Assessment of Protein Aggregates in Pharmaceutical Biotech Product Development. *Pharm Res-Dordr* 28, 920-933, (2011); Hong, P., Koza, S. & Bouvier, E. S. P. A Review Size-Exclusion Chromatography for the Analysis of Protein Biotherapeutics and Their Aggregates. *J Liq Chromatogr R T* 35, 2923-2950, (2012); Fekete, S., Beck, A., Veuthey, J. L. & Guillarme, D. Theory and practice of size exclusion chromatography for the analysis of protein aggregates. *J Pharmaceut Biomed* 101, 161-173, (2014); Bermudez, O. & Forciniti, D. Aggregation and denaturation of antibodies: a capillary electrophoresis, dynamic light scattering, and aqueous two-phase partitioning study. *J Chromatogr B* 807, 17-24, (2004); Righetti, P. G. & Verzola, B. Folding/unfolding/refolding of proteins: Present methodologies in comparison with capillary zone electrophoresis. *Electrophoresis* 22, 2359-2374, (2001); Rosenqvist, E., Jossang, T. & Feder, J. Thermal-Properties of Human-Igg. *Mol Immunol* 24, 495-501, (1987); Jossang, T., Feder, J. & Rosenqvist, E. Heat Aggregation Kinetics of Human-Igg. *J Chem Phys* 82, 574-589, (1985); and Zolls, S. et al. Particles in therapeutic protein formulations, Part 1: Overview of analytical methods. *J Pharm Sci-Us* 101, 914-935, (2012), each of which is incorporated by reference in its entirety.

Single-walled carbon nanotube (SWCNT)-based optical sensors can present a promising approach towards rapid, label-free biopharmaceutical characterization and have been developed for glycoprotein characterization, biomarker detection, and characterization of protein binding interactions. Their optical readout is well-suited for sensor multiplexing, which was recently demonstrated by our group in which nanosensor arrays were fabricated and characterized for protein detection. Moreover, SWCNT nIR fluorescence does not photobleach over time, enabling the deployment of reversible sensors within continuous processes. Previously, the detection of human immunoglobulin G (IgG) using protein A-functionalized sensors embedded in a hydrogel matrix has been reported. Protein A-IgG binding deviates from a simple monovalent kinetic model due to the multivalency of the binding interaction, resulting in an effective dissociation constant, $K_{D,eff}$, which varies with protein concentration. Moreover, a bivalent binding model was formulated that could describe this phenomenon while comparing this result with the 1:1 binding observed between recombinant human growth hormone and its receptor. See, for example, Reuel, N. F. et al. Transduction of Glycan-Lectin Binding Using Near-Infrared Fluorescent Single-Walled Carbon Nanotubes for Glycan Profiling. *J Am Chem Soc* 133, 17923-17933, (2011); Reuel, N. F. et al. Emergent Properties of Nanosensor Arrays: Applications for Monitoring IgG Affinity Distributions, Weakly Affined Hypermannosylation, and Colony Selection for Biomanufacturing. *Acs Nano* 7, 7472-7482, (2013); Salem, D. P., Nelson, J. T., Kim, S. & Strano, M. S. A Dynamic, Mathematical Model for Quantitative Glycoprofiling Using Label-Free Lectin Microarrays. *Acs Sensors* 1, 987-996, (2016); Zhang, J. Q. et al. A Rapid, Direct, Quantitative, and Label-Free Detector of Cardiac Biomarker Troponin T Using Near-Infrared Fluorescent Single-Walled Carbon Nanotube Sensors. *Adv Healthc Mater* 3, 412-423, (2014); Nelson, J. T. et al. Mechanism of Immobilized Protein A Binding to Immunoglobulin G on Nanosensor Array Surfaces. *Anal Chem* 87, 8186-8193, (2015); and Dong, J. Y., Salem, D. P., Sun, J. H. & Strano, M. S. Analysis of Multiplexed Nanosensor Arrays Based on Near-Infrared Fluorescent Single-Walled Carbon Nanotubes. *Acs Nano* 12, 3769-3779, (2018), each of which is incorporated by reference in its entirety.

Among these attributes, protein aggregation during the manufacturing of biological therapeutics can be important to monitor and control in order to prevent adverse immunogenic responses and minimize negative impacts on drug deliverability. In this work, we explore hydrogel-encapsulated, label-free fluorescent nanosensors for the characterization of protein aggregation. A mathematical model can be used to describe the diffusion and binding of a series of stressed pharmaceutical samples to such sensors, describing their dynamic response. For example, mathematical modeling can map the influence of hydrogel properties on separation performance given the composition of UV-stressed $IgG_1$ samples. Using this modified model, the compositions of light-stressed $IgG_1$ samples were fit to experimental data and correlated with size-exclusion chromatography (SEC) data. The results demonstrate the ability to detect the presence of high molecular weight protein species at a concentration as low as one percent. This work represents a significant step towards the development and deployment of rapid process analytical technologies for biopharmaceutical characterization.

In this work, a SWCNT-based sensor platform has been developed for the rapid detection of $IgG_1$ aggregation using protein A-functionalized sensors coupled with a tunable hydrogel matrix. Using a combination of modeling and experiment, the ability to control protein diffusion through the hydrogel matrix to the nanosensors and predict how protein diffusion is influenced by hydrogel properties has been demonstrated. Experiments were performed using human $IgG_1$ that underwent UV light stress for varying lengths of time (3 h-74 h) and were characterized using size-exclusion ultrahigh-performance liquid chromatography (SE-UPLC) and nanoparticle tracking analysis. A mathematical model was developed that is able to describe the experimental data generated from stressed $IgG_1$ samples, allowing one to extract compositional information from the sensor binding curves including the mole fraction of high molecular weight protein aggregates. Moreover, the fitted compositions correlate with the data output by SE-UPLC, enabling the detection of high molecular weight species at concentrations as low as one percent on a molar basis. This work demonstrates that SWCNT-based optical sensors are a promising emerging technology for the rapid characterization of biopharmaceutical aggregation.

Figure 3A:
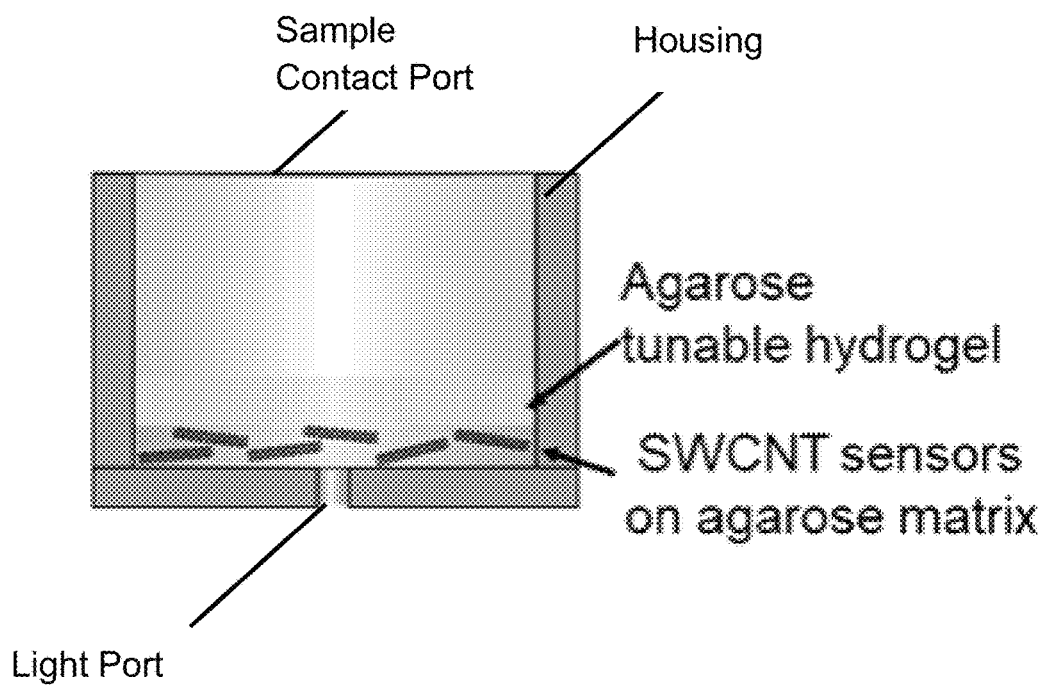
FIG. 3A depicts a schematic of sensor configurations with an extra 0.2% agarose gel layer on SWCNT sensors.

A sensor can include a housing including a chamber, a light port and a sample contact port, and a nanostructure, the nanostructure configured to interact with a protein, the hydrogel having a surface in contact with the light port and a sample contact surface adjacent to the sample contact port. See, for example, FIG. 3A, which depicts the housing, light port, and sample contact port in an exemplary sensor. The nanostructure can be supported in or on a hydrogel. Alternatively, the nanostructure can be supported in or on a solid support. In certain circumstances, the nanostructure can be in a liquid.

A method for detecting a protein aggregate can include providing the sensor as described herein, exposing the sensor to a sample, monitoring a property of the composition, and determining the presence of protein aggregate in the sample based on the monitored property.

A sensor device includes a housing including a chamber, a light port and a sample contact port; and a fiber optic including an excitation fiber configured to provide an excitation wavelength and a detection fiber configured to detect an emission wavelength. The chamber is configured to contain a sensor composition described herein. The fibers can be housed in a multi-fiber housing so that the detection fiber is proximate to the excitation fiber. The multi-fiber housing can include 1, 2, 3, 4, 5, 6, 7, or 8 excitation fibers. The multi-fiber housing can include 1, 2, 3, 4, 5, 6, 7, or 8 detection fibers. The detection fibers can encircle the excitation fiber (or excitation fibers). For example, 2, 3, 4, 5 or 6 detection fibers can surround a single excitation fiber.

In certain circumstances, the nanostructure can be supported on the first hydrogel.

In certain circumstances, the sensor can include a second hydrogel between the first hydrogel and the sample contact port.

In certain circumstances, the second hydrogel can have a predetermined thickness. The thickness can be 1 to 2,000 microns, 10 to 1000 microns, or 100 to 5000 microns.

In certain circumstances, each hydrogel can be a polymeric hydrogel. For example, each hydrogel, independently, can be agarose. The hydrogel can be any matrix that allows for diffusion of the analyte.

In certain circumstances, the second hydrogel can be the same material as the first hydrogel.

In certain circumstances, the nanostructure can include a linker associated with the nanostructure, wherein the linker is configured to interact with a capture protein, as described below.

In certain circumstances, the nanostructure can be a photoluminescent carbon nanotube or other material, described below.

In certain circumstances, the linker can include a polymer, for example, a polypeptide, a polynucleotide or a polysaccharide such as chitosan or another polymer described below.

In certain circumstances, the light port can be configured to attach to a fiber optic.

In certain circumstances, the fiber optic can include an excitation fiber configured to provide an excitation wavelength to the nanostructure. In certain circumstances, the fiber optic can include a detection fiber configured to detect an emission wavelength from the nanostructure. As shown in FIG. 1A, the excitation fiber can be the light delivery fiber and the detection fiber can be the light detection fiber shown in an exemplary sensor device.

In another aspect, a sensor device includes a housing including a chamber, a light port and a sample contact port; and a fiber optic including an excitation fiber configured to provide an excitation wavelength and a detection fiber configured to detect an emission wavelength. The chamber is configured to contain a sensor composition described herein.

A nanotube/polymer microarray can be capable of optically reporting the binding of an analyte to a tagged capture protein docked to a metal ion complex interacting with the nanotube and polymer. This microarray arrangement can enable the resolution of single protein binding events, which is the lowest detection limit of any protein array demonstrated to date. A nanotube can detect the stochastic fluctuations of single quenching molecules that adsorb or desorb in real time, which can allow the measurement of both forward and reverse binding rate constants, the ratio of which can be the inverse equilibrium or affinity constant.

A sensor composition can include a nanostructure and a linker. A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor.

A nanostructure can be a photoluminescent nanostructure, which can exhibit photoluminescence. See, for example, U.S. Pat. No. 10,215,752, which is incorporated by reference in its entirety. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semi-conductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. A property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

A linker can include a polymer. A polymer can include a polypeptide, a polynucleotide or a polysaccharide. A polysaccharide can include chitosan. A polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 g/cm$^2$, less than 1 g/cm$^2$, less than 0.5 μg/cm$^2$, less than 0.1 μg/cm$^2$, less than 0.05 μg/cm$^2$, or less than 0.01 μg/cm$^2$.

The association of a linker with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A linker can be configured to interact with a capture protein. A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

The interaction between the linker and the capture protein can be binding to a capture protein. The linker can be configured to interact with a capture protein by including a first binding partner in the linker that can interact with the capture protein. The first binding partner can be known binding partner of the capture protein or a portion thereof. The first binding partner can include an ion. The ion can be a metal ion. The metal ion can be a nickel, iron, cadmium, copper, magnesium, calcium, arsenic, lead, mercury or cobalt ion (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof.

A linker can further include a chelating region. A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine. A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together. The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein, which can be used for separating (e.g. using tag affinity techniques), increasing solubility, immobilizing, localizing or detecting a protein. The protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to bind to the corresponding binding partner (or relatively small group of related molecules or proteins) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 µM, less than 0.1 µM, or less than 0.01 µM. A first binding partner and a second binding partner can bind with a dissociation constant greater than 1 nm, greater than 0.01 µM, greater than 0.1 µM, greater than 1 M, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond between the linker and the capture protein.

The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

In some embodiments, a composition can further include a capture protein, which can be configured to specifically interact with at least one analyte. In particular, the capture protein can be configured to specifically bind to at least one analyte. Specific binding can be more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 M, less than 0.1 µM, or less than 0.01 µM. An analyte and a capture protein can bind with a dissociation constant greater than 1 nm, greater than 0.01 µM, greater than 0.1 µM, greater than 1 M, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. More specifically, the property can be a fluorescent emission within the near infrared spectrum. The property can be an emission wavelength, an emission intensity, a conductance, an electromagnetic absorbance or an emittance.

The interaction of an analyte with a capture protein can be reversible, meaning that the analyte can bind to the capture protein and then release and be free of binding. The change in a property of the nanostructure due to the interaction of an analyte with a capture protein can also be reversible. For example, the property of a nanostructure can have a first value, the analyte can bind to the capture protein and alter the property to a second value, then the analyte can release from the capture protein and the property can return to the first value.

The analyte can be a small molecule, protein, biomolecule, drug, biologic, or a metabolite thereof. For example, the analyte can be monosaccharide, a polysaccharide, an amino acid, peptide, polypeptide, protein, a nucleotide, an oligonucleotide, a lipid, a polylipid, or a combination thereof. Specifically, the capture protein can be a lectin and the analyte can include a glycan (e.g. the analyte can be a glycoprotein).

A linker can have a formula: A-L-C, where A can include a polymer, where at least a portion of the nanostructure is embedded in the polymer, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, $C(O)$, $N(R^a)C(O)O$, $OC(O)N(R^a)$, $N(R^a)C(O)N(R^b)$, $C(O)O$, or $OC(O)O$; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

Alkyl is a straight or branched hydrocarbon chain containing 1 to 10 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

The terms "alkenyl" and "alkynyl" refer to a straight or branched hydrocarbon chain containing 2 to 10 carbon atoms and one or more (preferably, 1-4 or more preferably 1-2) double or triple bonds, respectively. Some examples of alkenyl and alkynyl are allyl, 2-butenyl, 2-pentenyl, 2-hexenyl, 2-butynyl, 2-pentynyl, and 2-hexynyl.

Cycloalkyl is a monocyclic, bicyclic or tricyclic alkyl group containing 3 to 14 carbon atoms. Some examples of cycloalkyl are cyclopropyl, cyclopentyl, cyclohexyl, cycloheptyl, adamantyl, and norbornyl. Heterocycloalkyl is a cycloalkyl group containing at least one heteroatom (e.g., 1-3) such as nitrogen, oxygen, or sulfur. The nitrogen or sulfur may optionally be oxidized and the nitrogen may optionally be quaternized. Examples of heterocycloalkyl include piperidinyl, piperazinyl, tetrahydropyranyl, tetrahydrofuryl, and morpholinyl. Cycloalkenyl is a cycloalkyl group containing at least one (e.g., 1-3) double bond. Examples of such a group include cyclopentenyl, 1,4-cyclohexa-di-enyl, cycloheptenyl, and cyclooctenyl groups. By the same token, heterocycloalkenyl is a cycloalkenyl group containing at least one heteroatom selected from the group of oxygen, nitrogen or sulfur.

Aryl is an aromatic group containing a 5-14 ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1-3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

A cyclic moiety can be a fused ring formed from two or more of the just-mentioned groups.

Amino protecting groups and hydroxy protecting groups are well-known to those in the art. In general, the species of protecting group is not critical, provided that it is stable to the conditions of any subsequent reaction(s) on other positions of the compound and can be removed without adversely affecting the remainder of the molecule. In addition, a protecting group may be substituted for another after substantive synthetic transformations are complete. Examples of an amino protecting group include, but not limited to, carbamates such as 2,2,2-trichloroethylcarbamate or tertbutylcarbamate. Examples of a hydroxyl protecting group include, but not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more Cis alkoxy, or nitro. Other protecting groups and reaction conditions can be found in T. W. Greene, *Protective Groups in Organic Synthesis*, (3rd, 1999, John Wiley & Sons, New York, N.Y.).

Note that an amino group can be unsubstituted (i.e., —NH$_2$), mono-substituted (i.e., —NHR), or di-substituted (i.e., —NR$_2$). It can be substituted with groups (R) such as alkyl, cycloalkyl, heterocycloalkyl, aryl, heteroaryl, aralkyl, or heteroaralkyl. Halo refers to fluoro, chloro, bromo, or iodo.

The composition can include a chelator-containing compound, which can include a chelator region and a non-chelator region. C can be the chelator region. L can include the non-chelator region.

In some circumstances, A can include a polymer [(M)$_x$(N)$_y$(Q)$_z$]$_q$, where each of M, N and Q, independently, can be selected from the group consisting of a linear or cyclic C$_3$-C$_8$ hydrocarbyl, heterocyclyl, cyclyl, or aryl including one or more amine, alcohol or carboxylic acid group, where each M-N, M-Q or N-Q can include O, S, N(R$^a$), C(O), N(R$^a$)C(O)O, OC(O)N(R$^a$), N(R$^a$)C(O)N(R$^b$), C(O)O, or OC(O)O, each of R$^a$ and R$^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

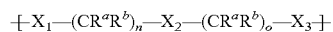

where each X$_1$, X$_2$ and X$_3$, can be O, S, N(R$^a$), C(O), N(R$^a$)C(O)O, OC(O)N(R$^a$), N(R$^a$)C(O)N(R$^b$), C(O)O, or OC(O)O, each of R$^a$ and R, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, H$_z$G ((CH$_2$)$_n$CO$_2$H)$_y$ and salts thereof, where G can be a bond, C, O, S, P, P=O or N; n is 0-6; and z and y can be selected to satisfy the valence requirements of G. In other preferred embodiments, the compound can have the formula,

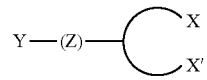

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

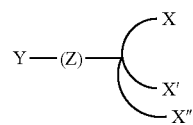

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_n COOH)_2$, $(HOOC(CH_2)_n)_2P(O)CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

In some embodiments, the composition can include a nanostructure and a linker having a formula:

A-L-C, where A can include the polymer covalently bonded to a portion of the nanostructure, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

The composition can include a chelator-containing compound, which can include a chelator region and a non-chelator region. C can be the chelator region. L can include the non-chelator region.

In some circumstances, A can include a polymer $[(M)_x(N)_y(Q)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

$+X_1—(CR^aR^b)_n—X_2—(CR^aR^b)_o—X_3+$ where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$ and salts thereof, where G can be a bond, C, O, S, P, P=O or N; n is 0-6; and z and y can be selected to satisfy the valence requirements of G. In other preferred embodiments, the compound can have the formula,

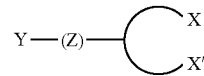

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

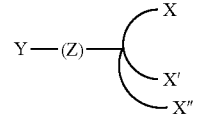

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_n COOH)_2$, $(HOOC(CH_2)_n)_2P(O)CH_2CH_2P(O)((CH_2)_n COOH)_2$, $HSCH_2CH_2CH(SH)(CH_2)_4CONH(CH_2)_nCOOH$, where can is an integer between 1 and 10, or $N_\alpha,N_\alpha$-bis(carboxymethyl)-L-lysine.

Compounds can be prepared according to published procedures such as those described, for example, in Parameswara et al., Synthesis, 815-818 (1980) and Denny et al., J. Org. Chem., 27, 3404 (1962), which is incorporated by reference in its entirety.

In another aspect, an array can include a plurality of analysis regions on a substrate. A substrate can be glass or plastic.

An analysis region can be a divot, a tube, a tray, a well or a similar compartment for suitable for containing a liquid sample. In some cases, an analysis region can include a droplet or spot on the surface of a substrate. In those cases, an analysis region can be formed by spotting the composition on a substrate. A plurality of analysis regions can be in a pattern on a substrate. A pattern can include concentric circles, a spiral, a row, a column or a grid.

The number of linkers associated with the nanostructure present in the analysis region can exceed the number of capture proteins. More specifically, the number of capture protein binding sites on linkers associated with a nanostructure can exceed the number of capture proteins. The ratio of capture protein binding sites on linkers associated with a nanostructure to capture proteins can be greater than 1.1 to 1, greater than 1.5 to 1, greater than 2 to 1, greater than 5 to 1, or greater than 10 to 1. Having an excess of capture protein binding sites on linkers associated with a nanostructure can minimize the amount of unbound capture protein in a sample. Unbound capture proteins within the sample can compete with capture proteins bound to the composition for binding to the analyte. This can affect the accuracy and/or precision of the analyte detection. Having an excess of capture protein binding sites on linkers associated with a nanostructure can also increase the analyte concentration range over which analyte can be accurately detected because the saturation limit of the binding sites is increased.

The interaction between the linker and the capture protein can be binding to a capture protein. The linker can be configured to interact with a capture protein by including a first binding partner in the linker that can interact with the capture protein. The first binding partner can be known binding partner of the capture protein or a portion thereof. The first binding partner can include an ion. The ion can be a metal ion. The metal ion can be nickel, iron, cadmium, copper, magnesium, calcium, arsenic, lead, mercury or cobalt (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof.

A linker can further include a chelating region. A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine. A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together. The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein. The protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to detect a given analyte (or relatively small group of related analytes) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 M, less than 0.1 μM, or less than 0.01 μM. A first binding partner and a second binding partner can bind with a dissociation constant greater than 1 nm, greater than 0.01 μM, greater than 0.1 μM, greater than 1 M, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond between the linker and the capture protein.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

Capture proteins can be synthesized in situ by performing in vitro transcription followed by in vitro translation in an analysis region. In vitro transcription can produce RNA encoding for a capture protein from the DNA sequence encoding for the capture protein. DNA encoding for a capture protein can be added to an analysis region. An in vitro transcription reaction mixture can also be added to an analysis region. The in vitro transcription reaction mixture can include nucleic acids, RNA polymerase, cell extract, salts or buffers.

A first subset of analysis regions can differ from a second subset of analysis regions by the DNA present in each. For example, different pairs of primers can be used to PCR amplify different DNA sequences from a cDNA library. A second set of primers that can overlap a portion of the sequence of the first set of primers can be used to add transcription and/or translation regulatory elements to the amplified DNA. The amplified DNA can be added to an analysis region. A first subset of analysis regions can include a first DNA sequence encoding for a first capture protein. A second subset of analysis regions can include a second DNA sequence encoding for a second capture protein, and an Nth subset of analysis regions can include an Nth DNA sequence encoding for an Nth capture protein. N can be an integer between 1 and 10.

In some embodiments, at least one analysis region can further include a ribosome and the composition of the at least one analysis region can further include a capture protein. The capture protein can be configured to specifically interact with at least one analyte. In vitro translation can produce a capture protein from an RNA sequence encoding for the capture protein. An RNA sequence can be in vitro transcribed within an analysis region from a DNA sequence. A ribosome can then translate the RNA into a protein, for example, the capture protein. A ribosome can include ribosomal RNA and ribosomal proteins. The ribosome can be a component of a cellular extract, for example S30 extract. The ribosome can be added to the analysis region as part of an in vitro translation reaction mixture. Other components of an in vitro translation reaction mixture can include amino acids, cell extract, tRNA, salts or buffers. The in vitro translation reaction mixture can be used to synthesize the capture protein in situ.

A first subset of analysis regions can differ from a second subset of analysis regions by the RNA present in each. For example, a first subset of analysis regions can include a first RNA sequence encoding for a first capture protein. A second subset of analysis regions can include a second RNA sequence encoding for a second capture protein, and an Nth subset of analysis regions can include an Nth RNA sequence encoding for an Nth capture protein. N can be an integer between 1 and 10.

Additionally, a first subset of analysis regions can differ from a second subset of analysis regions by the capture protein within the analysis regions. A first subset of analysis regions can include a first composition, which can include first capture protein. A second subset of analysis regions can include a second composition, which can include a second capture protein, and an Nth subset of analysis regions can include an Nth composition which can include an Nth capture protein. N can be an integer between 1 and 5000. Changing the capture proteins can allow experiments involving an analyte with multiple natural binding partners or different analytes to take place at the same time. It can also allow for the development of a capture protein library against which an analyte can be tested for binding.

In situ synthesis of capture proteins can allow for the capture proteins to interact with a linker shortly after being synthesized. This can, in turn, allow for the capture proteins to be directly immobilized in the analysis region. An advantage of in situ synthesis can be the elimination of purification steps required by other techniques. Elimination of purification steps can be beneficial for proteins that are difficult to purify, aggregate during purification, or produce a low yield following purification.

In some embodiments, a composition can further include a capture protein, which can be configured to specifically interact with at least one analyte. In particular, the capture protein can be configured to specifically bind to at least one analyte. Specific binding can describe a more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 M, less than 0.1 µM, or less than 0.01 µM. An analyte and a capture protein can bind with a dissociation constant greater than 1 nm, greater than 0.01 µM, greater than 0.1 µM, greater than 1 M, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. The property can be an emission wavelength, an emission intensity, a conductance, an electromagnetic absorbance or an emittance.

In some embodiments, at least one analysis region can further include a sample. The sample can include a gas, a liquid or a solid. In other embodiments, the sample can be a biological fluid or cell lysate. The sample can include an analyte.

The number of capture proteins interacting with the composition can exceed the number of analyte molecules present in a sample. More specifically, the number of analyte binding sites on capture proteins interacting with the composition can exceed the number of analyte molecules present in a sample. The ratio of analyte binding sites on capture proteins interacting with the composition to analyte can be greater than 1.1 to 1, greater than 1.5 to 1, greater than 2 to 1, greater than 5 to 1, or greater than 10 to 1. The number of binding sites on capture proteins interacting with the composition can limit detection of analyte if the number of analyte molecules is about or exceeds the number binding sites. Because detection of the analyte can be dependent on a change in a property of a nanostructure due to analyte binding, if a binding site is not available for the analyte, the analyte cannot bind and change a property of the nanostructure, and consequently, can go undetected. In other words, when the composition is saturated with analyte, unbound analyte can go undetected.

A first subset of analysis regions can differ from a second subset of analysis regions by the sample within the analysis regions. A first subset of analysis regions can include a first sample. A second subset of analysis regions can include a second sample, and an Nth subset of analysis regions can include an Nth sample. N can be an integer between 1 and 5000. Changing the samples can allow experiments involving one analyte present in different samples or two or more analytes each present in a different sample. For example, a first sample can include a first analyte and a second sample can include a second analyte. Said another way, an Nth subset of analysis regions can include an Nth sample which can include an Nth analyte, where N can be an integer between 1 and 5000. Alternatively, a first sample can include a first analyte and a second sample can include a first analyte. In other words, an Nth subset of analysis regions can include an Nth sample which can include first analyte, where N can be an integer between 1 and 10.

In another aspect, a method for detecting protein binding can include providing a composition. The composition can include a nanostructure and a linker.

A nanostructure can be an article having at least one cross-sectional dimension between opposed boundaries of less than about 1 micron. In some embodiments, a nanostructure can have at least one cross-sectional dimension between opposed boundaries of less than about 500 nm, less than about 250 nm, less than about 100 nm, less than about 75 nm, less than about 50 nm, less than about 25 nm, less than about 10 nm, or in some cases, less than about 1 nm.

Examples of a nanostructure can include a nanotube (including a carbon nanotube), a nanowire (including a carbon nanowire), a nanorod, a nanofiber, graphene or a quantum dot, among others. A nanostructure can include a fullerene, for example, a carbon nanotube, a buckyball, a buckytube or a fullerene ring. A nanostructure can also include a nanocrystal. A nanostructure can include a metal, a nonmetal, or semiconductor.

A nanostructure can be a photoluminescent nanostructure, which can exhibit photoluminescence. In some instances, photoluminescent nanostructures can exhibit fluorescence. For example, a photoluminescent nanostructure can emit fluorescence with a wavelength in the near infrared spectrum. In some instances, photoluminescent nanostructures can exhibit phosphorescence. A photoluminescent nanostructure can be a nanotube. A nanotube can be a carbon nanotube. A carbon nanotube can be a single walled carbon nanotube. In some embodiments, a photoluminescent nanostructure can be a semi-conductive single-walled carbon nanotube. Additional examples of photoluminescent nanostructures can include, but are not limited to, double-walled carbon nanotubes, multi-walled carbon nanotubes, semi-conductor quantum dots, semi-conductor nanowires, or graphene, among others.

A nanostructure can have a property that can be altered by changes in the environment of the nanostructure. The property can be detectable or observable. The property can also be measurable so that changes in the property can be described or quantified. The property can be photoluminescence, conductivity, polarity, or resonance. Photoluminescence can be fluorescence or phosphorescence. The photoluminescence can be fluorescence with a wavelength within the near infrared spectrum. The property can be an emission wavelength, an emission intensity, a conductance, an electromagnetic absorbance or an emittance.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A nanostructure can exhibit solvatochromism. Analytes that change the local dielectric constant can change the photoluminescence of the nanostructure. An interaction of an electron-donating or -withdrawing molecule with a nanostructure can alter a property, for example photoluminescence, of the nanostructure. An interaction with a nanostructure can be direct or indirect. Additionally, more than one electron-donating or -withdrawing molecule can interact with a nanostructure and each molecule can alter a property of the nanostructure. A second molecule can also interact with an electron-donating or -withdrawing molecule and change the relationship of the electron-donating or -withdrawing molecule to the nanostructure. This can also alter a nanostructure property. For example, a first molecule can interact with the nanostructure and alter a property (e.g. the photoluminescence) of the nanostructure, and then a second molecule can interact with either the nanostructure or the first molecule and further alter a property (e.g. the photoluminescence) of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

The association of a linker with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

Providing a composition can include making the composition or obtaining the composition. Making the composition can include creating the nanostructure and/or the linker or obtaining the nanostructure and/or the linker. Making the composition can include sonicating a solution including a nanostructure and a linker. The solution can be chilled during sonication, for example, the solution can be put on ice. Making the composition can also include mixing a solution including a nanostructure and a linker.

Figure 1B:
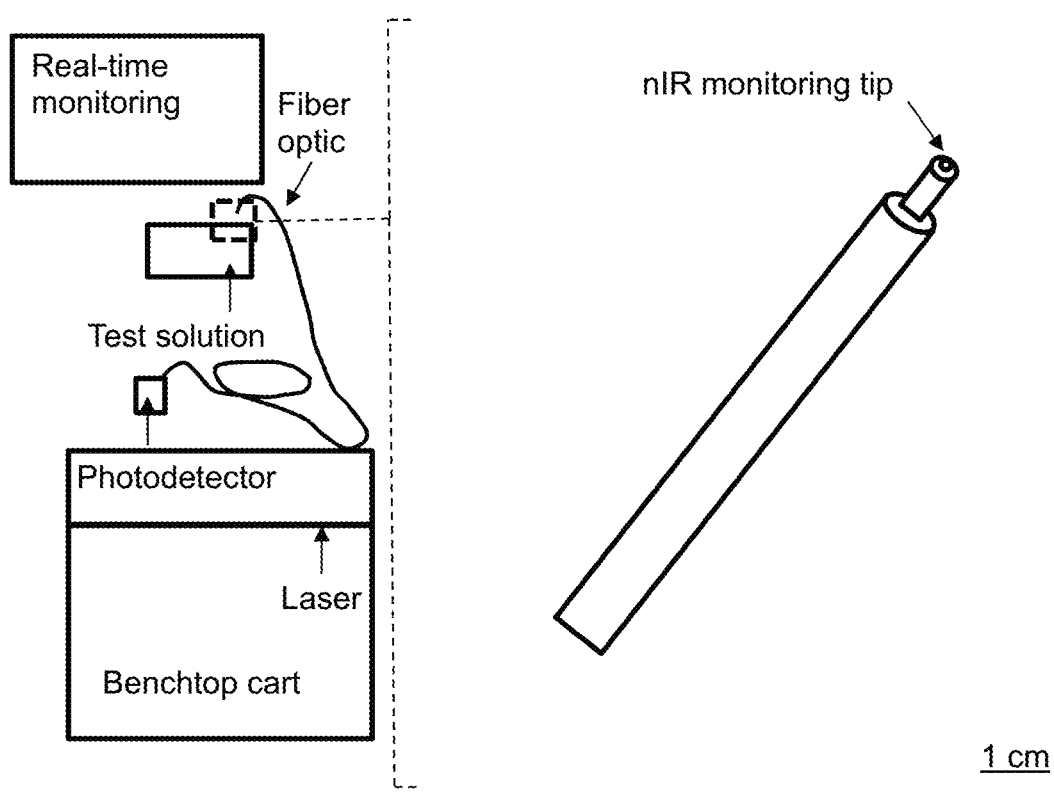
FIG. 1B depicts a system including a fiber optic, test solution, photodetector, and laser.

Providing a composition can include providing an array. An array can include a plurality of analysis regions on a substrate. At least one analysis region can include a composition (FIGS. 1a and 1b).

An analysis region can be a divot, a tube, a tray, a well or a similar compartment for suitable for containing a liquid sample. In some cases, an analysis region can include a droplet or spot on the surface of a substrate. In those cases, an analysis region can be formed by spotting the composition on a substrate. A plurality of analysis regions can be in a pattern on a substrate. A pattern can include concentric circles, a spiral, a row, a column or a grid.

In some embodiments, the plurality of analysis regions can include two or more subsets of analysis regions. For example, a first subset of analysis regions can differ from a second subset of analysis regions by including a different nanostructure, a different linker, a different binding partner, a different capture protein, a different analyte or a different sample. Additionally, a first subset of analysis regions can differ from a second subset of analysis regions by including a different environmental factor including a buffer, a reagent, a nutrient, a serum, an exposure to light, an oxygen concentration, a temperature or a pH.

A method of detecting protein binding can be a high-throughput screening assay. An array can be used for the method. The compositions in different analysis regions can include different components, be exposed to different conditions or be exposed to different samples and/or analytes, including different analyte concentrations.

A method for detecting protein binding can include providing a capture protein to the composition. The capture protein can be capable of interacting with an analyte. The capture protein also can interact with the linker.

A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

Providing a capture protein can include synthesizing protein, for example, in cells or in a cell-free protein synthesis reaction (i.e. in vitro). Synthesizing a capture protein can include in situ protein synthesis performed at the location that can include the composition. In vitro capture protein synthesis can include in vitro transcription and/or in vitro translation.

Synthesizing a capture protein in vitro can include performing in vitro transcription and in vitro translation simultaneously by providing DNA encoding for a capture protein, providing an in vitro transcription/translation reaction mixture, and incubating the DNA with the transcription/translation reaction mixture.

Alternatively, synthesizing a capture protein in vitro can include performing in vitro transcription and in vitro translation sequentially. Synthesizing a capture protein can include providing DNA encoding for the capture protein, providing an in vitro transcription reaction mixture, incubating the reaction mixture with the DNA encoding for the capture protein, thereby synthesizing RNA encoding for the capture protein. Synthesizing a capture protein can further include providing an in vitro translation reaction mixture, incubating the translation reaction mixture with the RNA encoding for the capture protein, thereby synthesizing capture protein.

The in vitro transcription reaction mixture can include nucleic acids, RNA polymerase, cell extract, salts or buffers. An in vitro translation reaction mixture can include amino acids, cell extract, tRNA, salts or buffers. A ribosome can also be part of an in vitro translation reaction mixture and can translate the RNA into a protein, for example, the capture protein. A ribosome can include ribosomal RNA and ribosomal proteins. The ribosome can be a component of a cellular extract, for example S30 extract, rabbit reticulosyte lysate, wheat germ extract, or E. coli extract.

In situ synthesis of capture proteins can allow for the capture proteins to interact with a linker shortly after being synthesized. This can, in turn, allow for the capture proteins to be directly immobilized. An advantage of in situ synthesis can be the elimination of purification steps required by other techniques. Elimination of purification steps can be beneficial for proteins that are difficult to purify, aggregate during purification, or produce a low yield following purification.

A linker can be configured to interact with a capture protein. The interaction can be binding to a capture protein. The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

The change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

The number of linkers associated with the nanostructure present in the analysis region can exceed the number of capture proteins. More specifically, the number of capture protein binding sites on linkers associated with a nanostructure can exceed the number of capture proteins. The ratio of capture protein binding sites on linkers associated with a nanostructure to capture proteins can be greater than 1.1 to 1, greater than 1.5 to 1, greater than 2 to 1, greater than 5 to 1, or greater than 10 to 1. Having an excess of capture protein binding sites on linkers associated with a nanostructure can minimize the amount of unbound capture protein in a sample. Unbound capture proteins within the sample can compete with capture proteins bound to the composition for binding to the analyte. This can affect the accuracy and/or precision of the analyte detection. Having an excess of capture protein binding sites on linkers associated with a nanostructure can also increase the analyte concentration range over which analyte can be accurately detected because the saturation limit of the binding sites is increased.

A method for detecting protein binding can further include exposing the composition and capture protein to a sample. Exposing can include adding the sample to the location of the composition and the capture protein, for example, an analysis region.

The sample can include a gas, a liquid or a solid. In other embodiments, the sample can be a biological fluid or cell lysate. The sample can include an analyte. The analyte can be a small molecule, protein, biomolecule, drug, biologic, or a metabolite thereof. For example, the analyte can be monosaccharide, a polysaccharide, an amino acid, peptide, polypeptide, protein, a nucleotide, an oligonucleotide, a lipid, a polylipid, or a combination thereof. Specifically, the capture protein can be a lectin and the analyte can include a glycan (e.g. the analyte can be a glycoprotein).

The number of capture proteins interacting with the composition can exceed the number of analyte molecules present in a sample. More specifically, the number of analyte binding sites on capture proteins interacting with the composition can exceed the number of analyte molecules present in a sample. The ratio of analyte binding sites on capture proteins interacting with the composition to analyte can be greater than 1.1 to 1, greater than 1.5 to 1, greater than 2 to 1, greater than 5 to 1, or greater than 10 to 1. The number of binding sites on capture proteins interacting with the composition can limit detection of analyte if the number of analyte molecules is about or exceeds the number binding sites. Because detection of the analyte can be dependent on a change in a property of a nanostructure due to analyte binding, if a binding site is not available for the analyte, the analyte cannot bind and change a property of the nanostructure, and consequently, can go undetected. In other words, when the composition is saturated with analyte, unbound analyte can go undetected.

A method for detecting protein binding can include monitoring a property of the composition. A property can be conductivity, polarity, or resonance. A property can be photoluminescence, including fluorescence or phosphorescence. The property can be an emission wavelength, an emission intensity, a conductance, an electromagnetic absorbance or an emittance.

Monitoring the property can include observing the property of the composition alone. Monitoring the property can include monitoring the property after the composition has been exposed to a sample. Monitoring the property can include monitoring the property after the composition has been exposed to an analyte. Monitoring the property can include monitoring the property after the composition has been exposed to known concentrations of an analyte.

Monitoring a property of the composition can include observing the property through a microscope. The microscope can be an optical or a fluorescence microscope. In particular, the microscope can detect near infrared fluorescence. Monitoring a property of the composition can include measuring the property using a microscope. Monitoring a property of the composition can include monitoring the property using still photography or movies. The photography or movies can be on film media or digital form.

Monitoring a property can include taking a data point reflecting a value of a property. This can be repeated. A representation of the data points, for example, a chart or graph, can be created from the data points.

Monitoring a property can occur in real-time and allow for real-time detection of analyte binding. Real-time detection can allow in situ identification of a wide dynamic range of molecular interactions.

A method of detecting protein binding can include determining the presence of an analyte in the sample based on the monitored property. Determining the presence of an analyte can include determining the absence of the analyte. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

In some embodiments, the capture protein can be a lectin and the analyte can include a glycan. An analyte can include more than one glycan. A lectin can have a weaker affinity for the glycan. A lectin may or may not have selective binding for a glycan. For example, a lectin can bind to a single glycan or multiple glycans. Sometimes, microarrays can include selected lectins, which can be used as high-throughput platforms for profiling glycoproteins. Each glycan group can have a highly-specific lectin pair. It may be possible to profile using a smaller set of lectins, if the entire affinity spectrum can be utilized. A Weak Affinity Dynamic Microarray (WADM) can utilize transducers that allow for single molecule adsorption and desorption dynamics to be measured in real time, as opposed to equilibrium binding only. Lectins, can have much weaker affinities yet larger numbers of binding partners compared to other proteins, for example, antibodies. Lectins can potentially fingerprint glycosylated proteins with higher resolution by dynamically monitoring the on and off binding rates of a target glycan. This can reduce the complexity and increase the robustness of lectin microarrays.

The composition, array and/or the method for detecting protein binding can have a number of advantages over other protein detection technologies. First, neither the composition nor the array require labeling of the target analyte protein, which can be perturbative to a protein—protein interaction of interest. Second, the composition and/or array can be suitable for the detection of any protein—protein interaction, not just antigen—antibody pairs. Third, the composition and/or the array can be capable of detecting single protein binding events, which has not been demonstrated using other detection techniques.

The composition, array and/or the method for detecting protein binding can have a number of advantages over existing label-free protein-protein detection methods. First, fabrication of the array can be simple and fairly cheap as in situ immobilization of proteins during synthesis directly on the array can eliminate the need for separate protein preparation and purification. Second, the array and the method for detecting protein binding can allow for high-throughput detection of protein-protein interactions.

Fluorescent nanosensors hold promise to address analytical challenges in the biopharmaceutical industry. The monitoring of therapeutic protein critical quality attributes such as aggregation is a longstanding challenge requiring low detection limits and multiplexing of different product parameters. However, general approaches for interfacing nanosensors to the biopharmaceutical process remain minimally explored to date. Herein, an integrated fiber optic nanosensor element, measuring sensitivity, response time, and stability is described for applications to the rapid process monitoring. The fiber optic-nanosensor interface, or optode, consists of label-free nIR fluorescent single-walled carbon nanotube transducers embedded within a protective yet porous hydrogel attached to the end of the fiber waveguide. The optode platform is shown to be capable of differentiating the aggregation status of human immunoglobulin G, reporting the relative fraction of monomers and dimer aggregates with sizes 5.6 and 9.6 nm, respectively, in under 5 minutes of analysis time. A lab-on-fiber design has the potential for at-line monitoring with integration of miniaturized sensor tips having high mechanical flexibility. A parallel measurement of fluctuations in laser excitation allows for intensity normalization and significantly lower noise level (3.7-times improved) when using lower quality lasers, improving the cost effectiveness of the platform. As an application, the capability of the fully-integrated lab-on-fiber system to rapid monitoring of various bioanalytes including serotonin, norepinephrine, adrenaline, and hydrogen peroxide, in addition to proteins and their aggregation states has been demonstrated. These results in total constitute an effective form factor for nanosensor based transducers for applications in industrial process monitoring.

Pharmaceutical manufacturing involves a series of complex processing steps including extraction, purification, and polishing. See, for example, Rantanen, J.; Khinast, J. The Future of Pharmaceutical Manufacturing Sciences. *J. Pharm. Sci.* 2015, 104, 3612-3638, which is incorporated by reference in its entirety. Protein and macromolecular therapeutics in particular need to be controlled for stability with respect to aggregation caused by aberrant processing and storage conditions such as excessive heat, light, shear, ionic strength, and pH. See, for example, Martin, N.; Ma, D.; Herbet, A.; Boquet, D.; Winnik, F. M.; Tribet, C. Prevention of Thermally Induced Aggregation of IgG Antibodies by Noncovalent Interaction with Poly(acrylate) Derivatives. *Biomacromolecules* 2014, 15, 2952-2962; and Kastelic, M.; Kalyuzhnyi, Y. V.; Hribar-Lee, B.; Dill, K. A.; Vlachy, V. Protein Aggregation in Salt Solutions. *Proc. Nat. Acad. Sci. U.S.A* 2015, 112, 6766-6770 Each of which are incorporated by reference in its entirety. Undesired aggregates include monomer-monomer nucleation and aggregate-aggregate coalescence resulting in particles ranging from 10 nm to greater than 10 μm. See, for example, Amin, S.; Barnett, G. V.; Pathak, J. A.; Roberts, C. J.; Sarangapani, P. S. Protein Aggregation, Particle Formation, Characterization & Rheology. *Curr. Opin. Colloid. In.* 2014, 19, 438-449, which is incorporated by reference in its entirety. Protein products that remain correctly folded upon aggregation still possess limited solubility limiting the maximum dosage of drug. Also, changes in solution viscosity inhibit intramuscular or subcutaneous delivery. See, for example, Schmit, J. D.; He, F.; Mishra, S.; Ketchem, R. R.; Woods, C. E.; Kerwin, B. A. Entanglement Model of Antibody Viscosity. *J. Phys. Chem. B* 2014, 118, 5044-5049; Pathak, J. A.; Sologuren, R. R.; Narwal, R. Do Clustering Monoclonal Antibody Solutions Really Have a Concentration Dependence of Viscosity?. *Biophys. J.* 2013, 104, 913-923; and Roberts, C. J. Protein Aggregation and Its Impact on Product Quality. *Curr. Opin. Biotech.* 2014, 30, 211-217, each of which is incorporated by reference in its entirety. Protein aggregation can also induce immunogenic responses, the onset of autoimmune disease. See, for example, Jiskoot, W.; Randolph, T. W.; Volkin, D. B.; Middaugh, C. R.; Schneich, C.; Winter, G.; Friess, W.; Crommelin, D. J. A.; Carpenter, J. F. Protein Instability and Immunogenicity: Roadblocks to Clinical Application of Injectable Protein Delivery Systems for Sustained Release. *J. Pharm. Sci.* 2012, 101, 946-954; and Macdougall, I. C. Antibody-Mediated Pure Red Cell Aplasia (PRCA): Epidemiology, Immunogenicity and Risks. *Nephrol. Dial. Transplant.* 2005, 20, iv9-iv15, each of which is incorporated by reference in its entirety. There is an increased need from both a safety and regulatory standpoint for rapid diagnostics that can monitor product quality, specifically to discern monomers from dimers, trimers, and polymers. See, for example, Berkowitz, S. A.; Engen, J. R.; Mazzeo, J. R.; Jones, G. B. Analytical Tools for Characterizing Biopharmaceuticals and The Implications for Biosimilars. *Nat. Rev. Drug Discov.* 2012, 11, 527-540, which is incorporated by reference in its entirety. As a potential solution, nanotechnology enabled sensors, such those based on carbon nanotubes, graphene, or plasmonic nanoparticles, exhibit ultra-low detection limits and rapid transduction time due to high surface areas. See, Kruss, S,; Hilmer, A. J.; Zhang, J.; Reuel, N. F.; Mu, B.; Strano, M. S. Carbon Nanotubes as Optical Biomedical Sensors. *Adv. Drug Deliv. Rev.* 2013, 65, 1933-1950; Liu, Y.; Dong, X.; Chen, P. Biological and Chemical Sensors Based on Graphene Materials. *Chem. Soc. Rev.* 2012, 41, 2283-2307; Doria, G.; Conde, J.; Veigas, B.; Giestas, L.; Almeida, C.; Assuncao, M.; Rosa, J.; Baptista, P. V. Noble Metal Nanoparticles for Biosensing Applications. *Sensors* 2012, 12, 1657-1687; and Holzmeister, P.; Acuna, G. P.; Grohmann, D.; Tinnefeld, P. Breaking the Concentration Limit of Optical Single-Molecule Detection. *Chem. Soc. Rev.* 2014, 43, 1014-1028, each of which is incorporated by reference in its entirety. However, the conceptual design and fabrication of an interface between such sensors and a form factor compatible with online or at-line monitoring of a pharmaceutical manufacturing process is lacking in the literature. This gap is addressed by designing and implementing a fiber optic interface that serves this purpose.

A wide variety of analytical methods are utilized to quantify organic molecules, even during chemical manufacturing. See, for example, Ray, A.; Bristow, T.; Whitmore, C.; Mosely, J. On-Line Reaction Monitoring by Mass Spectrometry, Modern Approaches for the Analysis of Chemical Reactions. *J. Mass Spec Rev.* 2018, 37, 565-579, which is incorporated by reference in its entirety. However, proteins in particular must be monitored for aggregation as described above. To this end, conventional methods including high performance liquid chromatography (HPLC), dynamic light scattering (DLS), capillary electrophoresis, and single particle tracking (SPT) have been widely used with different levels of complexity and assay time. See, for example, Fekete, S.; Beck, A.; Veuthey, J. L.; Guillarme, D. Theory and Practice of Size Exclusion Chromatography for the Analysis of Protein Aggregates. *J. Pharm. Biomed. Anal.* 2014, 101, 161-173; Yu, Z.; Reid, J. C.; Yang, Y.-P. Utilizing Dynamic Light Scattering as a Process Analytical Technology for Protein Folding and Aggregation Monitoring in Vaccine Manufacturing. *J. Pharm. Sci.* 2013, 102, 4284-4290; Righetti, P. G.; Verzola, B. Folding/Unfolding/Refolding of Proteins: Present Methodologies in Comparison with Capillary Zone Electrophoresis. *Electrophoresis* 2001, 22, 2359-2374; Gong, X.; Park, M.; Parviz, D.; Silmore, K. S.; Gordiichuk, P.; Lew, T. T. S.; Strano, M. S. Single-Particle Tracking for Understanding Polydisperse Nanoparticle Dispersions. *Small* 2019, 15,1901468; and Silmore, K. S.; Gong, X.; Strano, M. S.; Swan, J. W. High-Resolution Nanoparticle Sizing with Maximum A Posteriori Nanoparticle Tracking Analysis. *ACS Nano* 2019, 13, 3940-3952, each of which is incorporated by reference in its entirety. Despite considerable progress, critical limitations remain in both speed and quantification resolution: these techniques vary in the amount and resolution of structural and size information that they provide, with no single analytical technique being capable of fully elucidating the quantitative protein size distribution. See, for example, Silmore, K. S.; Gong, X.; Strano, M. S.; Swan, J. W. High-Resolution Nanoparticle Sizing with Maximum A Posteriori Nanoparticle Tracking Analysis. *ACS Nano* 2019, 13, 3940-3952; Wang, W. Protein Aggregation and Its Inhibition in Biopharmaceutics. *Int. J. Pharm.* 2005, 289, 1-30; and Zolls, S.; Tantipolphan, R.; Wiggenhorn, M.; Winter, G.; Jiskoot, W.; Friess, W.; Hawe, A. Particles in Therapeutic Protein Formulations, Part 1: Overview of Analytical Methods. *J. Pharm. Sci.* 2012, 101, 914-935, each of which is incorporated by reference in its entirety. Additionally, these analytical tools remain challenging to implement as online or at-line monitoring devices. See, for example, Hong, M. S.; Severson, K. A; Mo, J.; Lu, A. E.; Love, J. C.; Braatz, R. D. Challenges and Opportunities in Biopharmaceutical Manufacturing Control. *Comput. Chem. Eng.* 2018, 110, 106-114, which is incorporated by reference in its entirety. Thus, there is a need for the development of new analytical technologies capable of measuring target proteins rapidly with resolution at monomer level. More importantly, the analytical technology should be portable and easily coupled to existing benchtop instrument for quality assessment as part of the online or at-line production process. See, for example, Hong, M. S.; Severson, K. A; Mo, J.; Lu, A. E.; Love, J. C.; Braatz, R. D. Challenges and Opportunities in Biopharmaceutical Manufacturing Control. *Comput. Chem. Eng.* 2018, 110, 106-114; and Ündey, C.; Ertunç, S.; Mistretta, T.; Looze, B. Applied Advanced Process Analytics in Biopharmaceutical Manufacturing: Challenges and Prospects in Real-Time Monitoring and Control. *J. Process Contr.* 2010, 20, 1009-1018, which is incorporated by reference in its entirety.

Nanosensors including single-walled carbon nanotube (SWNT) are promising approaches toward rapid, label-free, and single molecule level biopharmaceutical characterization and have been developed for glycoprotein characterization, biomarker detection, and characterization of protein-binding interactions. See, for example, Reuel, N. F.; Grassbaugh, B.; Kruss, S.; Mundy, J. Z.; Opel, C.; Ogunniyi, A. O.; Egodage, K.; Wahl, R.; Helk, B.; Zhang, J. Q.; Kalcioglu, Z. I.; Tvrdy, K.; Bellisario, D. O.; Mu, B.; Blake, S. S.; Van Vliet, K. J.; Love, J. C.; Wittrup, K. D.; Strano, M. S. Emergent Properties of Nanosensor Arrays: Applications for Monitoring IgG Affinity Distributions, Weakly Affined Hypermannosylation, and Colony Selection for Biomanufacturing. *ACS Nano* 2013, 7, 7472-7482; Zhang, J. Q.; Kruss, S.; Hilmer, A. J.; Shimizu, S.; Schmois, Z.; De La Cruz, F.; Barone, P. W.; Reuel, N. F.; Heller, D. A.; Strano, M. S. A Rapid, Direct, Quantitative, and Label-Free Detector of Cardiac Biomarker Troponin T Using Near-Infrared Fluorescent Single-Walled Carbon Nanotube Sensors. *Adv. Healthcare Mater.* 2014, 3, 412-423; and Nelson, J. T.; Kim, S.; Reuel, N. F.; Salem, D. P.; Bisker, G.; Landry, M. P.; Kruss, S.; Barone, P. W; Kwak, S.; Strano, M. S. Mechanism of Immobilized Protein A Binding to Immunoglobulin G on Nanosensor Array Surfaces. *Anal. Chem.* 2015, 87, 8186-8193, each of which is incorporated by reference in its entirety. Their optical readout is well suited for sensor multiplexing, in which nanosensor arrays were fabricated and characterized for protein detection. See, for example, Dong, J. Y.; Salem, D. P.; Sun, J. H.; Strano, M. S. Analysis of Multiplexed Nanosensor Arrays Based on Near-Infrared Fluorescent Single-Walled Carbon Nanotubes. *ACS Nano* 2018, 12, 3769-3779, which is incorporated by reference in its entirety. However, despite these advantages it is not clear how to formulate such sensors into an interface to the process environment.

As described herein, a fiber optic (optode) benchtop platform interfaces the advantages of nanoparticle based sensors with a probe form factor compatible with industrial process monitoring. Dynamic monitoring of protein aggregation, a challenging problem in pharmaceutical manufacturing has been demonstrated. The optode consists of a single optical fiber that performs both the excitation and signal collection component of fluorescent nanosensor evaluations. The sensor element consists of chitosan-wrapped SWNT nanosensors with excitation and emission in the visible and near-infrared (nIR) ranges, respectively. With the optode fiber's small form factor and mechanical flexibility, all the components including optode fiber, laser, nanosensors, nIR detectors, and measurement instrument are compactly and fully integrated into single portable benchtop platform, which can be easily and directly applied to pharmaceutical processing steps with at-line analysis. Using this setup, the differentiation of immunoglobulin G (IgG) from 5.6 nm monomers to 9.6 nm dimer aggregates as well as bioanalytes including serotonin, norepinephrine, adrenaline, and hydrogen peroxide has been demonstrated. Finally, the lab-on-fiber monitoring system has been demonstrated with integration of user-defined 3D-printed miniaturized sensing tips.

The overall strategy for optode development is divided into two steps: (1) development of the optical fiber for excitation and collection of a nanosensor tip and (2) attachment of an optically coupled hydrogel with embedded nanosensors to the optical fiber end, facilitated by adaptors for this purpose.

Figure 18A:
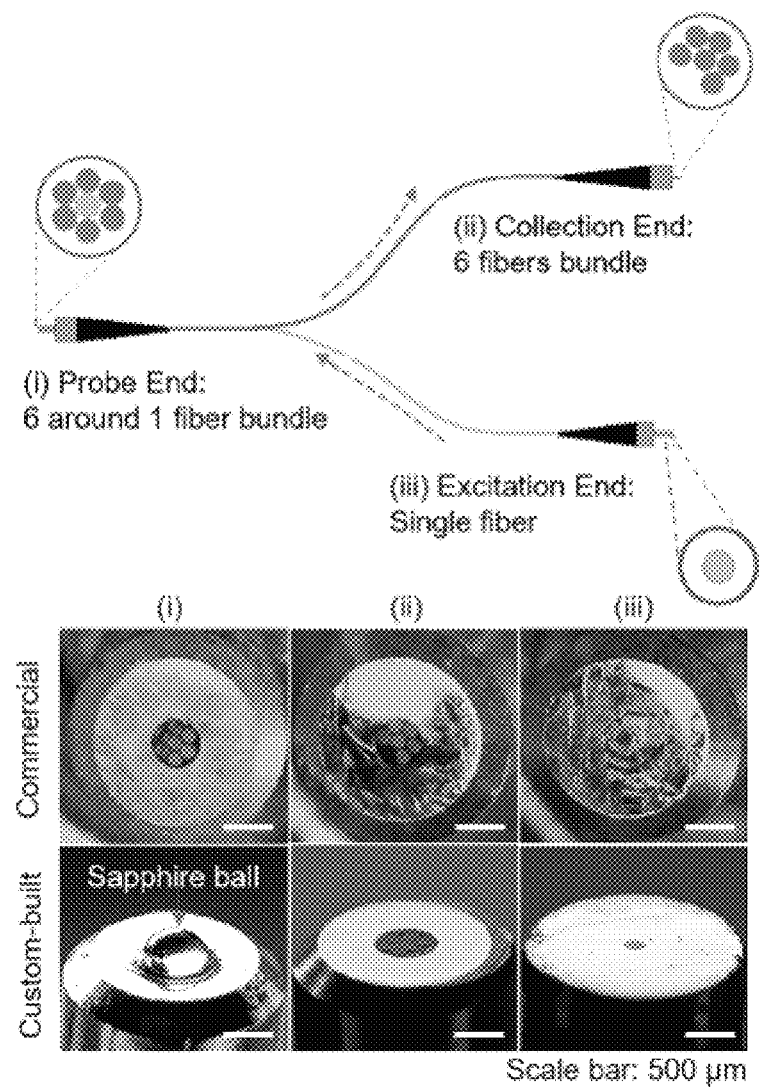
FIGS. 18A-18C show fabrication and testing of fiber optic instrumentation for nanosensor interfacing.
Figure 18B:
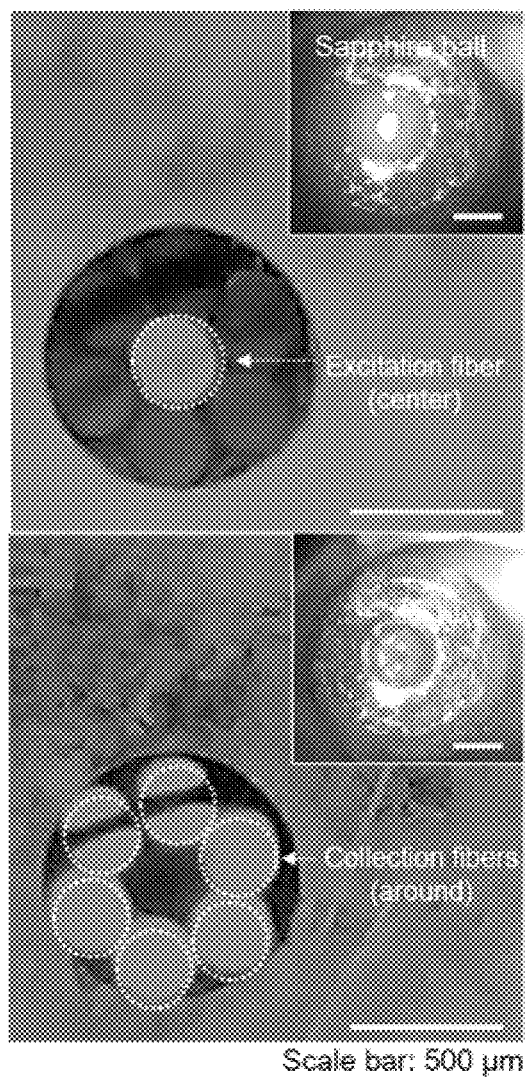
Figure 23A:
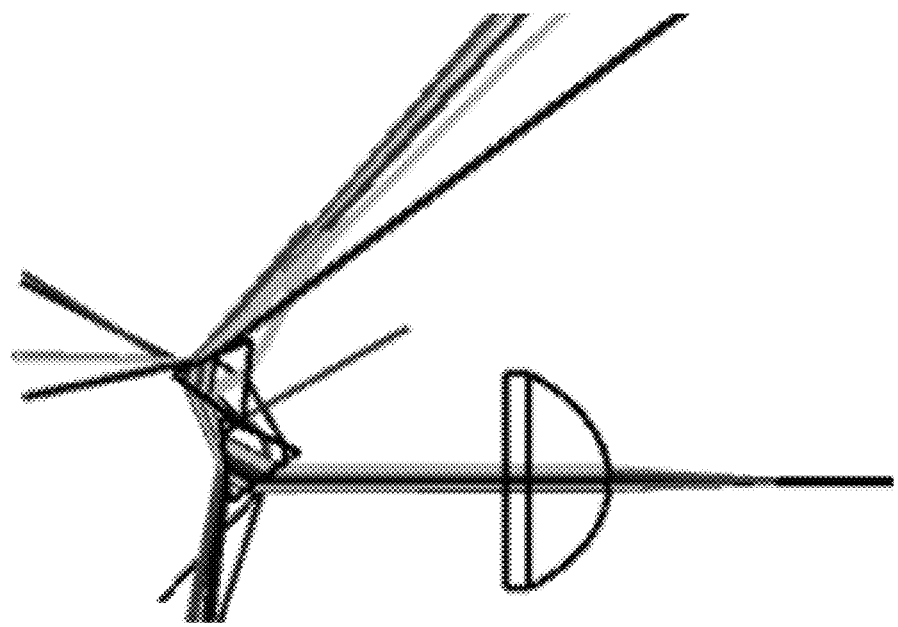
FIG. 23 depicts Zemax Optical Ray Tracing Simulations of coupling multiple light wavelengths between 550-850 nm via the use of 2 prisms to bring the various collimated beams into a single collimated beam that can be focused and launched into a fiber.
FIG. 23B depicts (left) Zemax Optical Ray Tracing Simulation of using a series of long pass dichroic mirrors (longer wavelengths [yellow] to shorter wavelengths [blue]), (Right) Schematic of the full fiber optic based optical system using long pass dichroic mirrors.
FIG. 23C depicts a schematic of the full fiber optic based optical system using multimode fiber optic couplers.
Figure 23B:
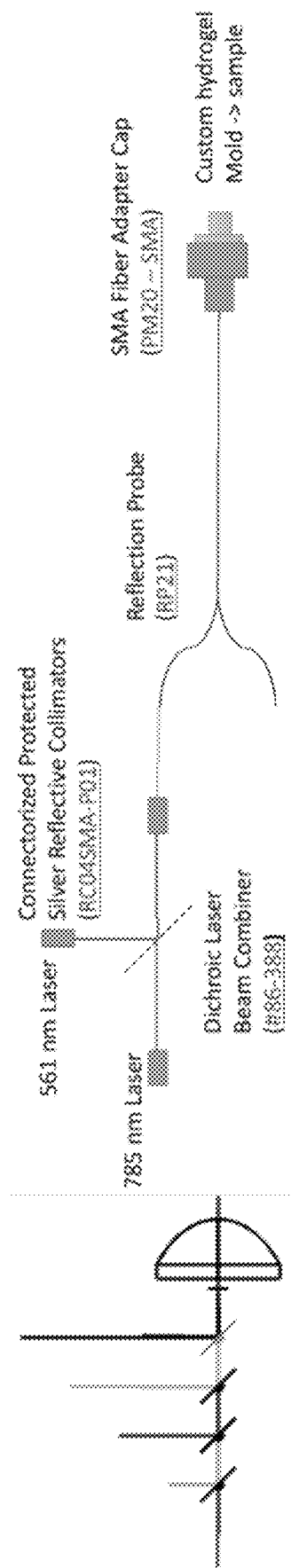
Figure 23C:
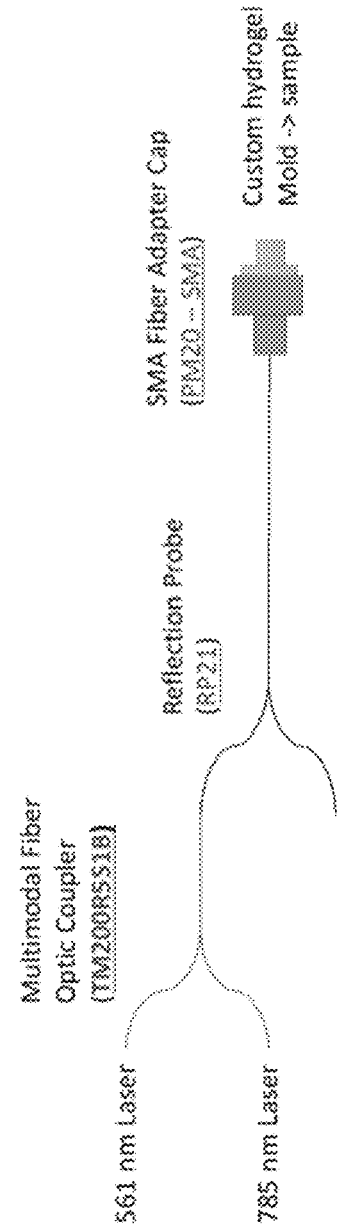

For step (1), the design of the optode fiber and associated instrumentation are illustrated in the schematics of FIG. 1A (which shows two similar set ups). The tool contains an optical fiber bundle coupled to dispersed nanosensors immobilized within a agarose hydrogel matrix. The hydrogel allows for direct immersion of the optode tip into complex liquid samples while maintaining the coupling to both excitation and the InGaAs amplified photodetector as collection. Fluorescent SWNT nanosensors were excited with both 561 nm and 785 nm laser with the ability of the system to be automatically switched depending on the chirality of the SWNT in the hydrogel (optical ray tracing simulations of coupling multiple light sources are shown in FIGS. 23A-23C). For example, 561 nm light is resonant with the band gap (the second gap $E_{22}$) of (6, 5) chirality, while 785 nm light is resonant with high-pressure carbon monoxide (HiPCO) SWNT including (10, 2), (9, 4), (8, 6), and (8, 7) chiralities. As described herein, a 561 nm laser was chosen for the fluorescence measurements. The schematic (top) and micrographs (bottom) of FIG. 18A shows the detailed configurations of the optode fibers for biochemical monitoring. The fiber optic probe is composed of a simple six-around-one fiber bundle where the central fiber provides the laser excitation for the SWNT nanosensors in hydrogel. The surrounding six fibers then collect the nIR fluorescence signal from the nanosensor element. Two different kinds of optode fibers were tested and used as part of this project. The first fiber is commercially available from Thorlabs, Inc. made up of bundles of multimode fibers but do not contain any end micro-optics (images, top). The second fiber is a custom-built fiber optic probe with end micro-optics fabricated as described in FIGS. 24A-29. The latter fiber was also made with six multimode optical fibers around a center multimode optical fiber (images, bottom). A sapphire half ball lens is added at the tip of the fiber bundles to improve the angle at which the fluorescence light from the center fiber illuminates the sensor element while at the same time increasing the collection angle of the anisotropic near infra-red fluorescence from the SWNT nanosensors. This custom-built fiber was specifically designed and fabricated to confirm whether the modified probe with end micro-optics end could improve nIR detection or not. Optical microscope images of the sensing tips of both commercial and custom-built fibers (insets, top-right) show that excitation and collection fibers were properly integrated with the appropriate light paths (FIG. 18B).

Figure 18C:
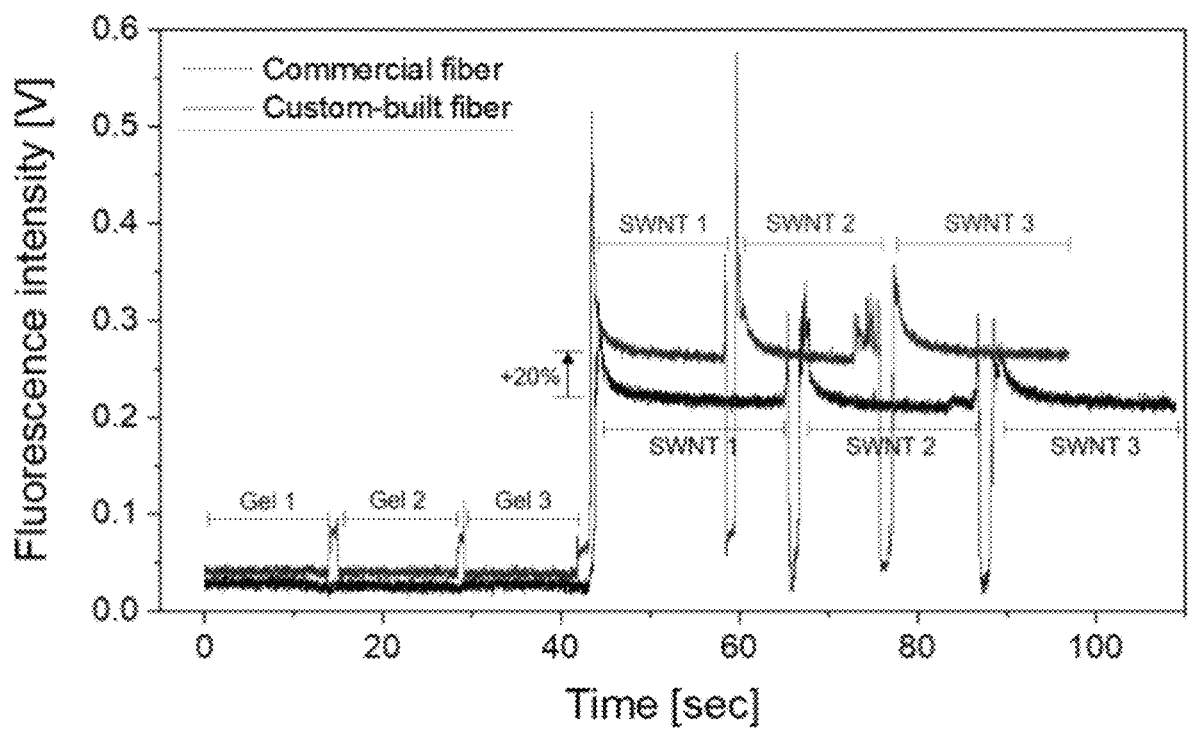

FIG. 1B shows images of the fully-integrated benchtop instrument for process monitoring. All components including the optode fiber, laser, nanosensors, nIR detectors, monitor, controller and test solutions are compactly integrated onto a benchtop mobile cart (depth 18", width 24", height 26-42"). In addition, the magnified image (right) shows that the optode fiber is flexible, lightweight, and robust enough such that the tip could be easily applied to reaction batches or process monitoring sites that would be difficult with conventional analytical tools. Finally, the fluorescence intensities of the commercial and custom-built optode fibers were compared (FIG. 18C)). The nIR monitoring tip of each optode fibers were moved well to well of 96-well plate with gel 1 to gel 3 for reference (without SWNT) and then moved to SWCNT 1 to SWCNT 3, where the difference between the intensities of SWCNT and gel corresponds to fluorescence intensity from SWCNT. It is clearly observed that reference gel wells without SWNT do not show any fluorescence signal while bright signal is observed with SWNT containing gel wells. Especially, the custom-built optode fiber improves the fluorescence intensity of SWNT within a 20% scale (from 0.21 to 0.25 V) due to effective fluorescence capture from the sapphire half ball lens on the tip. Thus, the optode fiber tip with micro-optics can definitely improve collection efficiency. However, since multiple fabrication steps are needed for the custom-built fiber version with micro-optics and the commercial probe is readily available at minimal cost (typically $418.14 at Thorlabs, Inc.), the commercial optode fiber is employed for the rest of this study.

To be cost effective and flexible as an optode fiber system, it may be more practical to employ lower quality lasers for excitation, due to their considerably lower price. But the resulting power fluctuations in time can compromise detection limits, as shown in the noisy signals of FIG. 18C.

Improvements in nanosensor performance cannot compensate for this, and the higher noise prevents at-line monitoring in an industrial setting. To address this, a parallel-measurement system that samples the real time delivered power in parallel to the optode fiber response has been developed. Nanosensor fluorescence intensity is ideally proportional to laser power, fluctuations in excitation necessarily lead to increase noise levels. See, for example, Paschotta, R. Noise in Laser Technology. *Opt. Photon.* 2009, 4, 48-50, which is incorporated by reference in its entirety. It is possible to cancel out the laser fluctuations by integrating a power meter as shown in inset of FIGS. 30A-30B. The signal can then be normalized as follows:

$$I(t) = \frac{I_{fluorescence}(t)}{I_{power\ meter}(t)/I_{power\ meter}(0)} \quad (1)$$

where fluorescence intensity is $I_{florescence}(t)$ and the measured power on the power meter is $I_{power-meter}(t)$. Note that the measured laser power is position dependent in this configuration. The baseline noise profile is significantly reduced from 4.47% to 1.2% level fluctuations (3.7-times improved) with the power meter monitoring systems. Accordingly, the measured power was normalized as read at the meter. It is clearly seen that baseline noise profile is significantly improved with this approach. Overall, the strategy described in step (1) above of fiber optic integration is successful.

Figure 2A:
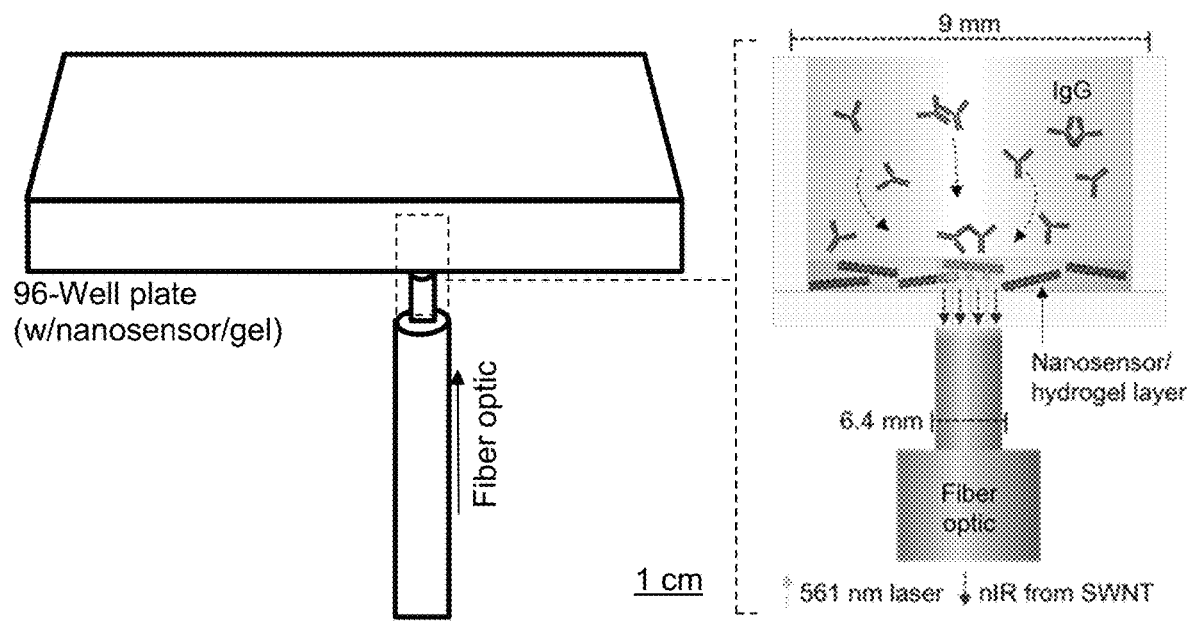
FIGS. 2A-2D depict sensor response to $IgG_1$ on 96-well plate as a model system.
Figure 19A:
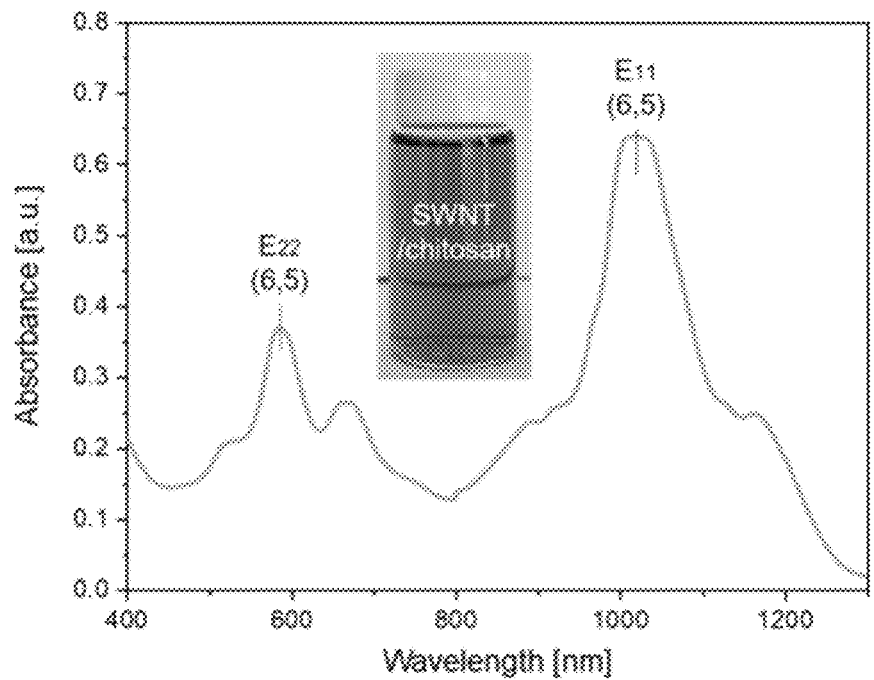
FIGS. 19A-19B show testing of the optode fiber with uncoupled system (96-well plate) collecting responses from nanosensor/hydrogel confirming successful excitation and emission collection.

The fully-integrated optode fiber instrument described herein can be used as an at-line form factor to detect biopharmaceutical aggregation and process impurities. As proof of concept, a 96-well plate with SWNT sensors immobilized in hydrogel was employed as an at-line measurement form factor for the uncoupled system since the plate allows users to prepare replicate samples producing measurements with consistent optics. FIG. 2A shows the image and schematic of the measurement configuration with this 96-well plate, nanosensor/hydrogel, and optode fiber. The nIR monitoring tip of the optode fiber was attached on the bottom surface of 96-well plate and collected the nIR signals from nanosensor. The SWNT transducers were immobilized in porous hydrogel matrix (0.2% agarose), which can efficiently modulate the selective diffusion of antibody proteins to SWNT layer, allowing us, in this example, to identify the presence of aggregate species through changes in the sensor response dynamics. In contrast to a sensor built on a chip substrate, the integration of a transducer on an optical fiber allows for remote testing with distance from target thus, the monitoring tip of optode fiber does not require precise focusing (FIGS. 31A-31F). Accordingly, the benchtop instrument allows for rapid prototyping with minimal training. Protein A-modified fluorescence SWNT (purified (6, 5) chiralities provided by Chasm Advanced Materials (CHASM)) with chitosan functionalization were exploited as transducer for IgG aggregation monitoring with optode fiber. To pre-attach the protein A on the SWNT/chitosan nanosensors, Cu-Nα,Nα-Bis(carboxymethyl)-L-lysine hydrate (Cu-NTA) was covalently bonded with carboxylic acid groups of chitosan functionalized SWNT surfaces (detail synthesis mechanism of nanosensor is described in Methods part). UV-Vis-nIR absorbance spectrum of the nanosensor dispersion clearly shows the significant $E_{22}$ (6, 5) and $E_{11}$ (6, 5) absorbance peaks at 584 nm and 1014 nm, respectively, indicating that SWNT surfaces were well functionalized with chitosan chemistry and dispersed in solution phase (FIG. 19A, inset: image of the nanosensor dispersion). See, for example, Nelson, J. T.; Kim, S.; Reuel, N. F.; Salem, D. P.; Bisker, G.; Landry, M. P.; Kruss, S.; Barone, P. W; Kwak, S.; Strano, M. S. Mechanism of Immobilized Protein A Binding to Immunoglobulin G on Nanosensor Array Surfaces. *Anal. Chem.* 2015, 87, 8186-8193, which is incorporated by reference in its entirety.

Figure 5A:
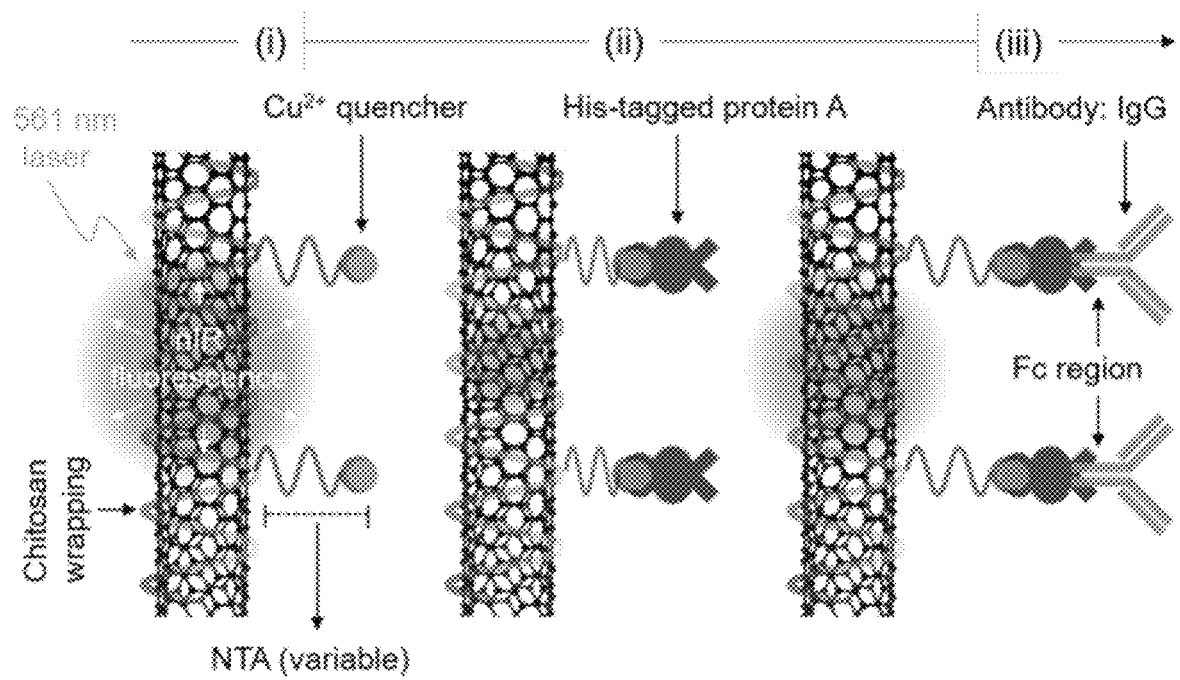
FIGS. 5A-5E depict sensors, systems and their properties.
Figure 19B:
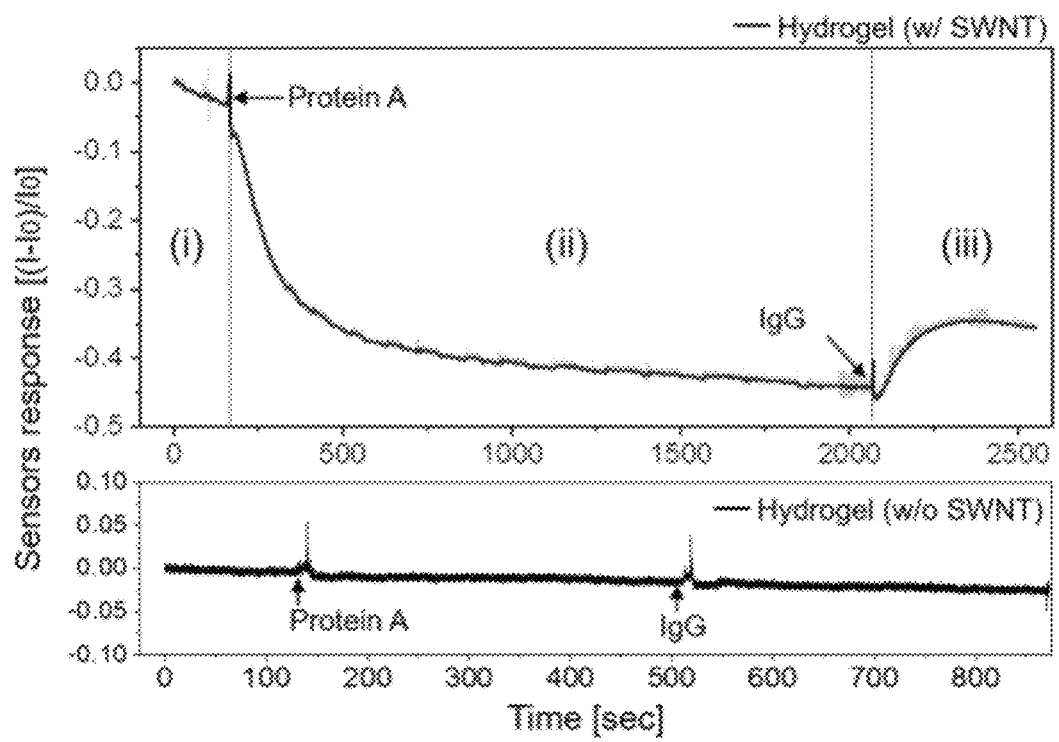
Figure 32A:
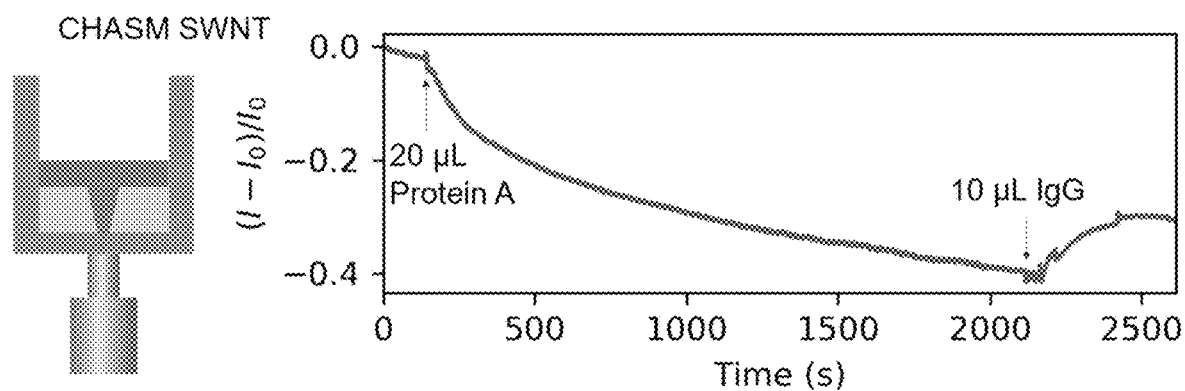
FIGS. 32A-32C shows real-time fluorescence monitoring of (FIG. 32A) purified (6,5) chirality SWCNT (CHASM) and (FIG. 32B) HiPCO loading protein A showing sensor responses to 10 mg/mL unstressed human IgG. Fluorescence time-trace of (FIG. 32C) negative control sample, which no SWNT sensors were diffused in agarose hydrogel.
Figure 32B:
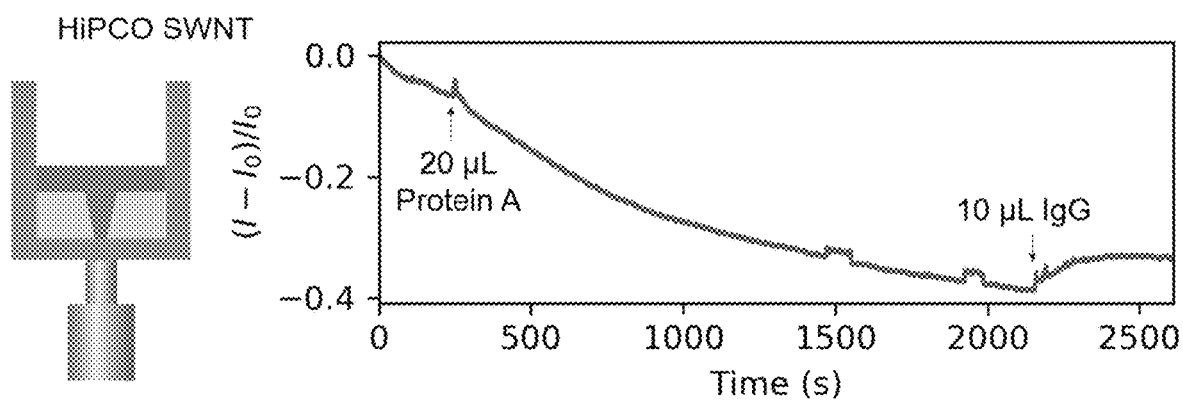
Figure 32C:
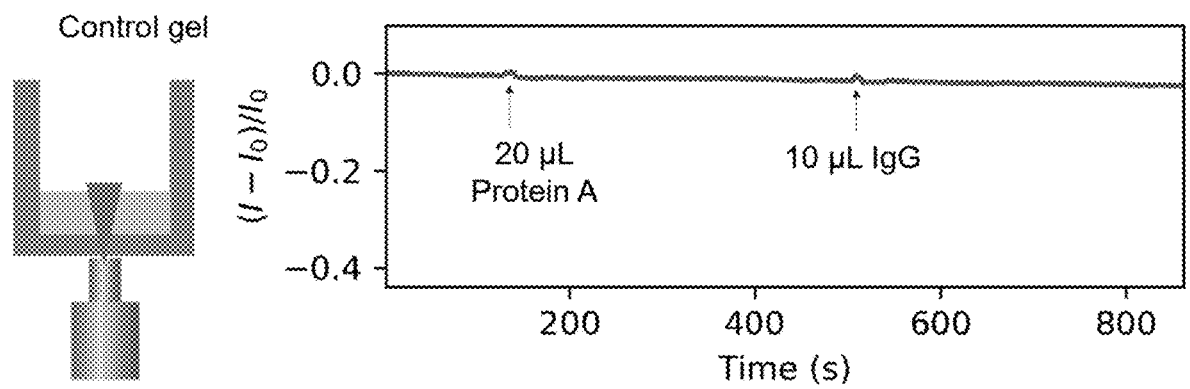
Figure 33:
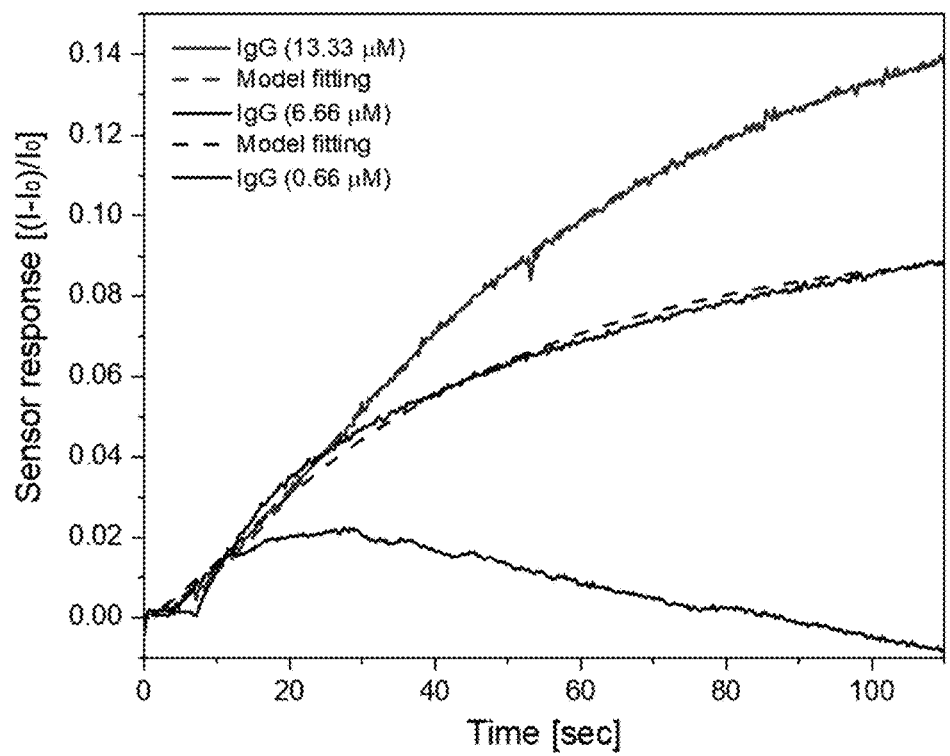
FIG. 33 depicts optode fiber monitoring of different concentration of IgG (2 mg/mL (13.33 μM), 1 mg/mL (6.66 μM), 0.1 mg/mL (0.66 μM)). Solid lines are measured real-time fluorescence trace and dashed lines are fitting with the derived model.
Figure 34:
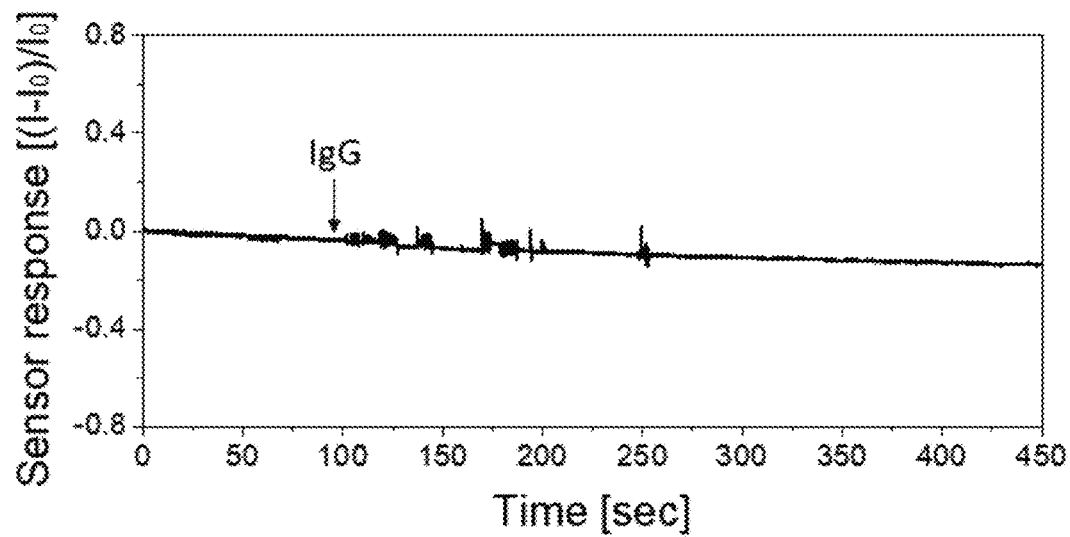
FIG. 34 depicts real-time fluorescence response of optode fiber onto IgG (10 μL, 10 mg/mL) injection without protein A. It is clearly seen that there are no any signal variations with IgG injection indicating that protein A is critical factor of IgG detection mechanism of the nanosensor layer.

The dynamic fluorescence response of the SWNT/chitosan nanosensors immobilized in hydrogel was measured during a single injection of protein A and IgG in series (FIG. 19B). The sensor response is defined as $R(t)=(I(t)-I_0)/I_0$, where $I_0$ is the initial fluorescence intensity and $I(t)$ is the fluorescence intensity at time t. Nanosensor response from optode fiber showed nIR quenching response with protein A injection and drastically recovered to 65% level of original fluorescence intensity with following IgG (10 μL of 10 mg/mL) injection. The hydrogel without SWNT nanosensor didn't show any fluorescence response to protein A and IgG injection indicating that signal is not from any additional sources such as mechanical deformation of gel or liquid flowing effect (bottom graph of FIG. 19B). These dynamic responses are consistent with previous measurement in a conventional nIR fluorescence instrument. See, for example, Nelson, J. T.; Kim, S.; Reuel, N. F.; Salem, D. P.; Bisker, G.; Landry, M. P.; Kruss, S.; Barone, P. W; Kwak, S.; Strano, M. S. Mechanism of Immobilized Protein A Binding to Immunoglobulin G on Nanosensor Array Surfaces. *Anal. Chem.* 2015, 87, 8186-8193; and Salem, D. P.; Gong, X.; Lee, H.; Zeng, A.; Xue, G.; Schacherl, J.; Gibson, S.; Strano, M. S. Characterization of Protein Aggregation Using Hydrogel-Encapsulated nIR Fluorescent Nanoparticle Sensors. *ACS Sens.* 2020, 5, 327-337, each of which is incorporated by reference in its entirety. In addition, the optode fiber showed consistent IgG detecting response even with various kind of SWNT chiralities (CHASM (6, 5) and HiPCO (10, 2), (9, 4), (8, 6), and (8, 7)) indicating that the fiber optic platform can be applied to various fluorescence measurement with high reliabilities (FIGS. 32A-32C). Various concentrations of IgG samples were monitored with the optode fiber nanosensor and limit of detection was determined to be around below 660 nM, which is almost identical with the conventional offline IgG monitoring performances (FIG. 33). See, Id. Overall, these measurements show the capability of observing fluorescence change of nanosensors using the optode fiber system with excitation and collection optics. Schematics of FIG. 5A depicts the detail mechanisms of the nIR fluorescence quenching and turn-on responses of SWNT/chitosan nanosensors in hydrogel. See, for example, Ray, A.; Bristow, T.; Whitmore, C.; Mosely, J. On-Line Reaction Monitoring by Mass Spectrometry, Modern Approaches for the Analysis of Chemical Reactions. *J. Mass Spec Rev.* 2018, 37, 565-579; and Salem, D. P.; Gong, X.; Lee, H.; Zeng, A.; Xue, G.; Schacherl, J.; Gibson, S.; Strano, M. S. Characterization of Protein Aggregation Using Hydrogel-Encapsulated nIR Fluorescent Nanoparticle Sensors. *ACS Sens.* 2020, 5, 327-337, each of which is incorporated by reference in its entirety. At the initial state (i), Cu-NTA is covalently bonded with carboxylic acid groups of chitosan surface of SWNT as described earlier, and the $Cu^{2+}$ ion of Cu-NTA works as a proximity quencher of SWNT fluorescence. His-tagged protein A appears to be bound to Cu-NTA and results change in intermolecular distance between SWNT and the $Cu^{2+}$, leading to the quenching response of nIR signals (state (ii)). Finally, when test solutions are injected onto nanosensor/hydrogel layers, IgG is bound to protein A with strong affinity to the fragment crystallizable (Fc) region of IgG. Then, the attached $Cu^{2+}$ quencher is pulled away from the SWNT surface and recover the fluorescence intensities leading to a drastic nIR turn-on response (state (iii)). In accordance with this, IgG injection without protein A does not show any fluorescence responses of optode fiber since IgG could not form Fc binding with protein A, which does not lead to quencher spacing variation (FIG. 34). Consequently, it is clearly demonstrated that the optode fiber interfaced nanosensor could be used for real-time monitoring of protein A and IgG chemical reactions.

Figure 20A:
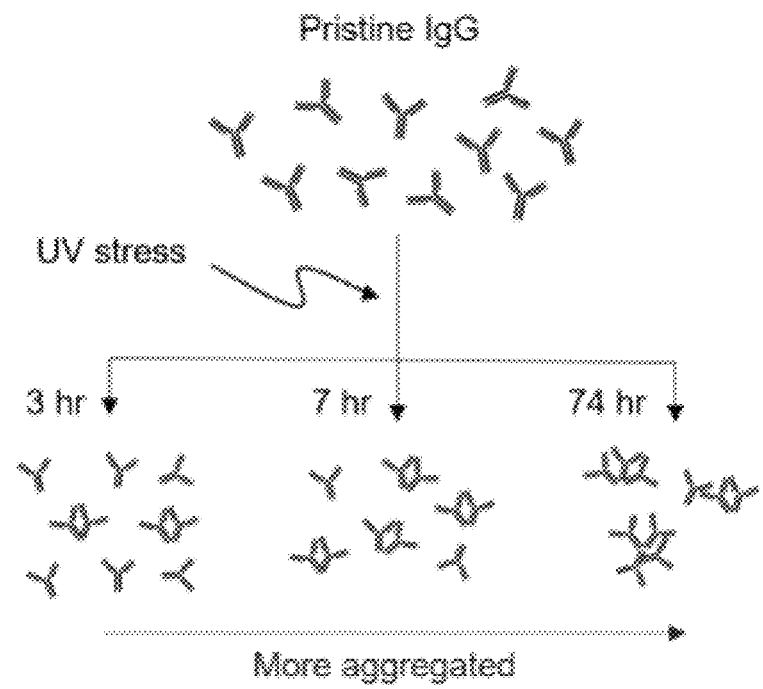
FIGS. 20A-20C show IgG aggregation monitoring performance of optode fiber with uncoupled system.
Figure 20B:
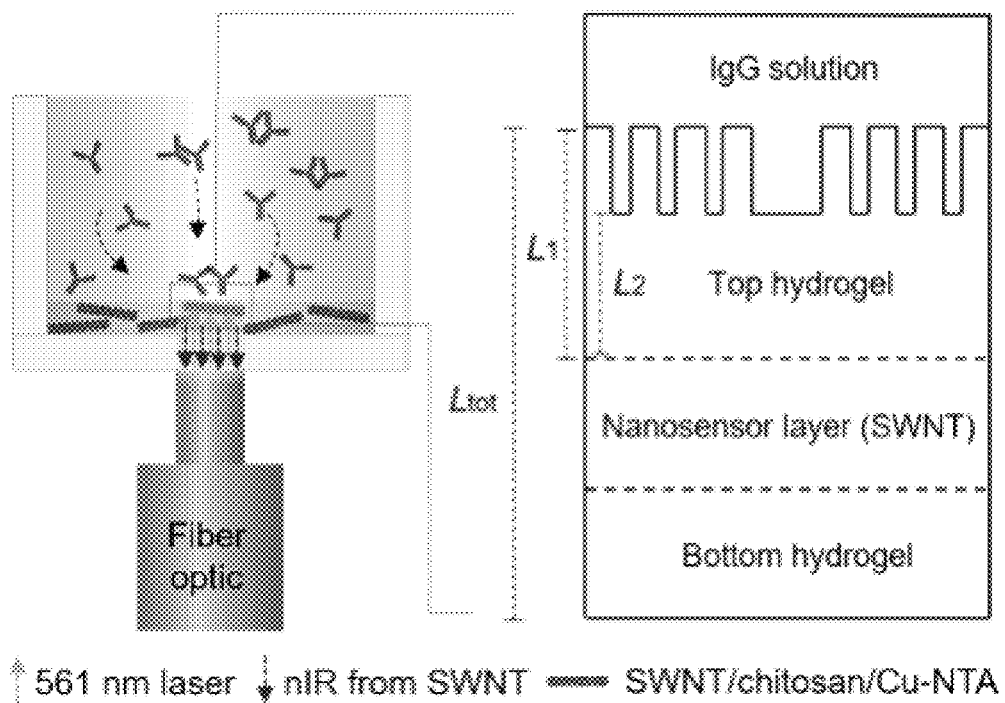
Figure 20C:
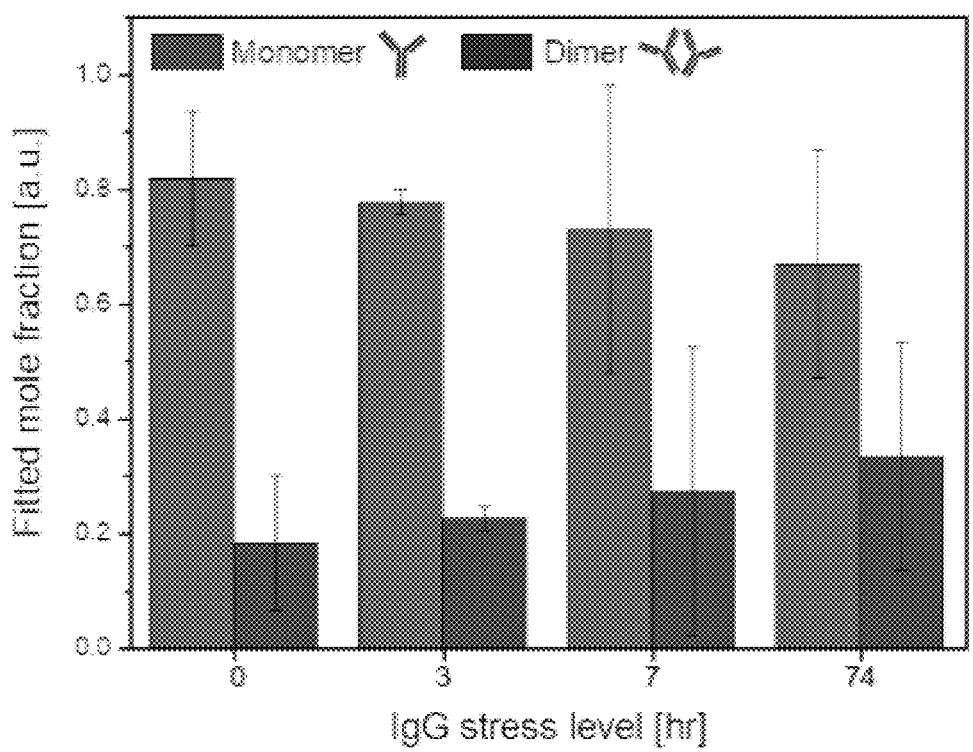
Figure 29:
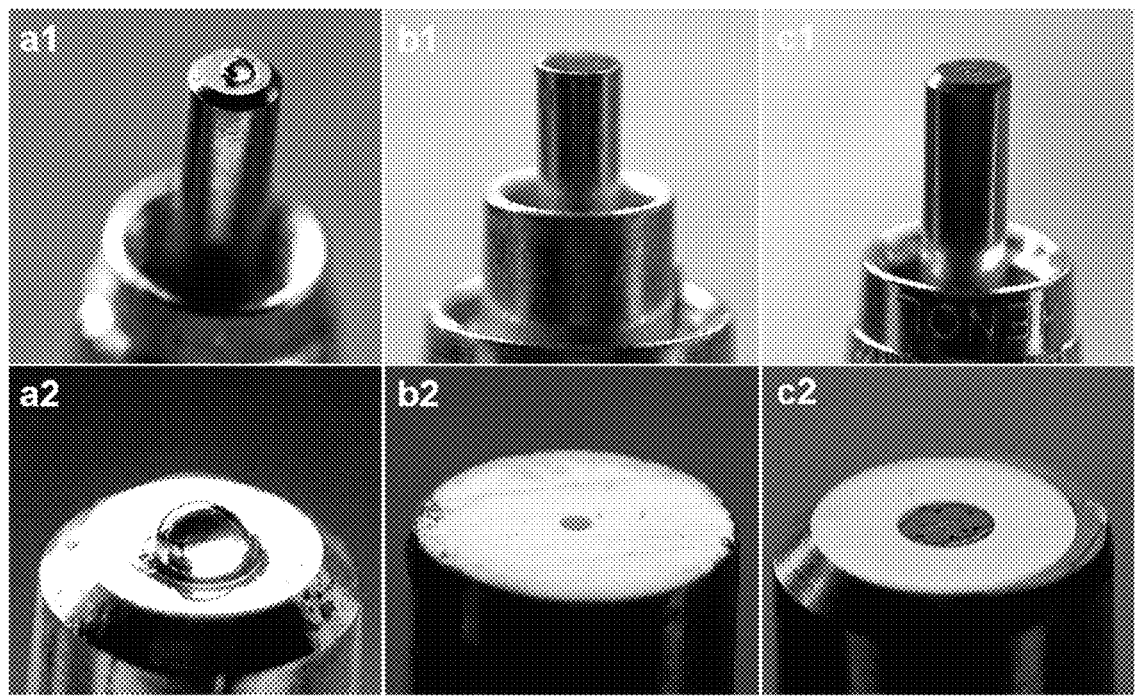
FIG. 29 depicts photo-images of the three fibers optic probe ends. Panel (a1) shows a probe end, panel (b1) shows central excitation fiber, and panel (c1) shows fluorescence collection fiber. Panels (a2, b2, c2) are magnified images of panels (a1, b1, c1).

Previous works demonstrated that higher portions of IgG were aggregated with higher exposure time of UV light since light exposure leads to photo-oxidations (FIG. 20A). See, for example, Shah, D. D.; Zhang, J. M.; Maity, H.; Mallela, K. M. G. Effect of Photo-Degradation on the Structure, Stability, Aggregation, and Function of an $IgG_1$ Monoclonal Antibody. *Int. J. Pharmaceut.* 2018, 547, 438-449; and Lorenz, C. M.; Wolk, B. M.; Quan, C. P.; Alcala, E. W.; Eng, M.; McDonald, D. J.; Matthews, T. C. The Effect of Low Intensity Ultraviole C Light on Monoclonal Antibodies. *Biotechnol. Progr.* 2009, 25, 476-482, each of which is incorporated by reference in its entirety. A multiphase hydrogel diffusion model was adapted to predict the response of the optode fiber with nanosensor and precisely analyze the IgG aggregation status. The setup of the problem follows the mathematical diffusion model developed previously. See, for example, Liang, S. M.; Xu, J.; Weng, L. H.; Dai, H. J.; Zhang, X. L.; Zhang, L. N. Protein Diffusion in Agarose Hydrogel In Situ Measured by Improved Refractive Index Method. *J. Controlled Release* 2006, 115, 189-196; and rank, J. *The Mathematics of Diffusion,* 2nd ed.; Clarendon Press: Oxford, 1979, each of which is incorporated by reference in its entirety. The development below allows us to quantitatively describe the turn-on response of SWNT nanosensors embedded into a multiphase hydrogel on the end of optode fiber upon addition of IgG. The diffusion model consists of SWNT immobilized in agarose hydrogel layer with two thickness: (i) thickness $L_1$ from the top surface of hydrogel to sensor layer and (ii) thickness $L_2$ from lower top surface of hydrogel to sensor layer that accounts for cracks within the hydrogel layer formed during casting and/or heterogeneity in the hydrogel thickness (FIG. 20B). Then, the total concentration profile in two diffusion model with time scale could be expressed as following equation.

$$C_T(t) = \alpha_{MP} C_0 \left[\beta \frac{C_{MP}(L_1, t)}{C_0} + (1-\beta) \frac{C_{MP}(L_2, t)}{C_0}\right] + \alpha_{HMW} C_0 \left[\beta \frac{C_{HMW}(L_1, t)}{C_0} + (1-\beta) \frac{C_{HMW}(L_2, t)}{C_0}\right] \quad (2)$$

where the mass fractions of monomer ($\alpha_{MP}$) and high molecular weight (HMW) IgG ($\alpha_{HMW}$) to total IgG weight, the smaller ($L_1$) and the ratio of the thick hydrogel layer ($\beta$) (detail model derivation in FIG. 29). The HMW species were assumed as dimers for the model and the hydrodynamic radii were approximated as 5.6 nm and 9.6 nm for monomer and HMW species, respectively with statistics on previously reported works. See, for example, Salem, D. P.; Gong, X.; Lee, H.; Zeng, A.; Xue, G.; Schacherl, J.; Gibson, S.; Strano, M. S. Characterization of Protein Aggregation Using Hydrogel-Encapsulated nIR Fluorescent Nanoparticle Sensors. *ACS Sens.* 2020, 5, 327-337; Amsden, B. Solute Diffusion within Hydrogels. Mechanisms and Models. *Macromolecules* 1998, 31, 8382-8395; and Pluen, A.; Netti, P. A.; Jain, R. K.; Berk, D. A. Diffusion of Macromolecules in Agarose Gels: Comparison of Linear and Globular Configurations. *Biophys. J.* 1999, 77, 542-552, each of which is incorporated by reference in its entirety. First of all, it is clearly seen that all the measured data were well fitted with expected dynamics with equation (2) having mean $R^2$ value of near 1 (0.9990, 0.9989, 0.9968, and 0.9944 for 0, 3, 7, and 74 hr, respectively). More importantly, it is clearly observed that the averaged am decreases (0.82, 0.77, 0.72, 0.66) and $\alpha_{HMW}$ increases (0.18, 0.22, 0.27, 0.33) with the longer UV exposure time since IgG is aggregated into high molecular weight drastically as expected (FIG. 20C). This monomer and aggregated dimer ratio extracted by the optode fiber system showed almost similar tendency with the ratio confirmed by size-exclusion ultra-high-performance liquid chromatography (SE-UPLC). Overall, it is clearly demonstrated that the optode fiber benchtop instrument with nanosensor interfacing successfully differentiated the various aggregation levels of IgG with mathematical modelling. Previous diffusion model for offline IgG monitoring was identically applied on the system indicating that the fiber optics can be used as reliable form factor for interfacing nanosensor into the field-oriented applications. In addition, it is a strength to be able to fit the diffusion model to the uncoupled system, showing that no additional fitting of parameters is needed for the real coupled system showed at the end.

Figure 21A:
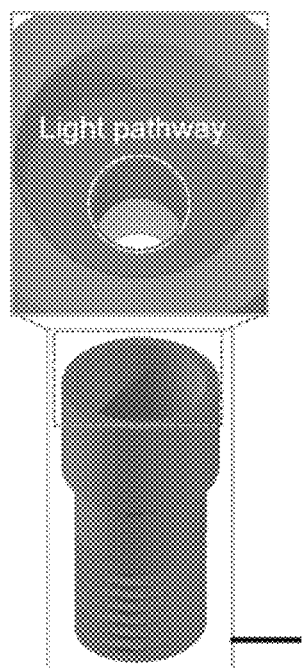
FIGS. 21A-21F show a fully-integrated lab-on-fiber protein monitoring system coupled with 3D-printed miniaturized sensor tip.

Indeed, the microscopic cross-section and high-aspect-ratio combined with mechanical robustness and flexibility make the optode fiber unrivaled candidates for lab-on-fiber technology. See, for example, Ricciardi, A.; Crescitelli, A.; Vaiano, P.; Quero, G.; Consales, M.; Pisco, M.; Esposito, E.; Cusano, A. Lab-On-Fiber Technology: A New Vision for Chemical and Biological Sensing. *Analyst* 2015, 140, 8068-8079; and Kostovski, G.; Stoddar, P. R.; Mitchell, A. The Optical Fiber Tip: An Inherently Light-Coupled Microscopic Platform for Micro- and Nanotechnologies. *Adv. Mater.* 2014, 26, 3798-3820, each of which is incorporated by reference in its entirety. The sensing tip of optode fiber could be easily applied on various shape/type of chemical reaction batches or fluorescent monitoring sites. Accordingly, it could efficiently be applied to a small form factor for at-line monitoring of biopharmaceutical industry. See, for example, Ricciardi, A.; Crescitelli, A.; Vaiano, P.; Quero, G.; Consales, M.; Pisco, M.; Esposito, E.; Cusano, A. Lab-On-Fiber Technology: A New Vision for Chemical and Biological Sensing. *Analyst* 2015, 140, 8068-8079, which is incorporated by reference in its entirety. In order to demonstrate the lab-on-fiber with the optode fiber benchtop instrument, three-dimensional (3D) miniaturized sensor tip was designed and fabricated. FIG. 21A shows the computer-aided design (CAD) of miniaturized sensor tip. The design is with 7 mm scale miniaturized circular chamber for holding nanosensor/hydrogel layer and screw shaped pillar, which allows mold to be integrated with end of the optode fiber. In addition, 3.5 mm size hole is in the center of sensor tip, which allows excitation light to directly touch the nanosensor/hydrogel and collect the fluorescence signal sensitively. Accordingly, the probes end of the fiber do not physically contact the SWNT/hydrogel layers indicating that surface of the probe ends could be protected from any chemical contamination and fouling problems. The sensor tips were printed by a 3D-printer (Objet Prime, Stratasys Ltd) using methacrylate photopolymers and cured in UV light at a 60° C. controlled temperature. After 3D-printing, the printed molds were washed in isopropyl alcohol (IPA) to remove residual resin overnight. Hydrodynamics of nanosensor layer in the sensing tip were identical with an uncoupled system.. Consequently, it is clearly shown that the optode fiber could be efficiently applied to lab-on-fiber technology with sensor tip for protein aggregation monitoring.

Figure 21B:
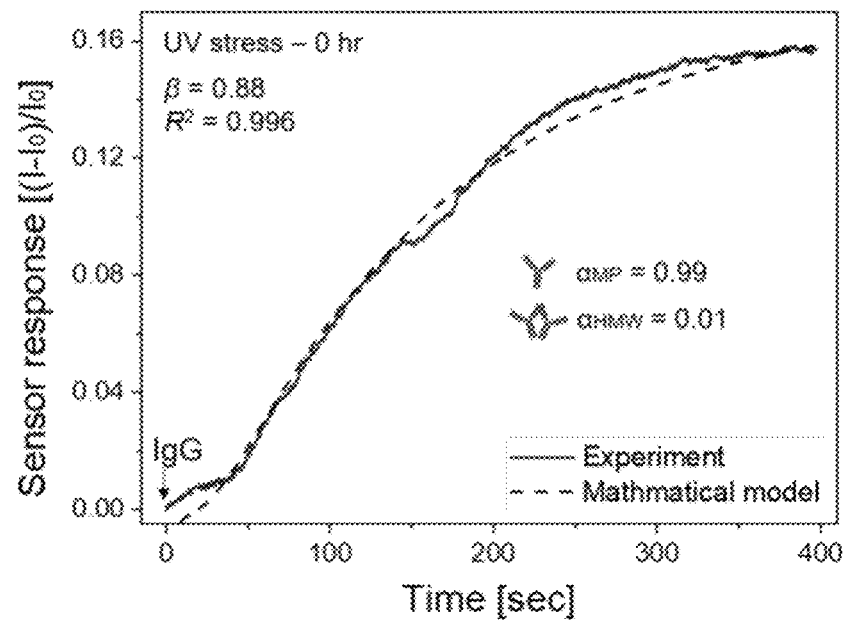
Figure 21C:
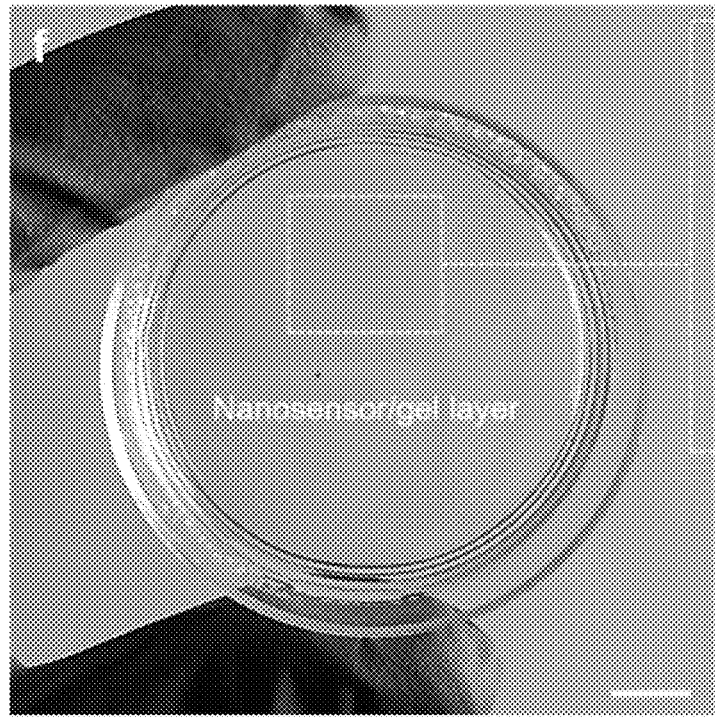
Figure 21D:
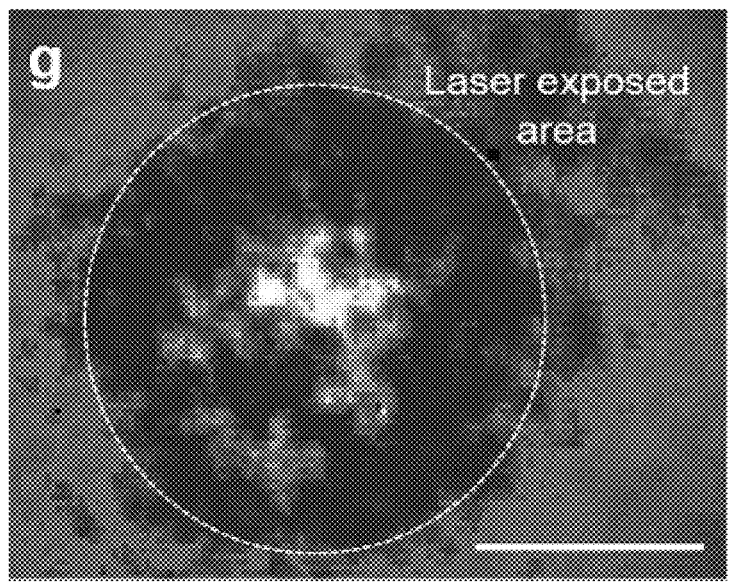
Figure 21E:
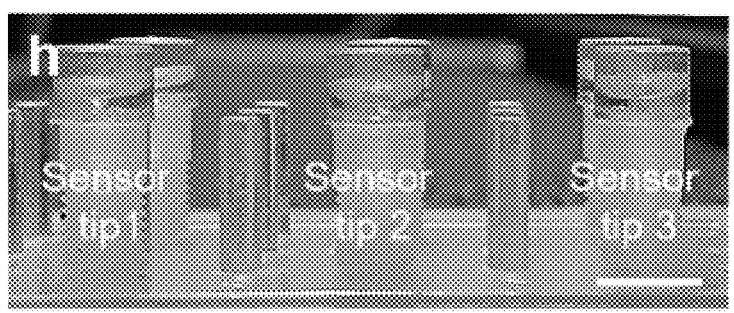
Figure 35:
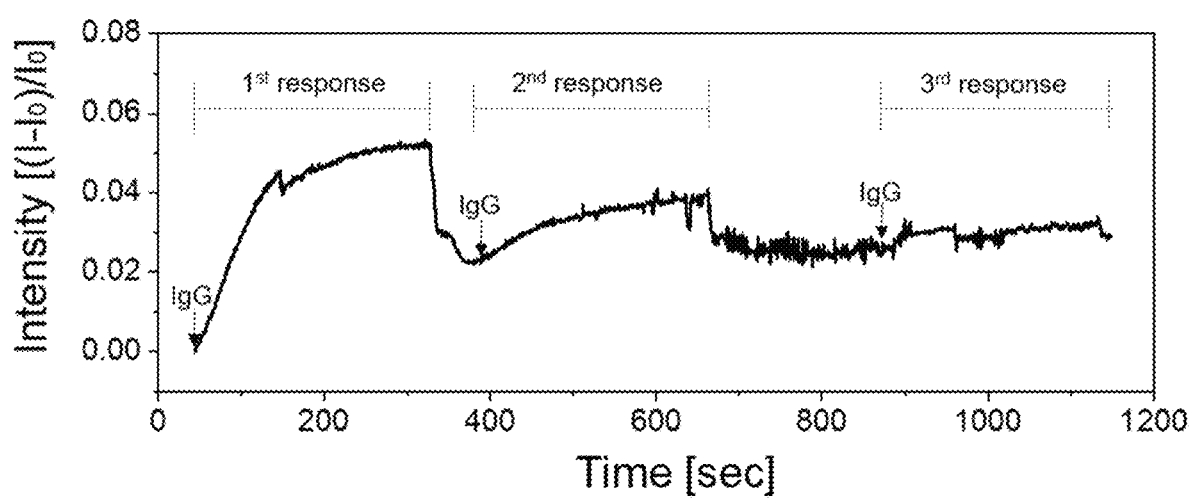
FIG. 35 depicts maximum measurement counts of single 3D sensing tip. Sensor response to 10 μL of 10 mg/mL IgG with the SWNT sensor diffused in 0.2% agarose hydrogel. The black arrows indicate the addition of IgG, showing the increased fluorescent signal twice.

In addition, strong nIR signals were clearly measured from whole exposed area of SWNT/hydrogel layer with excitation laser, indicating that multiple sensing tips having reliable fluorescent properties could be easily prepared by mass production of nanosensor/hydrogel components (FIG. 21D). Considering the size of the miniaturized sensor tip, theoretically maximum 61 sensor tips could be prepared with just single time synthesis of SWNT/hydrogel on 5.5 cm scale petri dish. Accordingly, users can easily conduct protein/drug status measurement just by changing the sensor tip of optode fiber with a previously fabricated new tip, which is real applications for online and at-line lab-on-fiber technology. In order to investigate the maximum measurement counts of single sensor tip, SWNT/hydrogel sensor response to three repetitive IgG injection was measured (FIG. 35). It is observed that optode fiber response became slightly smaller for second injection of IgG, and finally saturated with third injection of IgG. This might be due to fact that excess amount of IgG may get stacked at nanopores of hydrogel. Thus, the disposable single sensor tip can be used for twice of measurement and then replaced with new sensor tip.

Figure 21F:
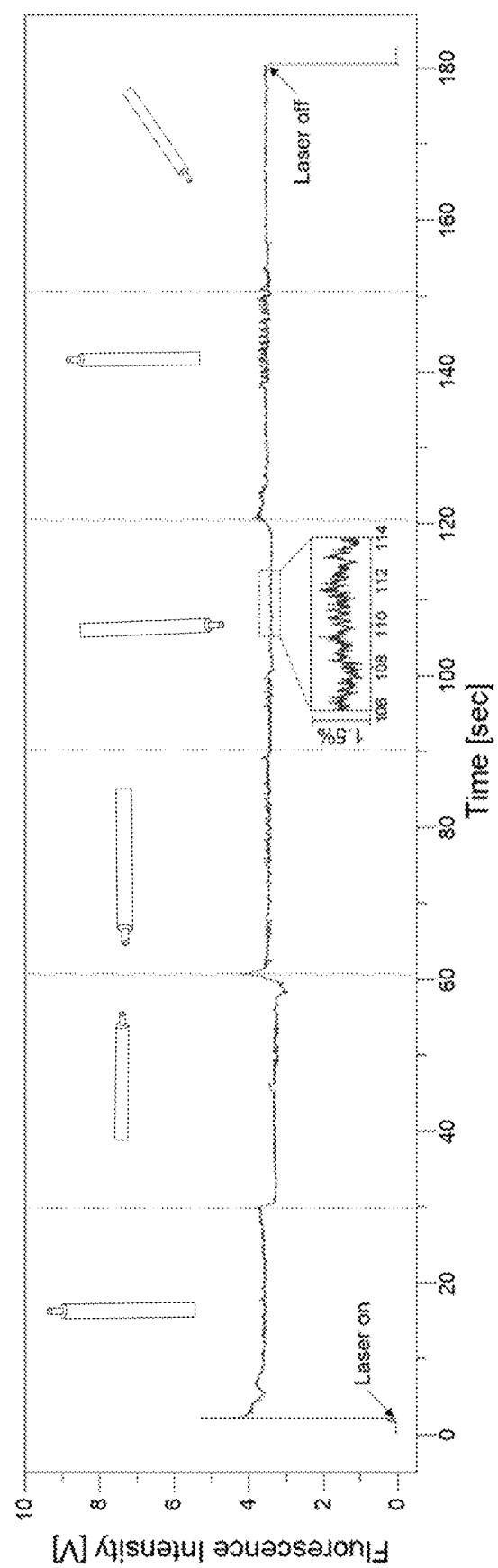

Finally, to investigate the mechanical robustness and flexibility of the fully-integrated lab-on-fiber system, the real-time nIR baseline was continuously measured during simultaneous fiber deformation into various shapes (FIG. 21F). After laser turn-on, a ~3.4 V level baseline from the nIR signal and the sensor tip was stably observed for at least a few minutes without baseline drift or noise. Thereafter, the baseline remained stable even after continuous mechanical deformation of the optode fiber. The tip design and adhesion can be adequately integrated with the end of the optode fiber. Hence, the fully-integrated lab-on-fiber system has potential for direct application to biopharmaceutical processing environments.

Figure 22A:
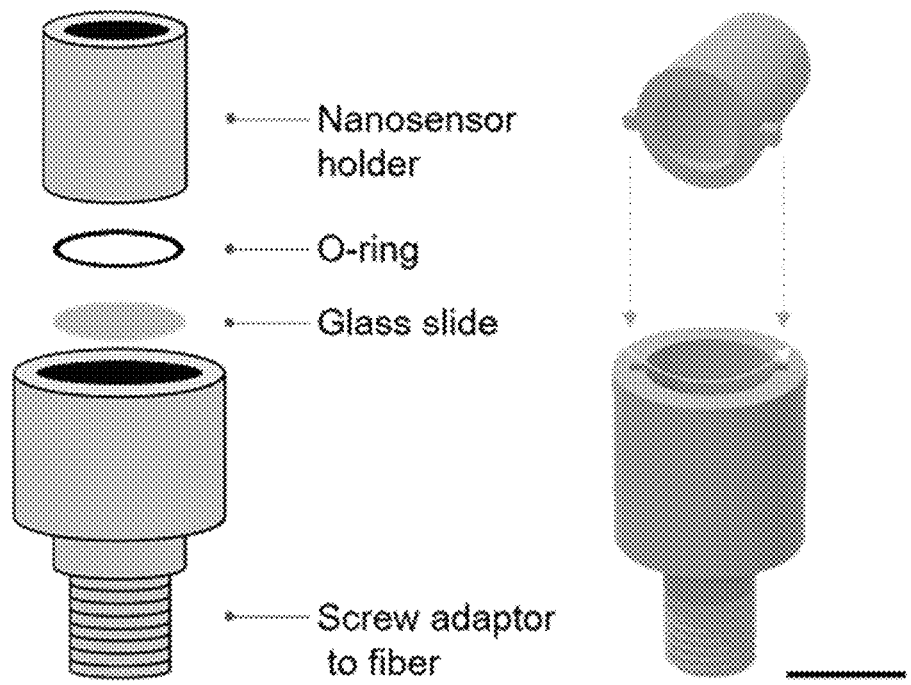
FIGS. 22A-22I show the extension of the optode fiber to other bioanalytes of interest, employing an alternate sensor tip design.
Figure 22B:
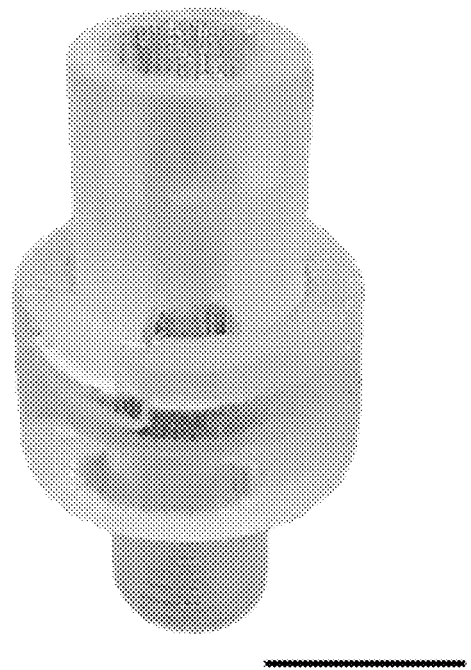
Figure 22C:
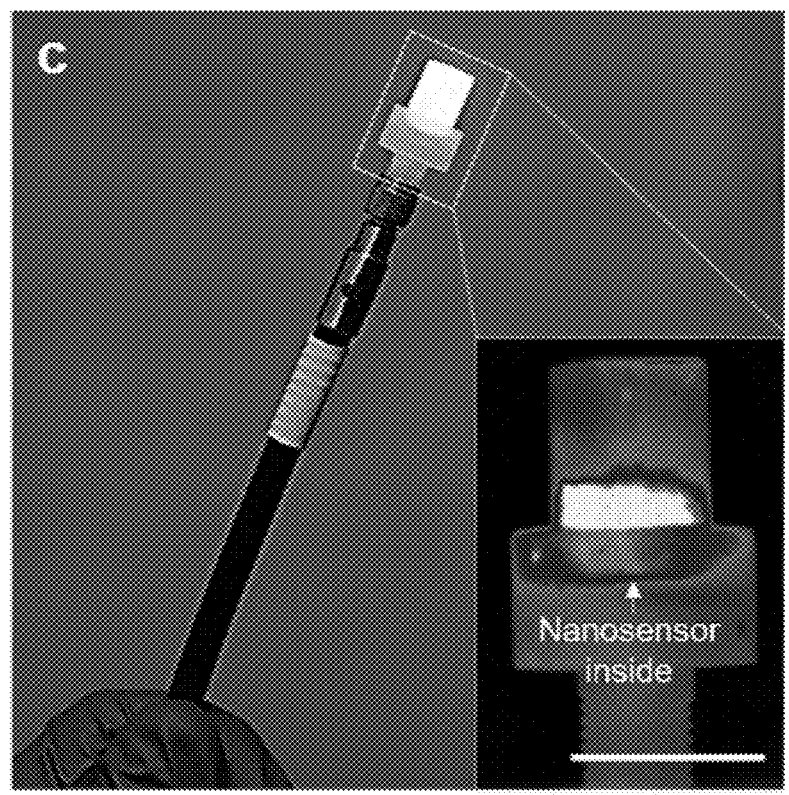
Figure 22D:
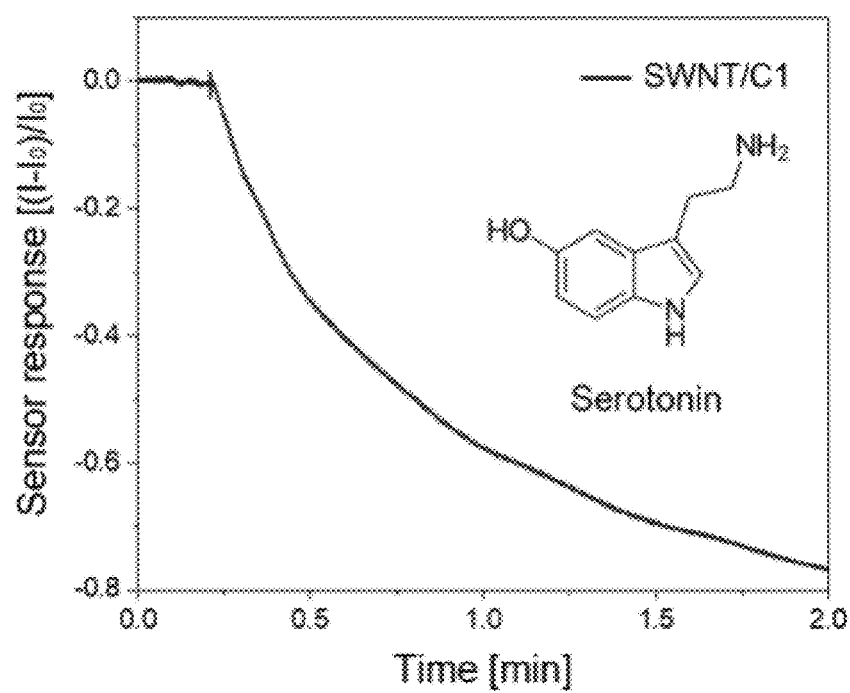
Figure 22E:
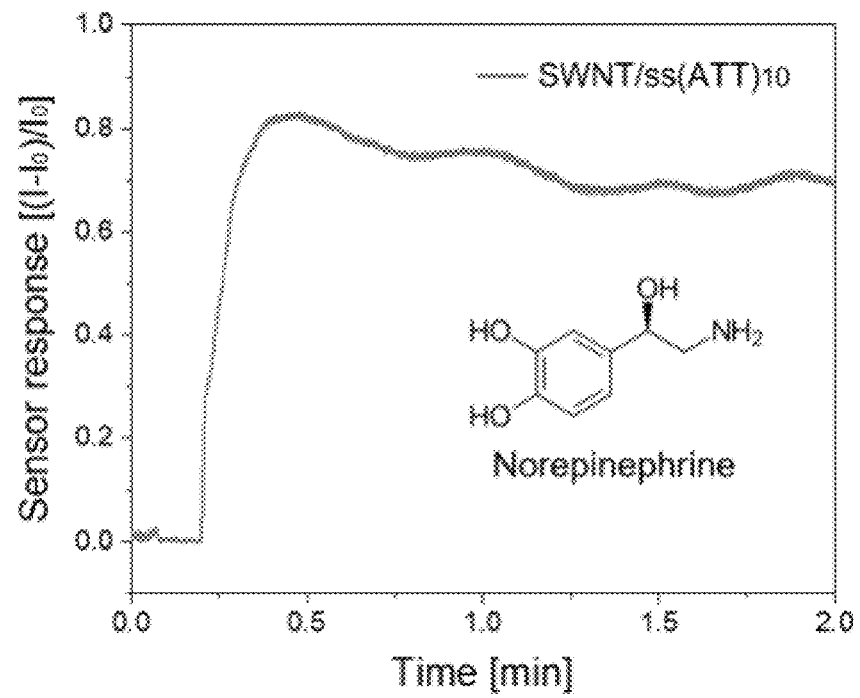
Figure 22F:
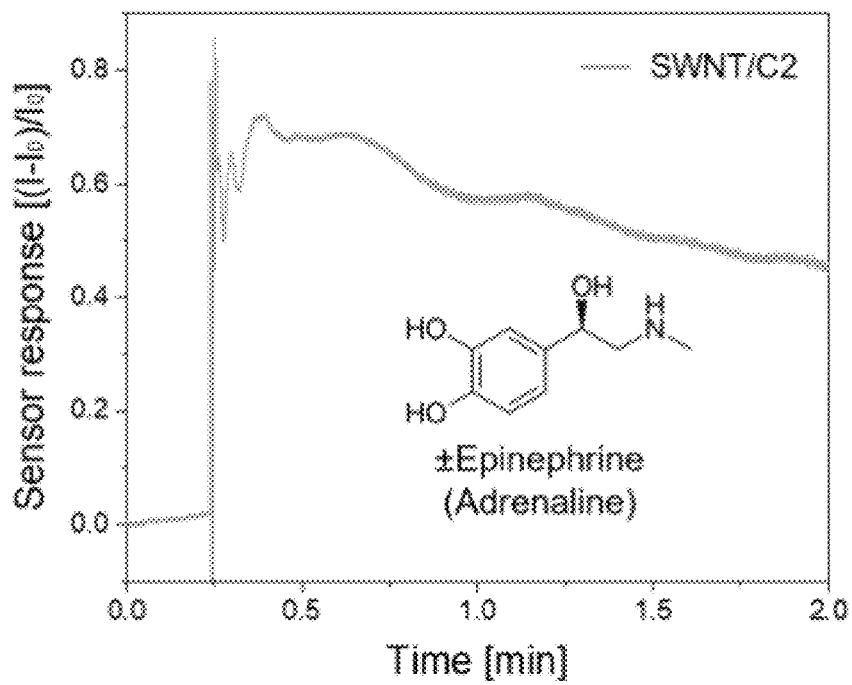
Figure 22G:
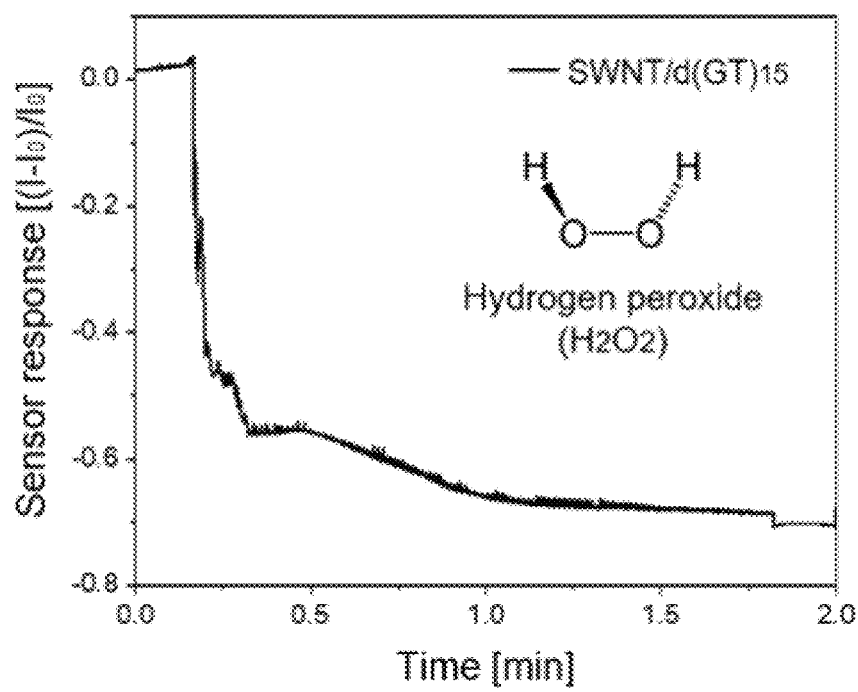
Figure 22H:
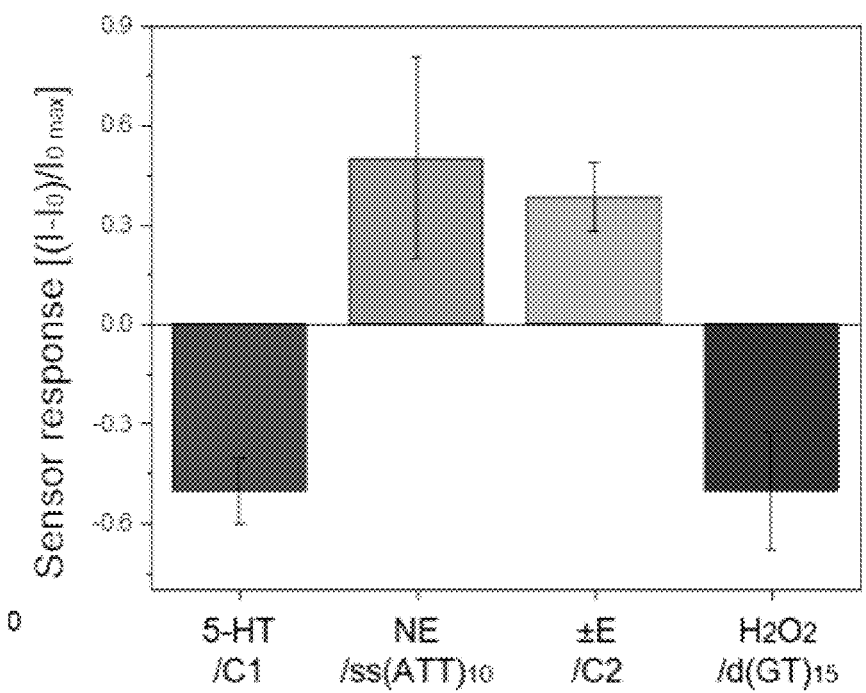

The platform can also be extended to the monitoring of other small molecule analytes. For this, alternate sensor tips were created with glass window integration for liquid phase monitoring of various solution phase bio-analytes (FIGS. 22A-22I). For the IgG aggregation monitoring, nanosensors were imbedded in hydrogel which can maintain their own shape, thus excitation laser could touch the bottom of sensor layer through the hole of the sensor tip without any slide window integration. To maximize versatility, the design should allow testing of small liquid volumes but result in stable nIR signals, even from media in the form of whole droplets. To realize this, an 8 mm-cover glass slide was compactly integrated between the nanosensor holder and the optode fiber adaptor using an O-ring (5 mm inside diameter, 8 mm outside diameter, 1.5-mm thick, Buna-N O-Ring, MSC #31958200), producing a monitoring window (left schematic of FIG. 22A). After putting the glass window and O-ring in series on the printed screw adaptor, the nanosensor holder can be pushed and rotated to perfectly remove all leaking points in the sensor tip (right CAD of FIG. 22A). The photo- and nIR images show the nanosensor phase with in the glass window interfaced tip produced by the design (FIGS. 22B-22C). The result is a lab-on-fiber system easily extended to biochemical analytes monitoring.

To test whether the fiber optic nanosensor is extendable to other analytes of interest, serotonin (5-HT), norepinephrine (NE), adrenaline (±epinephrine; ±E), and hydrogen peroxide ($H_2O_2$) were tested, monitoring the dynamic response of each upon addition. For this, nanosensors modified as described previously using corona phase molecular recognition (CoPhMoRe) were used to create selective interfaces for target bioanalytes. See, for example, Zhang, J. Q.; Landry, M. P.; Barone, P. W.; Kim, J. H.; Lin, S. C.; Ulissi, Z. W.; Lin, D. H.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D. Y.; et al. Molecular Recognition Using Corona Phase Complexes Made of Synthetic Polymers Adsorbed on Carbon Nanotubes. Nat. Nanotechnol. 2013, 8, 959-968 and Bisker, G.; Dong, J.; Park, H. D.; Iverson, N. M.; Ahn, J.; Nelson, J. T.; Landry, M. P.; Kruss, S.; Strano, M. S. Protein-Targeted Corona Phase Molecular Recognition. Nat. Commun. 2016, 7, 10241, each of which is incorporated by reference in its entirety. Specifically, DNA sequences including $((GT)_{15}$ GAT CTA AGG CGT GTAT) (e.g. C1), $ss(ATT)_{10}$, (AT-CAAGGCTCGAATTGTCCCTGAAATCT) (e.g. C2), and d(GT) is were utilized for selective monitoring of 5-HT, NE, ±E, and $H_2O_2$, respectively. These nanosensors produce turn on fluorescent responses for NE and E, and turn off responses for 5-HT and $H_2O_2$. See, for example, Zhang, J.; Boghossian, A. A.; Barone, P. W.; Rwei, A.; Kim, J.-H.; Lin, D.; Heller, D. A.; Hilmer, A. J.; Nair, N.; Reuel, N. F.; Strano, M. S. Single Molecule Detection of Nitric Oxide Enabled by d(AT) is DNA Adsorbed to Near Infrared Fluorescent Single-Walled Carbon Nanotubes. J. Am. Chem. Soc. 2011, 133, 567-581; and Jeong, S.; Yang, D.; Beyene, A. G.; Bonis-O'Donnell, J. T. D.; Gest, A. M. M.; Navarro, N.; Sun, X.; Landry, M. P. High-Throughput Evolution of Near-Infrared Serotonin Nanosensors. Sci. Adv. 2019, 5, eaay3771, each of which is incorporated by reference in its entirety. Real-time fluorescence measurements with the optode fiber show distinct turn-on or turn-off responses as applicable analytes within short times (2 min) with significantly high signal-to-noise ratio (~126.66 (5-HT)) (FIGS. 22D-22G). Distinct responses behavior of each bioanalytes were attributed to that specific DNA sequences and (n, m) SWNT chiralities of each nanosensors formed unique molecular interfaces leading to distinct location of highest-occupied molecular orbital (HOMO) and lowest-unoccupied molecular orbital (LUMO). See, for example, Zhang, J. Q.; Landry, M. P.; Barone, P. W.; Kim, J. H.; Lin, S. C.; Ulissi, Z. W.; Lin, D. H.; Mu, B.; Boghossian, A. A.; Hilmer, A. J.; Rwei, A.; Hinckley, A. C.; Kruss, S.; Shandell, M. A.; Nair, N.; Blake, S.; Sen, F.; Sen, S.; Croy, R. G.; Li, D. Y.; et al. Molecular Recognition Using Corona Phase Complexes Made of Synthetic Polymers Adsorbed on Carbon Nanotubes. Nat. Nanotechnol. 2013, 8, 959-968; and Salem, D. P.; Landry, M. P.; Bisker, G.; Ahn, J.; Kruss, S.; Strano, M. S. Chirality Dependent Corona Phase Molecular Recognition of DNA-Wrapped Carbon Nanotubes. Carbon 2016, 97, 147-153, each of which is incorporated by reference in its entirety. The maximum sensor response of each analyte for 2 min after exposure are presented in FIG. 22H. The platform is clearly capable of rapid analysis of these distinct bio-analytes with small analyte volume additions (5 μL at 1 mM) and short response times.

Figure 22I:
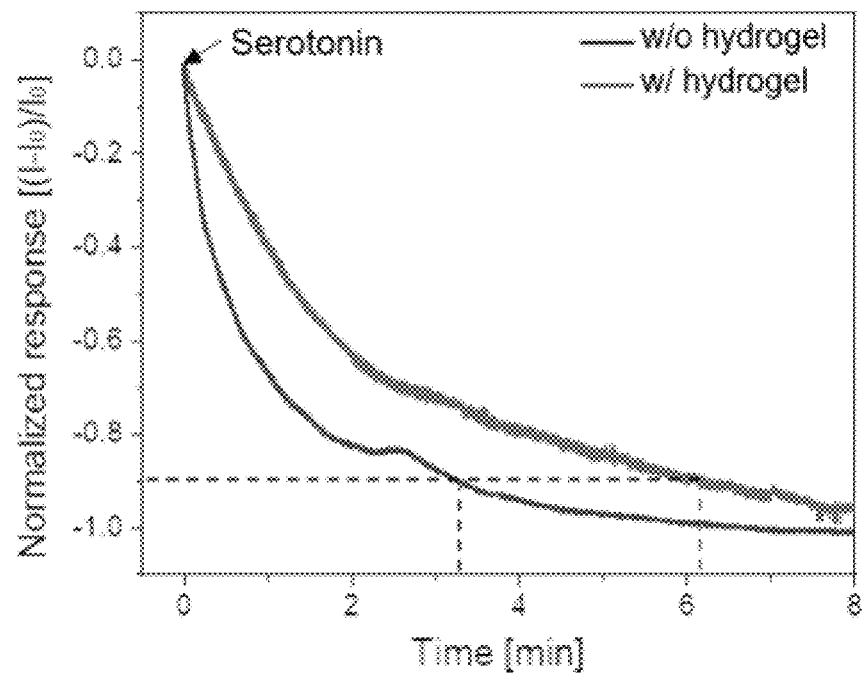

For monitoring these various bio-analytes, sensing tips were constructed for liquid phase nanosensor query without hydrogel immobilization. To measure the effect of the hydrogel tunable layer on small-molecule diffusion, 5-HT responses were compared with hydrogel and without hydrogel system (FIG. 22I). SWNT/ss(GT) nanosensor for 5-HT was immobilized in the identical conditions of IgG monitoring sensing tip with hydrogel (0.2% agarose, expected hydrogel thickness: 420 μm). In the absence of a hydrogel layer, 5-HT injection caused an immediate drop in the sensor signal and touched the 90% of saturation level within 3.1 min. However, the addition of the hydrogel layer causes a demonstrable time lag in the sensor response and a slowing of the response dynamics such that the sensor response level out only after several minutes. The time scale of the experiment in FIG. 22I is on the order of the diffusive time scale for a small molecule calculated via equation (3) below, assuming a hydrogel thickness of approximately 420 µm (from FIG. 21B) and diffusion coefficient in agarose gel of $10^{-5}$ cm$^2$/sec. See, for example, Lundberg, P.; Kuchel, P. W. Diffusion of Solutes in Agarose and Alginate Gels: 1H and 23Na PFGSE and 23Na TQF NMR Studies. *Magn. Reson. Med.* 1997, 37, 44-52, which is incorporated by reference in its entirety.

$$\tau_D = \frac{L^2}{D} \sim \frac{(420\ \mu m)^2}{1 \times 10^{-5}\ cm^2/s} = 176.4\ sec \quad (3)$$

Hence, the hydrogel thickness needs to be considered when considering the detection time required for process monitoring. Overall, the optode fiber system could be universally applied onto continuous and batch process monitoring of various biochemical analytes and wide range of nanosensors libraries.

As described herein, a fiber optic, benchtop instrument (optode) can be used for the interrogation of fluorescent nanosensors both online and at-line for process monitoring and in manufacturing settings. A compact, integrated fiber optic nanosensor element has been fabricated and the sensitivity, response time and stability for applications to the rapid process monitoring has been characterized. The optode fiber consists of label-free nIR fluorescent SWNT transducers embedded within a protective yet porous hydrogel attached to the end of the fiber waveguide. The optode is capable of differentiating the aggregation status of human immunoglobulin G (IgG), reporting the relative fraction of monomers and dimer aggregates of IgG with sizes 5.6 and 9.6 nm, respectively, in under 5 min of analysis time. A lab-on-fiber design shows potential for at-line protein monitoring with the integration of miniaturized sensor tips with mechanical flexibility. Other classes of bioanalytes (neurotransmitter, cytokines, ROS) can be tested using similar sensor constructs, and one can achieve high SNR at concentrations of interest demonstrating that the fiber optic nanosensor system could be applied to various biochemical process monitoring. This fiber optic system is envisioned to be a vital component of coupling fluorescent based nanosensors into both continuous and batch processes monitoring.

An example of preparing the sensors described herein follows.

Materials

All materials were purchased from Sigma-Aldrich unless stated otherwise. Highly purified CoMoCAT (6,5)-enriched SWNTs were used for all experiments and were provided to us by Chasm Advanced Materials. Tissue culture-treated well plates were purchased from Genesee Scientific. Molecular biology agarose was purchased from Bio-Rad, and recombinant Protein A (rPA, His-tagged at N-terminus) was purchased from Abcam. Human IgG1 (conatumumab) samples were provided to us by Amgen. IgG1 samples were provided in a formulation buffer containing 10 mM sodium acetate and 9% sucrose, at a pH of 5.2.

Preparation and Characterization of SWCNT Dispersions

All materials were purchased from Sigma-Aldrich unless stated otherwise. Highly purified CoMoCAT (6, 5)-enriched SWNTs were used for all experiments and were provided to us by Chasm Advanced Materials. Tissue culture-treated well plates (Cat#: 25-104) were purchased from Genesee Scientific. Molecular biology agarose was purchased from Bio-Rad, and recombinant Protein A (rPA, His-tagged at N-terminus) was purchased from Abcam. Purified CoMoCAT SWNTs (1 mg) were mixed with 15 mL of 0.25 w % chitosan solution in 1 vol % acetic acid. This solution was tip sonicated (Qsonica Q125) using a 0.25 in. probe for 40 minutes in an ice bath at 10 W. The crude SWCNT dispersion was centrifuged twice at 16,000 g for 90 minutes, in which the top 80% of supernatant was collected each time. The concentration of the purified SWCNT dispersion was approximated by collecting the absorption spectrum (Cary 5000, Agilent technologies).

Sensor Fabrication and Functionalization

Sensors were fabricated using the same method outlined by Nelson et al. Briefly, a 0.2% agarose solution was prepared in water and heated until the agarose was completely melted. Once the solution cooled to about 50° C., 50 µL aliquots were deposited on the bottom of a 96-well plate and allowed to cure in a humidified environment at room temperature for 45 minutes. Approximately 15 µL of 1 mg/L chitosan-SWCNT solution was added atop each gel, and the well plate was placed in a humidified chamber at 38° C. for 45 minutes to promote diffusion of SWCNTs into the hydrogel matrix. The well plate was later allowed to cool at room temperature for at least 10 minutes before washing each well with 150 µL of water to remove unbound SWCNTs.

Sensors were functionalized using a similar procedure as those reported previously. See, for example, Reuel, N. F. et al. Transduction of Glycan-Lectin Binding Using Near-Infrared Fluorescent Single-Walled Carbon Nanotubes for Glycan Profiling. *J Am Chem Soc* 133, 17923-17933, (2011); hang, J. Q. et al. A Rapid, Direct, Quantitative, and Label-Free Detector of Cardiac Biomarker Troponin T Using Near-Infrared Fluorescent Single-Walled Carbon Nanotube Sensors. *Adv Healthc Mater* 3, 412-423, (2014); and Nelson, J. T. et al. Mechanism of Immobilized Protein A Binding to Immunoglobulin G on Nanosensor Array Surfaces. *Anal Chem* 87, 8186-8193, (2015), each of which is incorporated by reference in its entirety. First, a solution of 5 mg/ml succinic anhydride in 25×PBS was added atop the sensors to convert the primary amine groups to carboxylic acids. This reaction was allowed to proceed overnight. After washing the sensor gels two times with 150 µL of water, the carboxylic acid groups were activated by a solution of 20 mg/ml 1-ethyl-3-(3-dimethylaminopropyl) carbodiimide (EDC) and 60 mg/ml N-hydroxysuccinimide (NHS) in MES buffer for 2 hours. Following this activation step, the sensors were washed two times with 150 µL water and reacted with a solution of approximately 14 mM Cu(II) chelated by $N_\alpha,N_\alpha$-Bis(carboxymethyl)-L-lysine hydrate (Cu-NTA).

To create the Cu-NTA solution, 37 mg of $N\alpha,N\alpha$-Bis (carboxymethyl)-L-lysine hydrate (NTA) was combined with 170.5 mg $CuCl_2$-$2H_2O$ and 10 mL of 0.5×PBS. To precipitate out the excess, unchelated Cu(II) ions, the solution pH was raised to 7.5 via the addition of approximately 600 µL of 3M NaOH. This solution was centrifuged at 1200 rpm for 7 minutes, after which the supernatant was used for reaction with the EDC/NHS-activated sensors.

Alternatively, an agarose solution (0.2%) was prepared in distilled water and boiled until the agarose was completely melted. Once the solution cooled to about 60° C., 50 μL aliquots were deposited on the bottom of a 96-well plate (25-104, Geness Scientific) and allowed to cure in a humidified environment at room temperature for 45 min. Approximately 15 μL of 1 mg/L chitosan-SWNT solution was added atop each gel, and the well plate was placed in a humidified chamber at 38° C. for 60 min to promote diffusion of SWNTs into the hydrogel matrix. The well plate was later allowed to cool at room temperature for 15 min before washing each well with 150 μL of water to remove unbound SWNTs. Sensors were functionalized using a similar procedure as those reported previously. See, for example, Salem, D. P.; Gong, X.; Lee, H.; Zeng, A.; Xue, G.; Schacherl, J.; Gibson, S.; Strano, M. S. Characterization of Protein Aggregation Using Hydrogel-Encapsulated nIR Fluorescent Nanoparticle Sensors. *ACS Sens.* 2020, 5, 327-337, which is incorporated by reference in its entirety. First, a solution of 5 mg/mL succinic anhydride in 25×PBS was added atop the sensors to convert the primary amine groups to carboxylic acids. This reaction was allowed to proceed overnight. After washing the sensor gels two times with 150 μL of water, the carboxylic acid groups were activated by a solution of 20 mg/mL 1-ethyl-3-(3-dimethylaminopropyl) carbodiimide (EDC) and 60 mg/mL N-hydroxy succinimide (NHS) in MES buffer for 2 hr. Following this activation step, the sensors were washed two times with 150 μL water and reacted with a solution of approximately 14 mM Cu(II) chelated by Nα,Nα-Bis(carboxymethyl)-L-lysine hydrate (Cu-NTA). To create the Cu-NTA solution, 37 mg of Nα,Nα-Bis(carboxymethyl)-L-lysine hydrate (NTA) was combined with 170.5 mg $CuCl_2$-$2H_2O$ and 10 mL of 0.5× PBS. To precipitate out the excess, unchelated Cu(II) ions, the solution pH was raised to 7.5 via the addition of approximately 600 μL of 3M NaOH. This solution was centrifuged at 1200 rpm for 7 min, after which the supernatant was used for reaction with the EDC/NHS-activated sensors.

Preparation of Stressed IgG1 Samples

Stressed IgG1 samples were prepared by exposing 100 mg/ml solutions of IgG1 to UV light for varying periods including 3 h, 7 h, 26 h, 45 h, and 74 h. UV exposure was performed in a stability chamber equipped with a UVA lamp (wavelength range 320-400 nm) operating at a power of 22 $W/m^2$ at ambient temperature.

Human agonist monoclonal ($IgG_1$) antibody (conatumumab, AMG 655) samples were provided to us by Amgen. See, for example, Bajaj, M.; Heath, E. I. Conatumumab: A Novel Monoclonal Antibody against Death Receptor 5 for the Treatment of Advanced Malignancies in Adults. *Expert. Opin. Biol. Ther.* 2011, 11, 1519-1524, which is incorporated by reference in its entirety. $IgG_1$ samples were provided in a formulation buffer containing 10 mM sodium acetate and 9% sucrose, at a pH of 5.2. UV exposure was performed in a stability chamber equipped with a UV lamp (wavelength range 320-400 nm) operating at a power of 22 $W/m^2$ at ambient temperature. 10 mM serotonin (5-hydroxytryptamin), adrenaline (±epinephrine), and (±)-norepinephrine (+)-bitartrate salt (Sigma Aldrich) solutions were prepared with dimethyl sulfoxide (DMSO). 100 mM hydrogen peroxide ($H_2O_2$, Sigma Aldrich) was prepared with 0.1 M NaCl solution.

SWCNT Near-Infrared Fluorescence Measurements

SWCNT fluorescence measurements were collected using a single-channel NIR photodetector (ThorLabs, PDF10C). Sensors were excited at 565 nm using a high-powered LED (ThorLabs, M565L3) and fluorescence was collected between 950 nm and 1050 nm using a 950 nm long-pass filter and 1050 nm short-pass filter. Cu-NTA functionalized sensors were loaded with rPA at a concentration of 200 μg/ml in PBS for at least 15 minutes. After loading, unbound protein was removed by washing the well with 150 μL PBS. To remove artifacts associated with analyte mixing, IgG1 solution was added directly atop the sensor hydrogels at a concentration of 10 mg/ml.

For experiments involving an extra tunable hydrogel layer above the sensors (FIG. 5C), the hydrogel layer was added directly atop the washed sensor gel after rPA loading. The pore size and thickness of the tunable layer were controlled by modifying the agarose concentration and volume of agarose solution added atop the sensors, respectively. The agarose solution used for the tunable layer was kept at a constant temperature of 55° C. and was used the same day it was prepared. Once the tunable hydrogel layer was added, it was allowed to cure at room temperature for at least 30 minutes before conducting an experiment. $IgG_1$ binding experiments involving a tunable hydrogel layer were conducted in the same way as outlined above, where $IgG_1$ solution at a concentration of 10 mg/ml was added directly atop the hydrogel.

Optode Fiber Measurements.

Sensors were excited with 561 nm (MGL-FN-561 200 mW, Opto Engine LLC/197 (length)×70 (width)×50 (height) $mm^3$, 2.0 kg) or 785 nm (MDL-III-785 500 mW, Opto Engine LLC). Here, versatile excitation sources including high power LED could be coupled to fiber optic platform for the benchtop mobile cart integration. The laser light propagates through fiber optic reflection/backscatter probe bundles (core diameter 200 μm, fiber length 2 m, weight 0.16 kg, RP29 Thorlabs) to the samples, and the fluorescence light propagates through the fiber to InGaAs amplified photodetector (PDF10C, Thorlabs). The fiber optic probe consists of 6 fibers around 1 fiber configuration where the central fiber provides the light delivery to the SWNT sensor hydrogel. The surrounding 6 fibers collect the near infrared fluorescence light from SWNT sensor hydrogel. To reduce laser scattering and autofluorescence at hydrogel, 900 nm short pass filter and 900 nm long pass filter were inserted at the laser and photodetector, respectively. A focusing lens with a focal length of 30 mm is placed to efficiently collect fluorescence signal at 0.5 mm-diameter active area of the photodetector. To suppress baseline noise from environments such as ceiling lamps, a black hardboard enclosure protects around the samples and optode fiber. All the components of the instrument are loaded on a mobile cart (15Y320, Grainger, size: depth 18", width 24", height 26-42"). For the real-time signal measurement of IgG, 40 μL PBS and 20 μL of protein A were added in series and fluorescence signals were measured for 30 min. Then, 100 μL of PBS was injected twice to flush remaining chemical and 10 μL of IgG solution was added to measure the signals. Usually, the signal saturated at 300-600 sec. For the measurement of various bioanalytes, 50 μL of nanosensors were added in sensor tip and baseline was measured for 5 min. Then, 5 μL of each analyte solution were added and signals were measured for 20 min.

Nanoparticle Tracking Analysis

Nanoparticle tracking analysis was performed using a NanoSight Model LM10 manufactured by Malvern Instruments. $IgG_1$ samples were tested at a nominal concentration of 200 μg/ml and 20 videos were collected at 30 seconds per video. Analysis of the extracted particle trajectories was completed using a recently developed Bayesian model implemented in Matlab.

Building a Fiber-Optic System

The fiber-optic system, so-called optode, is illustrated in FIG. 1A. The optode system contains an optical fiber bundle coupled to the sensor hydrogels for direct immersion in the sample matrix and also coupled to both excitation laser, and photodetector described as follows.

Samples were excited with 561 nm (MGL-FN-561 200 mW, Opto Engine LLC) or 785 nm (MDL-III-785 500 mW, Opto Engine LLC). The laser will be switched according to the chirality of SWCNT; 561 nm light excites (6,5) SWCNT while 785 nm light excites HiPCO SWCNT including (10,2), (9,4), (8,6), (8,7) SWCNT. The laser light propagates through fiber optic reflection/backscatter probe bundles (RP29, Thorlabs) to the samples, and the fluorescence light propagates through the fiber to InGaAs amplified photodetector (PDF10C, Thorlabs). The fiber optic probe consists of 6 fibers around 1 fiber configuration where the central fiber provides the light delivery to the SWNT sensor hydrogel. The surrounding 6 fibers collect the near infrared fluorescence light from SWNT sensor hydrogel. To reduce laser scattering and autofluorescence at hydrogel, 800 nm short pass filter and 900 nm long pass filter were inserted at the laser and photodetector, respectively. A focusing lens with a focal length of 30 mm is placed to efficiently collect fluorescence signal at 0.5 mm-diameter active area of the photodetector. To suppress baseline noise from environments such as ceiling lamps, a black hardboard enclosure protects around the samples and fiber optic. All the components of the instrument are loaded on a mobile cart (15Y320, Grainger) so that users can carry the fiber-optic system as shown in FIG. 1B.

Detecting NTA/Cu(II)His-Tag/Antibody

Figure 2B:
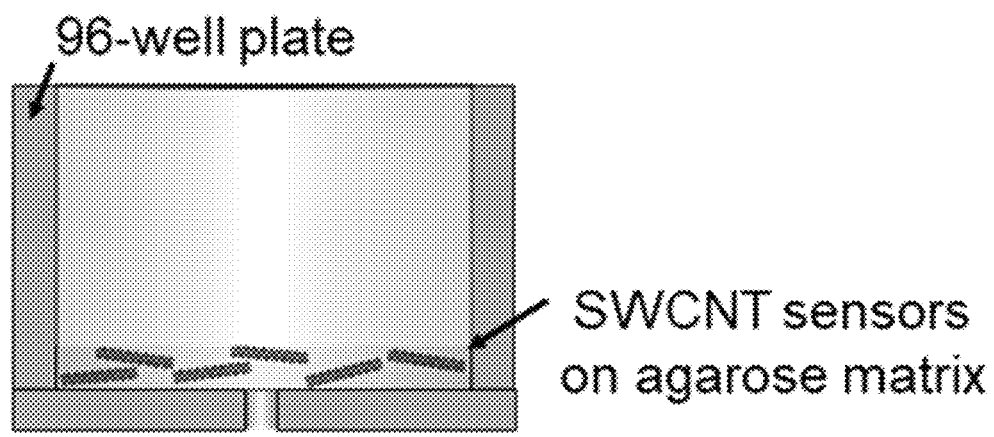
Figure 2C:
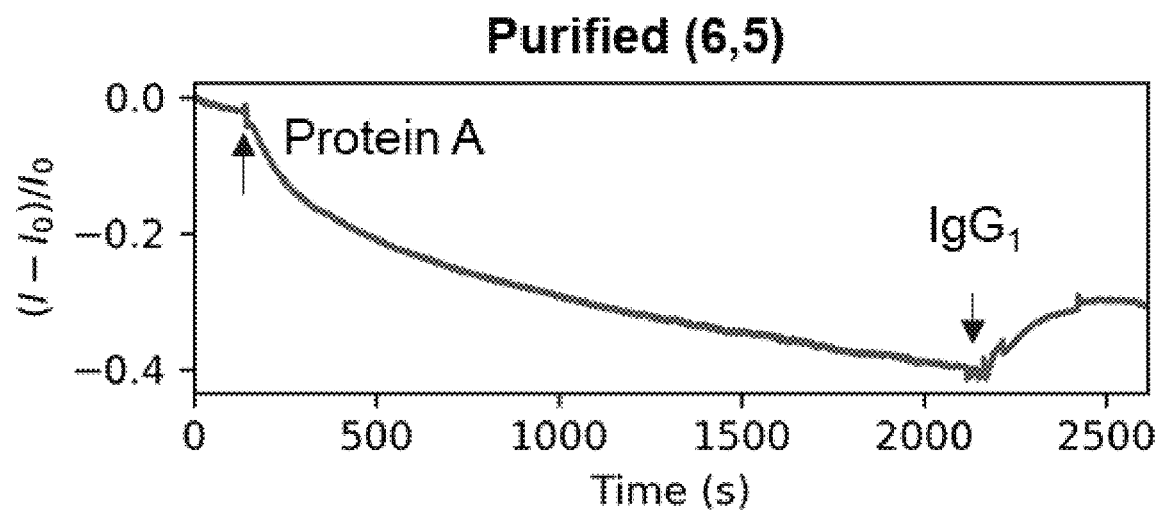
Figure 2D:
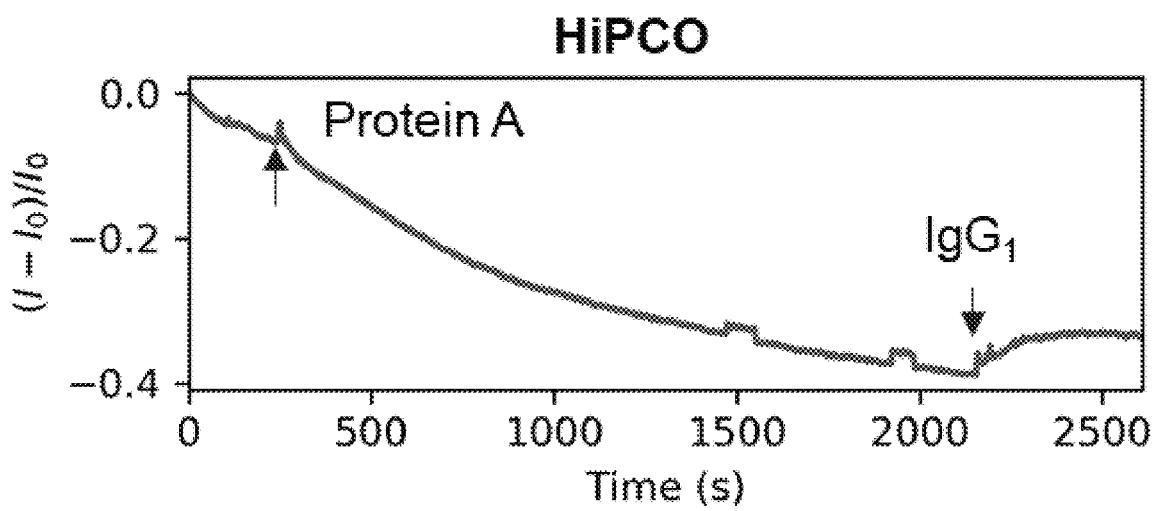

The optode system aims at-line form factor to detect biopharmaceutical aggregation. To prove the concept, we began with sensors in the 96-well plate excited and detected from the bottom (FIG. 2A and FIG. 2B). The fabrication methods described above for the hydrogel sensors were used here. Sensor response of two different types of hydrogel sensors including purified (6,5) SWCNT were tested SWCNT (FIG. 2C) and HiPCO (FIG. 2D). The sensor responses of both SWCNT show quenching on adding protein, while the time trace shows turn-on response on adding IgG. These trends are consistent with of previous measurement in the custom-built NIR fluorescence instrument. Therefore, these measurements prove the capability of the optode system.

Figure 3B:
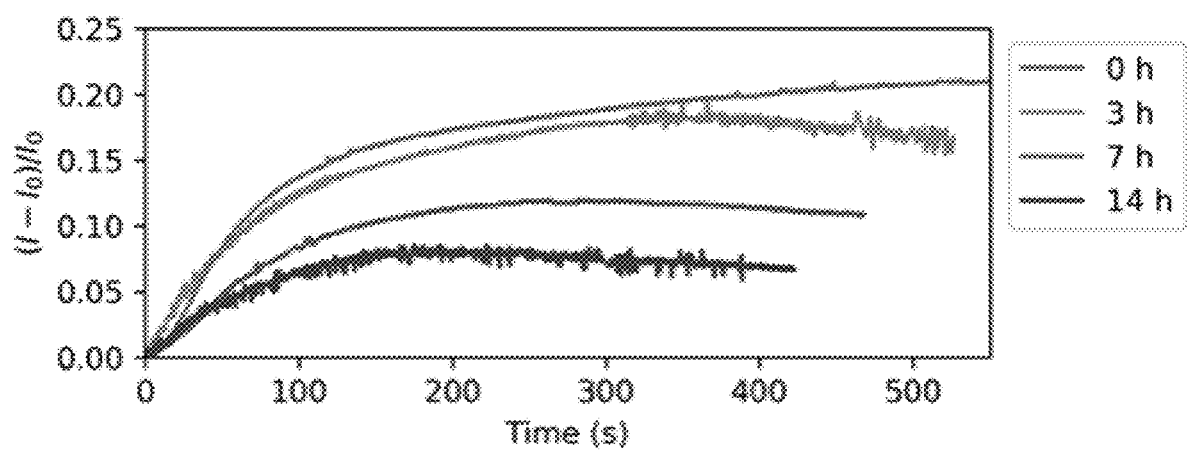
FIG. 3B depicts the response of protein A-loaded sensors to 10 mg/mL unstressed, 3, 7, and 14-hour stressed IgG$_1$.

The optode system to detect IgG aggregation with the tunable agarose gel layer on top of the SWCNT sensors (FIG. 3A), where the tunable layer modulates the diffusion of the analyte. Analytes of $IgG_1$ that underwent different stress levels via UV light irradiation for 0, 3, 7, and 14 hours were added and the sensor responses measured (FIG. 3B). The responses to 0 and 14-hour stressed $IgG_1$ are relatively small whereas the responses to 3 and 7-hour stressed $IgG_1$ are prominent. The response variation allows for differentiation of aggregation levels.

Figure 4A:
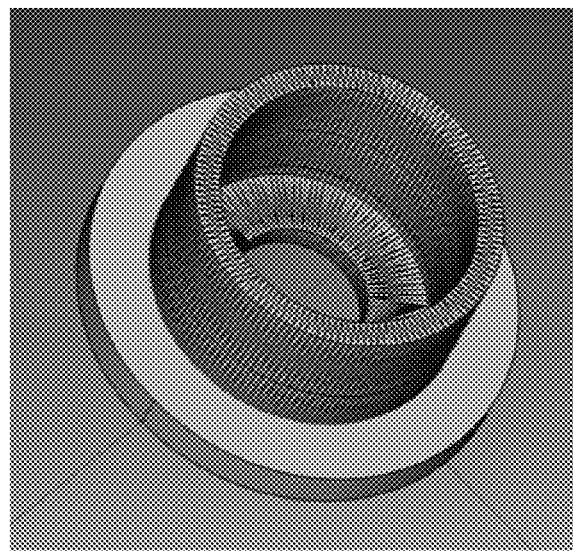
FIGS. 4A-4B depict CAD designs of (FIG. 4A) the sample interface mold holding the hydrogel sensors and (FIG. 4B) optical fiber interface screwed into SMA-terminated optical fiber.
Figure 4B:
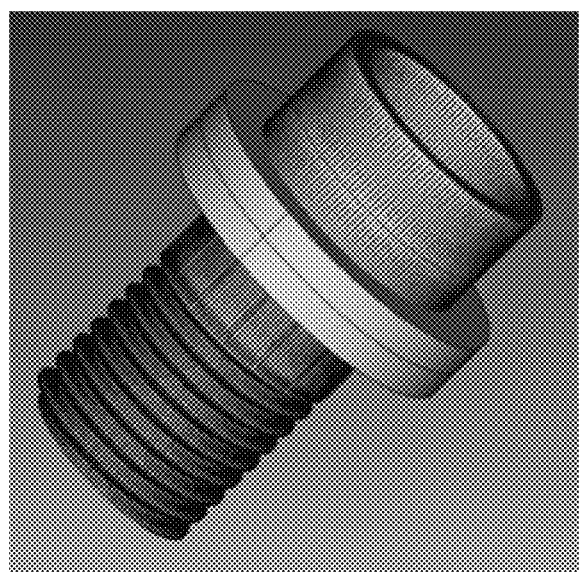

The optode system can be a small form factor for conducting sensor measurements at-line of biopharmaceutical manufacturing. The optode system can easily be integrated into different areas of chemical processing steps. FIG. 4A shows a CAD design of the sample interface mold holding the hydrogel sensors, and FIG. 4B shows the design of optical fiber interface screwed into SMA-terminated optical fiber, where the molds were fabricated with a 3D printer. Such capsule molds allow us to easily exchange hydrogel sensors and also make the hydrogel sensor a disposable component. The hydrogels will be pre-fabricated in the molds that interfaces readily with the fiber optic probe.

Fiber Optic Optimization
Combining Multiple Excitation Sources

As part of the fiber optic based near infrared spectroscopy system, one of the first objectives was to assess and determine methods for combining multiple excitation sources into the single multi-mode fiber optic that will be the center fiber of the fiber optic probe. The three methods that were determined as viable is to use a pair of prisms that would help couple the different laser wavelengths into a collimated beam that would then be launched into the fiber (FIG. 23A), the use of a series of long pass dichroic mirrors that would be placed in series and then launched into the fiber (FIG. 23B), and lastly to use multimode fiber couplers to couple the fiber coupled lasers together (FIG. 23C). Ultimately, the configuration in FIG. 23C was chosen as it provides the least amount of transmitted light loss from the laser, provides the highest safety as the light is all contained within the fiber optics without the use of free optics, and similarly provides the most stability (i.e. less need of optical realignment for day to day use and during movement of instrument).

Fiber Optic Probe Design

Figure 24A:
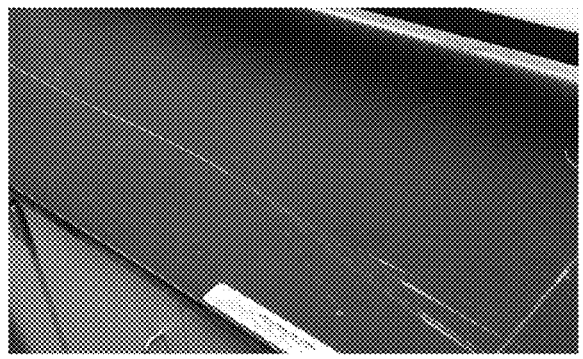
FIG. 24A depicts a bundle of multimode optical fibers placed inside a Teflon jacket.
Figure 24B:
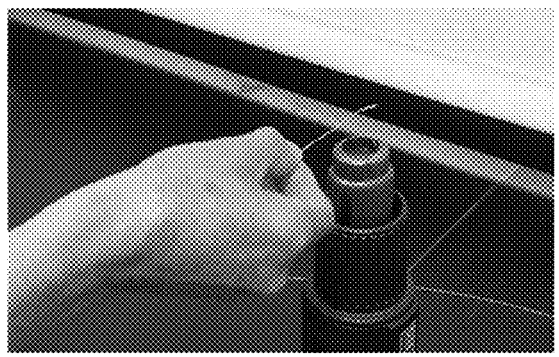
FIG. 24B depicts a Teflon jacket that was shrunken by heat over the fiber bundle to maintain spatial configuration of the fibers.

The fiber optic probe was made as follows. The bundle of fibers is brought into place using a copper wire to hold it in place. The entire bundle was placed into a Teflon jacket (FIG. 24A) that is then shrunk over the fiber bundle using a heat gun at 700 F (FIG. 24B).

Figure 25A:
FIG. 25A depicts an epoxy filled syringe used to place into the epoxy into the stainless steel tubing containing the fiber optic bundle.
Figure 25B:
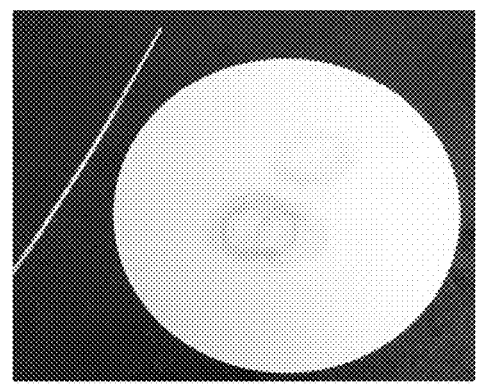
FIG. 25B depicts (left) a tip of the fiber optic probe and (right) sand-paper used to manually polish the end of the fiber optic probe.
Figure 27A:
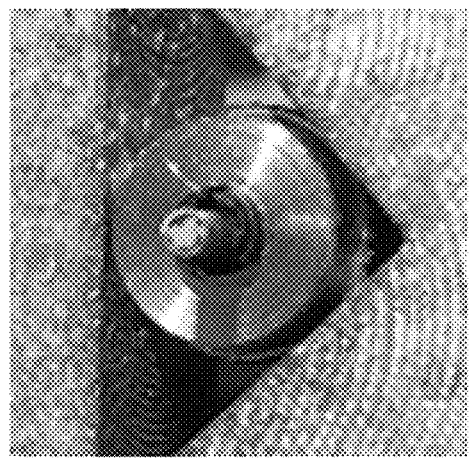
FIGS. 27A-27C show the fiber optic probe was visually inspected after each polishing step.
Figure 27B:
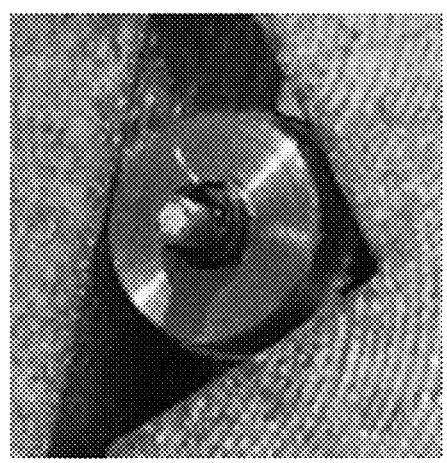
Figure 27C:
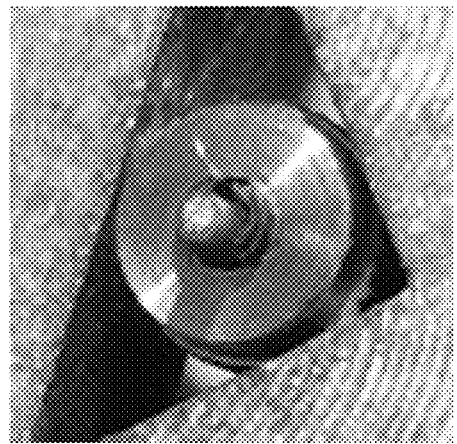

The fiber bundle was placed inside of a piece of stainless steel tubing and fixed into place using Loctite M31CL epoxy (FIG. 25A). Once allowed dry, the end of the fiber optic probe was cleaved using a diamond cutter and initially manually polished using sandpaper (FIG. 25B). The epoxy was then allowed to dry for 24 hr.

Using a series of sand paper in descending granularity (30 µm, 15 µm, 5 µm, 3 µm, 1 µm), the fiber optic probe end was polished to a smooth surface (FIGS. 26A-26D and FIGS. 27A-27C).

Figure 28A:
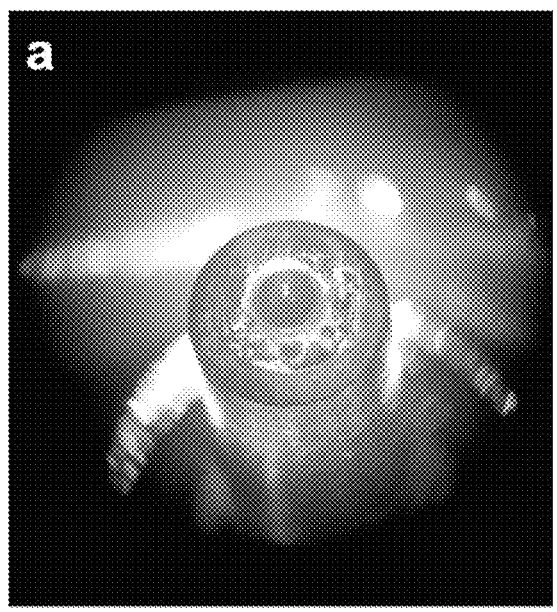
FIG. 28A depicts fiber optic probe tip with half ball micro-lens.
Figure 28B:
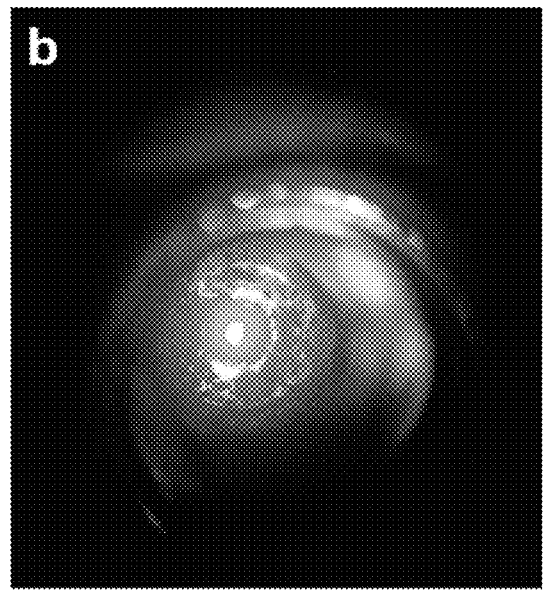
FIG. 28B shows illumination of center fiber.
Figure 28C:
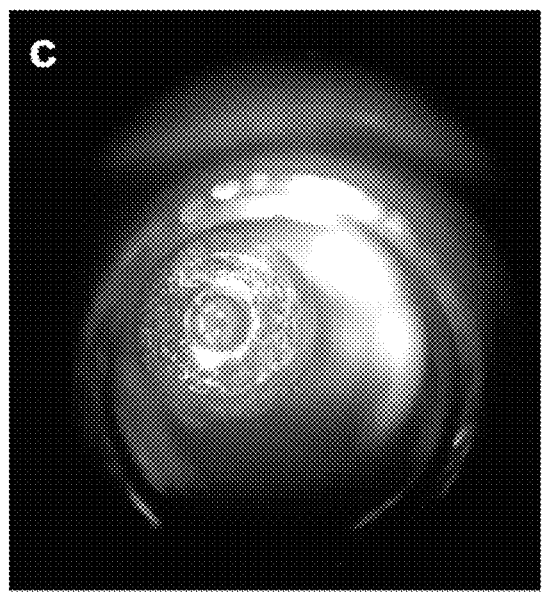
FIG. 28C shows illumination of outer six fibers.

The fiber bundle was then split into the 6 collection fibers into one end and the single central fiber into a second end (FIGS. 28A-28C). The three ends of the fiber optic probe were then SMA and FC/PC connectorized accordingly to be able to interface directly with the fiber coupled lasers and photodetectors. A sapphire half ball lens was placed onto the probe end of the fiber and glued in place with optical epoxy (FIG. 29).

Power Meter Integration for Laser Fluctuation Monitoring

Figure 30A:
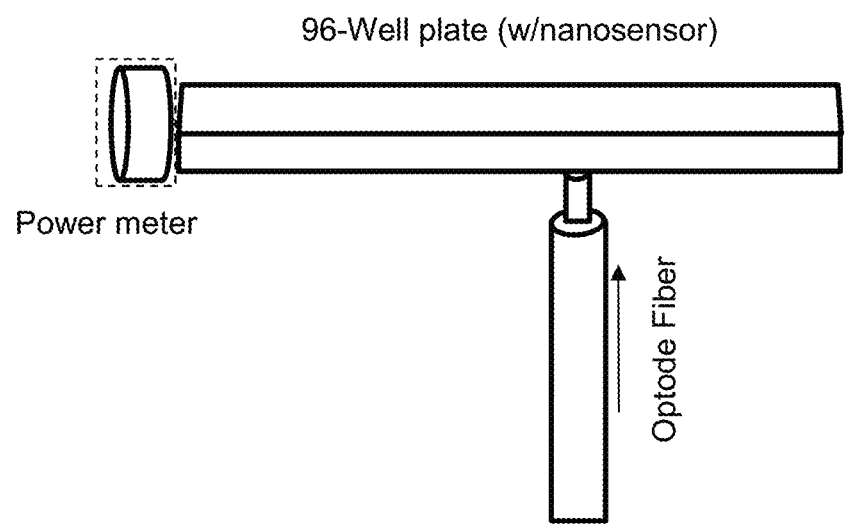
FIGS. 30A-30B shows fluorescence time traces of raw and noise-corrected data by continuous monitoring of laser power fluctuation using power meter.
Figure 30B:
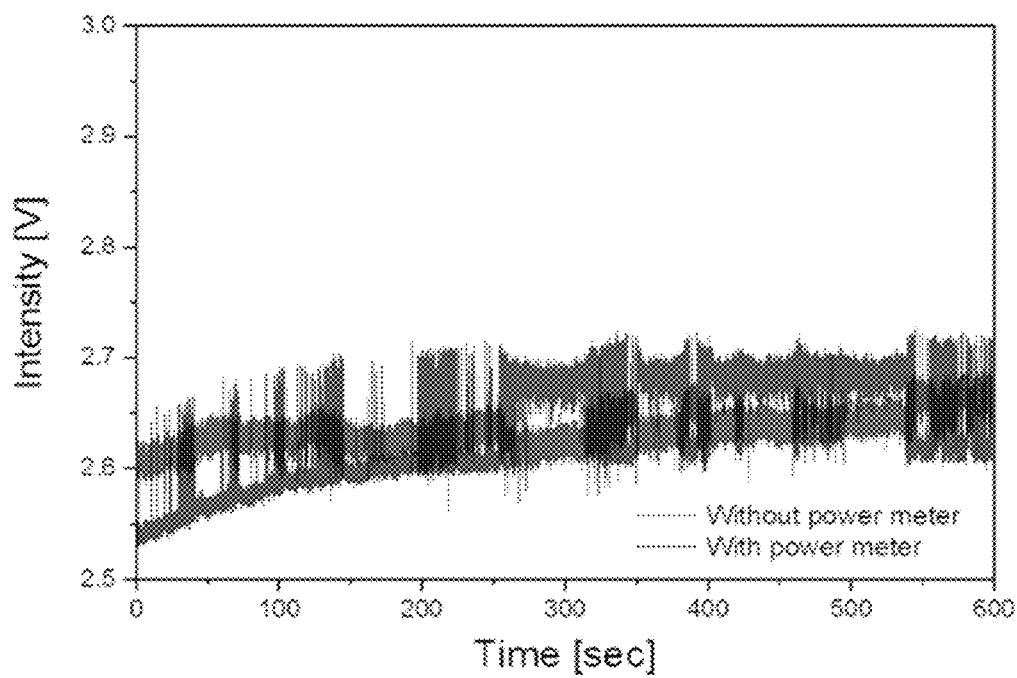
Figure 31A:
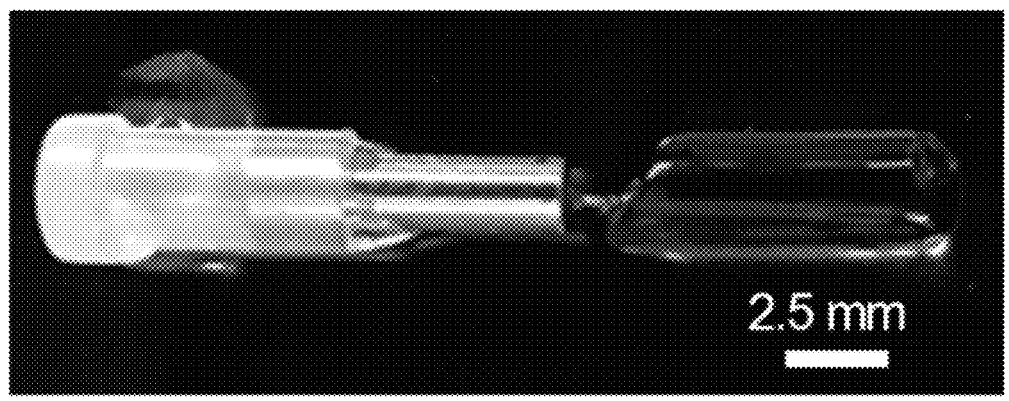
FIG. 31A depicts a coating of fiber optics with hydrogels 2-fiber ferrule (1 excitation & 1 collection) with SWNT hydrogel covalent bound to the fibers.
Figure 31B:
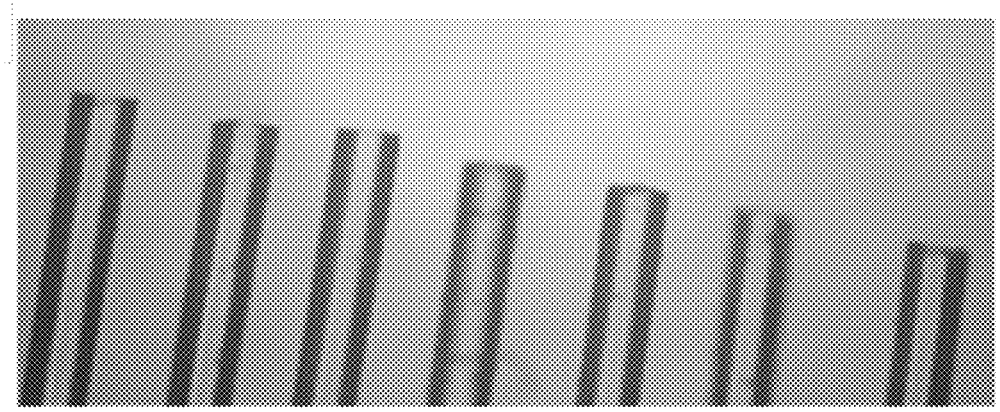
FIG. 31B depicts fiber size & spacing to optimize fiber placement & geometry between excitation and collection fibers.
Figure 31C:
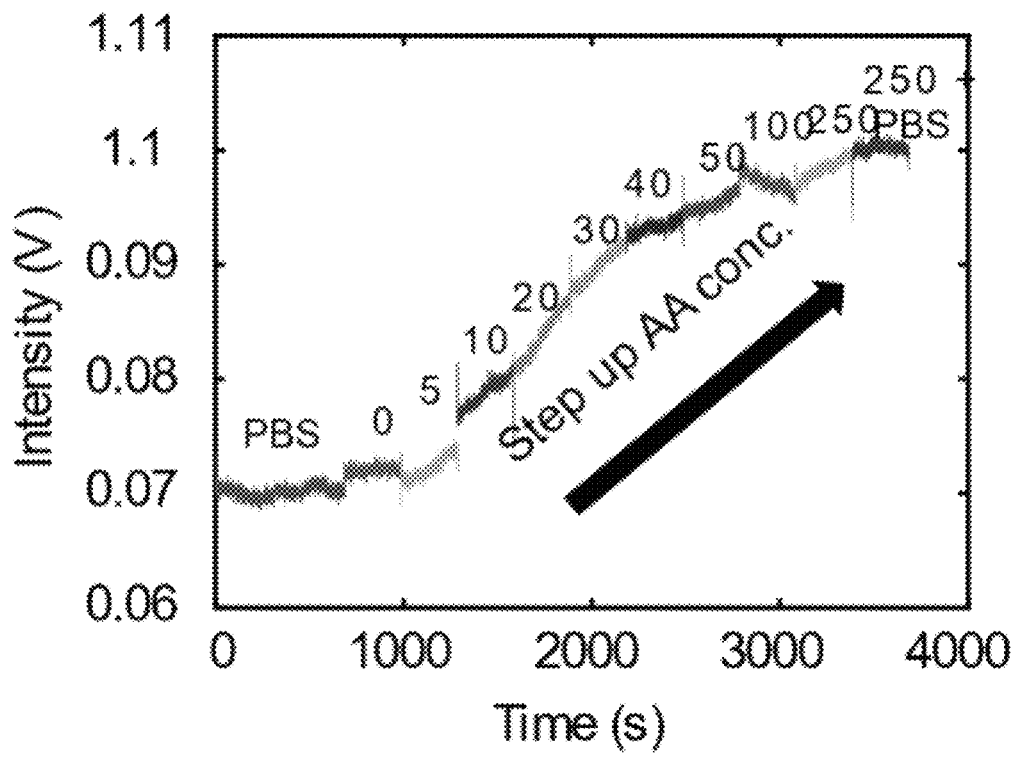
FIG. 31C depicts increasing ascorbic acid concentration corresponds to stepwise fluorescence intensity increases.
Figure 31D:
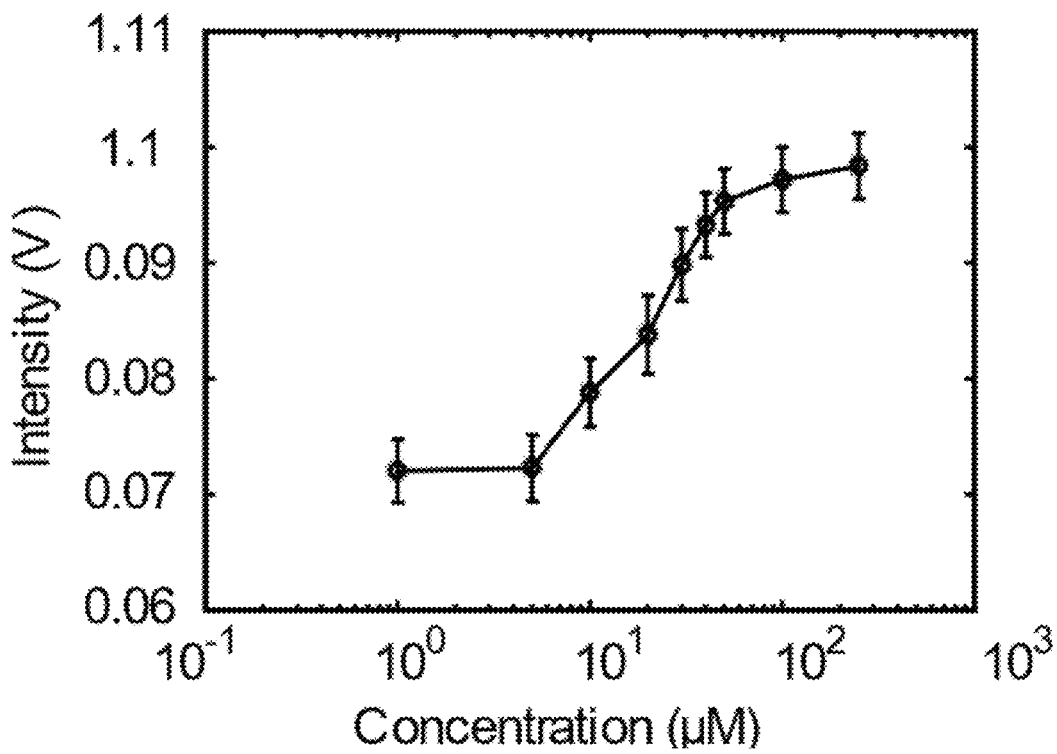
FIG. 31D depicts a calibration curve for ascorbic acid using near infrared fiber optic spectroscopy system.
Figure 31E:
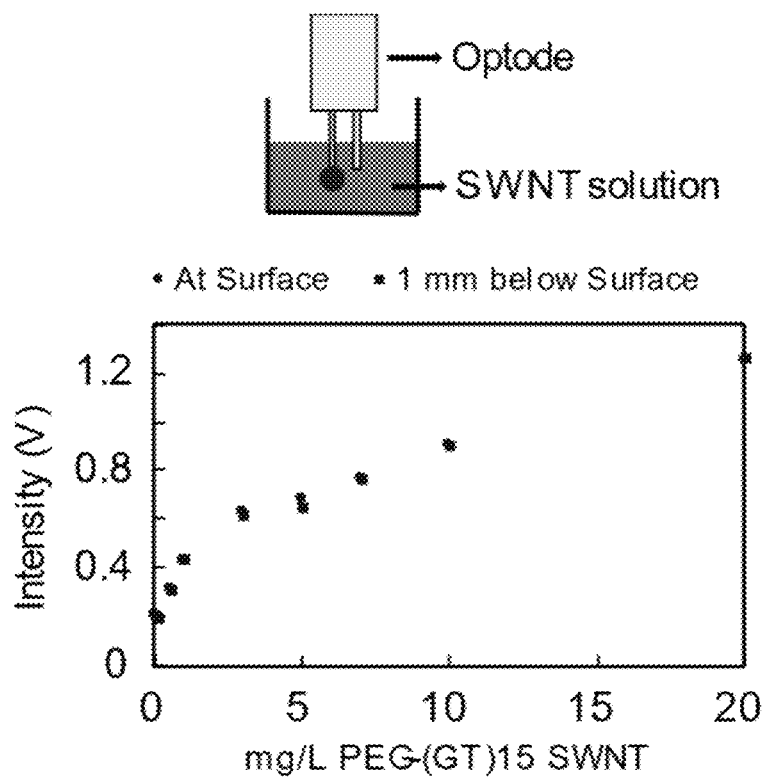
FIG. 31E depicts a calibration curve for ascorbic acid using the 2-fiber optic probe (1 excitation, 1 collection) placed at 1 mm below the solution surface. The red dot represents excitation light.
Figure 31F:
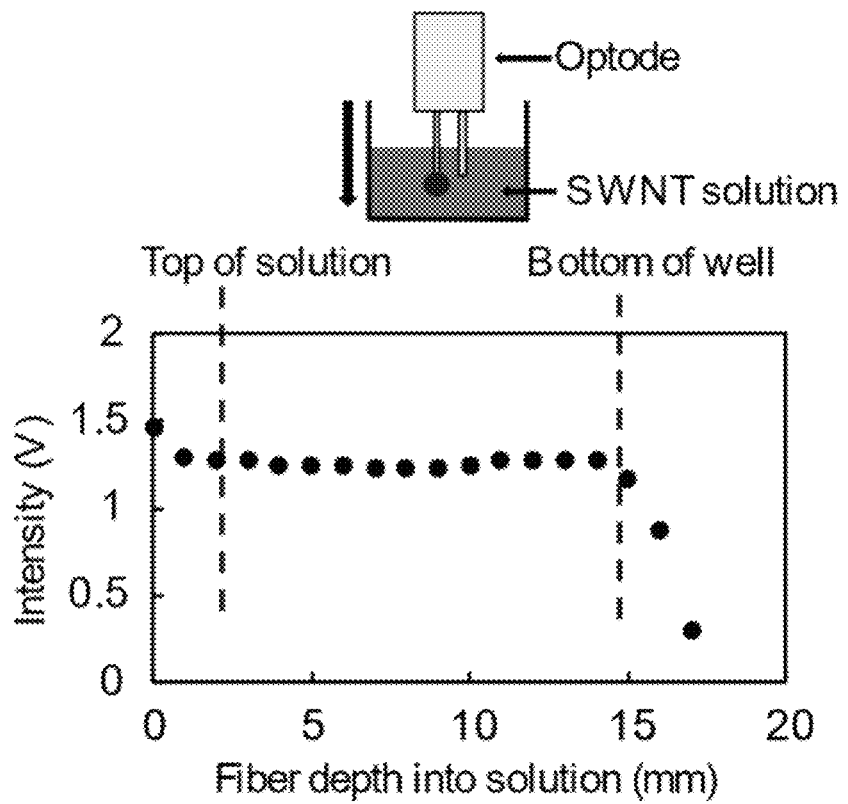
FIG. 31F depicts fluorescence intensity vs depth of fiber from above solution surface to bottom of plastic well with SWNT solution. This data demonstrates that fiber can detect SWNT within a 2 mm distance.

FIGS. 30A-30B show fluorescence time traces of raw and noise-corrected data by continuous monitoring of laser power fluctuation using power meter. FIG. 30A is a photo-image of experimental setup for power-meter monitoring. FIG. 30B is a real-time raw and noise-corrected fluorescence data.

Fiber Optic Interface Optimization

Methods of how to interface the fiber optic probe to the hydrogel were explored. The first method explored was to covalently bond the hydrogel to the fiber optics themselves. The second method is to develop a fiber optic probe that is then interfaced to the gels in a capsule mold. However, based on the initial experimental designs, it seems more promising for us to design a fiber optic probe where the hydrogel sensor component can easily be exchanged and the fiber optic itself could be autoclaved separately if needed for sterilization purposes. This method should help increase the lifetime of the fiber optic probe itself while making the hydrogel sensor a disposable component that can be readily switched out. The hydrogels will be pre-fabricated in molds that can then readily interface with the fiber optic probe.

Initial fabrication of covalently bonding a SWNT hydrogel to the end of a 2-fiber optics probe (FIGS. 31A-31F). Initial experiments are underway to experimentally optimize the design of a fiber optic probe such as determining the maximum distance of detection from the tip of the fiber optic probe, the distance between light excitation and light collection fibers, as well as the geometry of the light excitation and light collection fibers (i.e. 6 around 1 or other configurations).

Versatile Nanosensor Configuration

FIGS. 32A-32C show real-time fluorescence monitoring of (FIG. 32A) purified (6,5) chirality SWCNT (CHASM) and (FIG. 32B) HiPCO loading protein A showing sensor responses to 10 mg/mL unstressed human IgG. Fluorescence time-trace of (FIG. 32C) negative control sample, which no SWNT sensors were diffused in agarose hydrogel.

Limit of Detection for IgG Monitoring Using Optode Fiber Nanosensor

Limit of detection of the fiber optic form factor was investigated with lower concentration of IgG injection (2, 1, and 0.1 mg/mL). FIG. 33 clearly shows that response amplitude of the nanosensors decreased with lower concentration of IgG injection from 13.33 µM to 0.66 µM. In addition, for all concentration of IgG, the derived model was exactly fitted with real-time measured data. Especially, for the 0.66 µM IgG injection, nanosensor response was almost diminished after few seconds indicating that limit of detection of the nanosensor interfaced fiber optic is around below 660 nM, which is quite low concentration for process monitoring. This is almost identical with performance of conventional offline IgG detection platform. Since the limit of detection is critically affected by the signal-to-noise of the system, it could be further improved with modified monitoring technique of fiber optic nanosensor having low measurement noise.

Control Experiment of IgG Detection

FIG. 34 shows real-time fluorescence response of optode fiber onto IgG (10 µL, 10 mg/mL) injection without protein A. It is clearly seen that there are no any signal variations with IgG injection indicating that protein A is critical factor of IgG detection mechanism of the nanosensor layer.

Hydrogel Diffusion Model

The diffusion model consists of SWNT immobilized in agarose hydrogel layer with two thickness: (i) thickness $L_1$ from the top surface of hydrogel to sensor layer and (ii) thickness $L_2$ from lower top surface of hydrogel to sensor layer that accounts for cracks within the hydrogel layer formed during casting and/or heterogeneity in the hydrogel thickness. In adding of IgG, the one-dimensional diffusion of protein controlled by Fick's second law is expressed as $$\frac{\partial C}{\partial t} = C \frac{\partial^2 C}{\partial x^2} \quad (1)$$

where C is concentration of IgG, t is time after the addition, D is diffusion constant, and x is the distance from the top surface of agarose hydrogel. Assuming x=0 at the interface between hydrogel and IgG dispersions and $x=L_1$ at the SWNT sensors layer, the initial and boundary condition are described by the following equations $$C(x, 0) = 0 \quad (2)$$

$$C(0, t) = C_0 \quad (3)$$

$$\frac{\partial C}{\partial x}(L_1, t) = 0 \quad (4)$$

To obtain the approximate solution for the concentration at t and L, the $10^{th}$ order (n=10) Fourier expansion is applied to the separation of variable solution to equation (1) with the following form:

$$\frac{C(L, t)}{C_0} = \quad (5)$$

$$1 - \frac{4}{\pi} \sum_{n=0}^{\infty} \frac{(-1)^n}{2n+1} \exp\left(-\frac{D_g(2n+1)^2\pi^2 t}{4L^2}\right) \cos\left(\frac{(2n+1)\pi(L_{tot} - L)}{2L_{tot}}\right)$$

where n is the order of the expansion, $L_{tot}$ is the total thickness of the agarose hydrogel, and $D_g$ is the diffusion constant of protein through agarose hydrogel. For the next step, the second hydrogel thickness $L_2$ was introduced to equation (5) and the sensor response can be described as below.

$$C(t) = C_0 \left[\beta \frac{C(L_1, t)}{C_0} + (1 - \beta) \frac{C(L_2, t)}{C_0}\right] \quad (6)$$

where β is the fraction of the larger thickness. Finally, the equation (6) is fitted to the measured dynamic response curve on the optode fiber system. In order to differentiate the monomer and aggregated IgG in the optode fiber system, the molar fraction terms were introduced to equation (6): the ratio of monomer ($\alpha_{MP}$) and high molecular weight (HMW) IgG ($\alpha_{HMW}$). Then, the total concentration profile in two diffusion model with time scale can be expresses as following equation.

$$C_T(t) = \alpha_{MP}C_0\left[\beta\frac{C_{MP}(L_1, t)}{C_0} + (1-\beta)\frac{C_{MP}(L_2, t)}{C_0}\right] + \quad (7)$$
$$\alpha_{HMW}C_0\left[\beta\frac{C_{HMW}(L_1, t)}{C_0} + (1-\beta)\frac{C_{HMW}(L_2, t)}{C_0}\right]$$

With the final mathematical model, the equation (7) is fitted to the dynamic response of optode fiber to 0, 3, 7, and 74 hr stressed IgG with uncoupled system and the fitting parameters ($\alpha_{MP}$, $\alpha_{HMW}$, $L_1$, $L_2$, and β) were extracted.

Multiple Usability of 3D Sensing Tip

FIG. 35 shows maximum measurement counts of single 3D sensing tip. Sensor response to 10 µL of 10 mg/mL IgG with the SWNT sensor diffused in 0.2% agarose hydrogel. The black arrows indicate the addition of IgG, showing the increased fluorescent signal twice.

Results and Discussion

Sensor development

Figure 14:
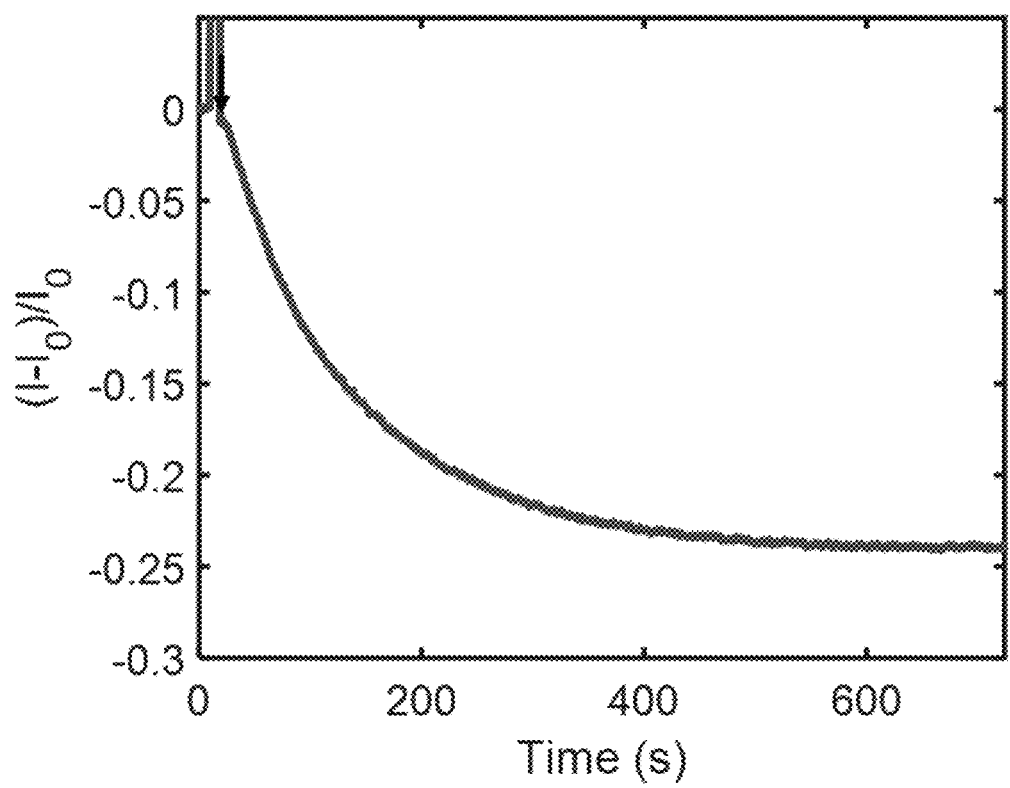
FIG. 14 shows a sensor loading curve for 100 μg/ml His-tagged recombinant protein A. The black arrow indicates the time of protein A addition.
Figure 15:
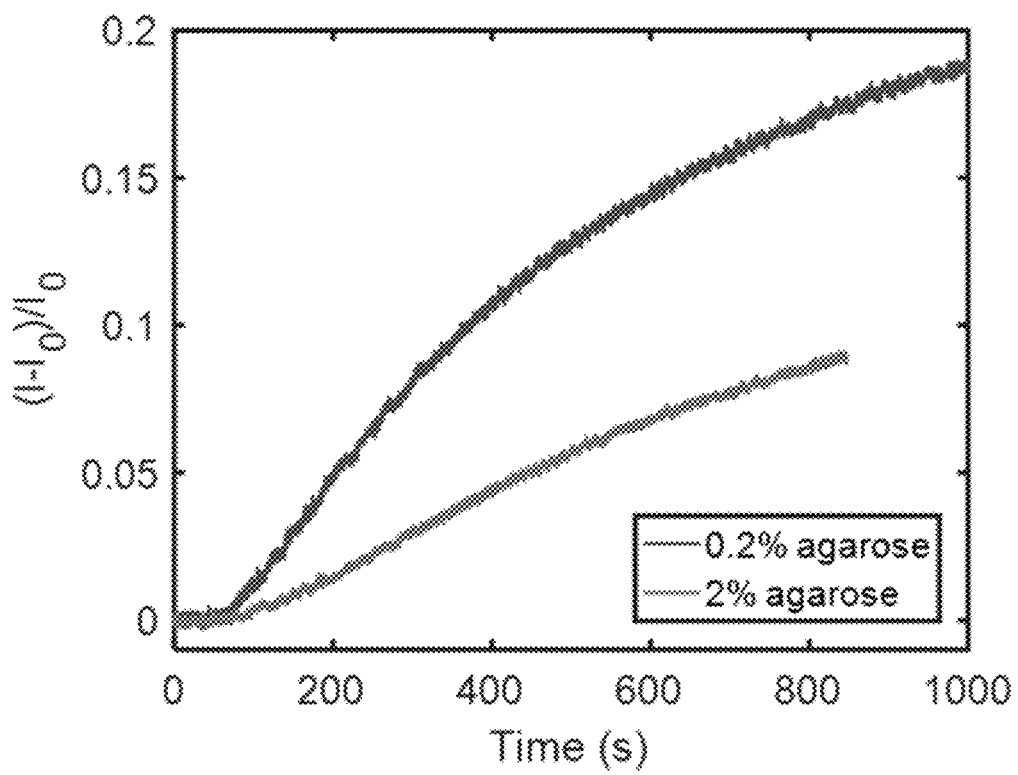
FIG. 15 shows sensor response to 10 mg/ml unstressed human IgG$_1$ using tunable layers of varying agarose concentration (equal tunable layer volume of 20 μL).
Figure 16:
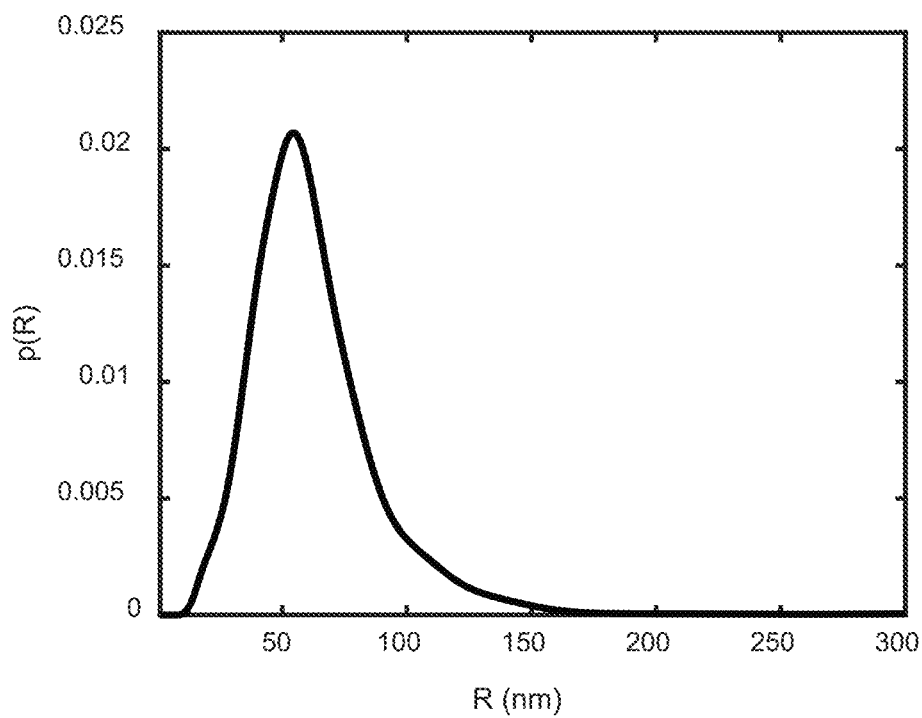
FIG. 16 shows nanoparticle tracking analysis results from the IgG$_1$ formulation buffer only.
Figure 17A:
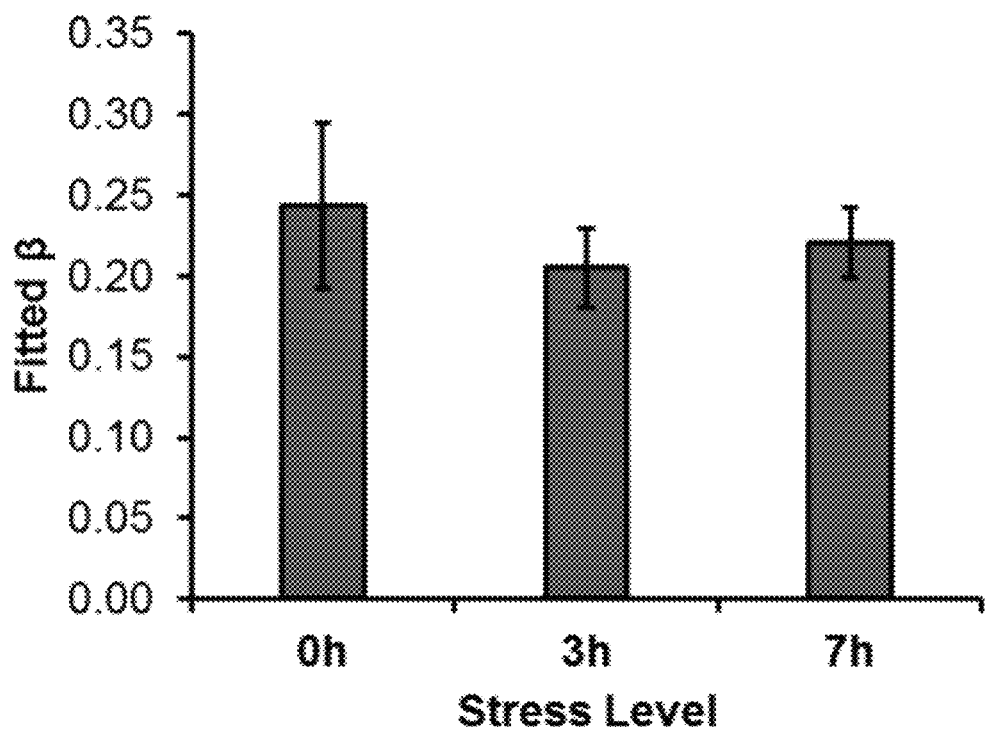
FIGS. 17A and 17B show, respectively, (FIG. 17A) β and (FIG. 17B) R$_{max}$ values obtained when specifying the composition of the IgG$_1$ material and fitting experimental data to the two-thickness model described herein.
Figure 17B:
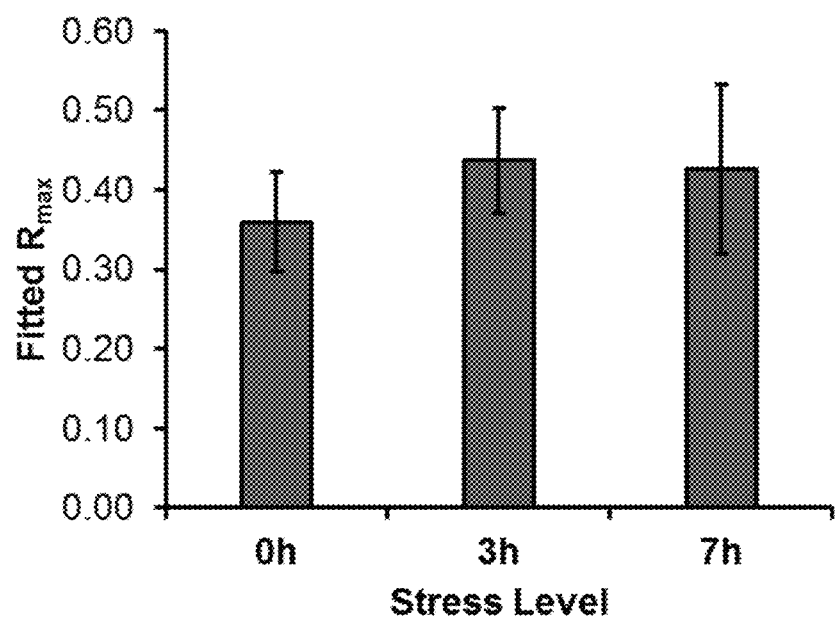

An overview of the sensor detection mechanism is provided in FIG. 1A and has been studied previously. See, for example, Nelson, J. T. et al. Mechanism of Immobilized Protein A Binding to Immunoglobulin G on Nanosensor Array Surfaces. *Anal Chem* 87, 8186-8193, (2015), which has been incorporated by reference in its entirety. Briefly, a series of functionalization reactions are performed to tether Cu-NTA groups to the chitosan wrapping, where the Cu(II) ion functions as a proximity quencher for SWCNT fluorescence. Addition of hexahistidine-tagged recombinant protein A (rPA) causes a quenching response as the rPA binds to the Cu(II) ions, indicating that the entire complex moves closer to the SWCNT surface (FIG. 14). This is consistent with previous work showing that protein A adsorbs to the surface of SWCNTs. Upon IgG$_1$ binding to the Cu(II)/rPA complex, the sensors exhibit a turn-on fluorescence response as the Cu(II)-SWCNT distance increases.

Figure 5B:
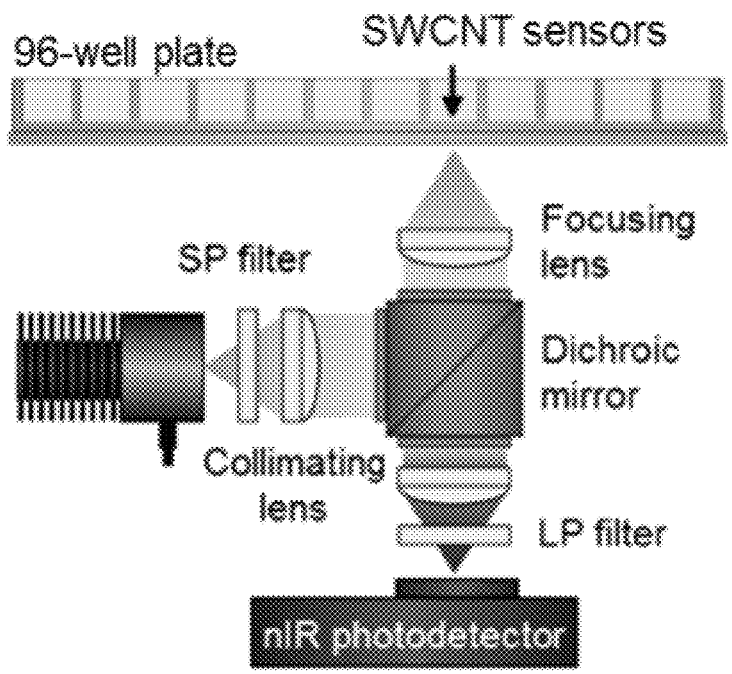

SWCNT sensors were fabricated in a 96-well plate and measured using a custom-built nIR-fluorescence instrument shown in FIG. 5B. Given that purified (6,5) SWCNTs were used for all experiments, sensors were excited at 565 nm using a high-powered LED to maximize signal. Fluorescence was collected using a single-channel nIR photodetector.

Figure 5C:
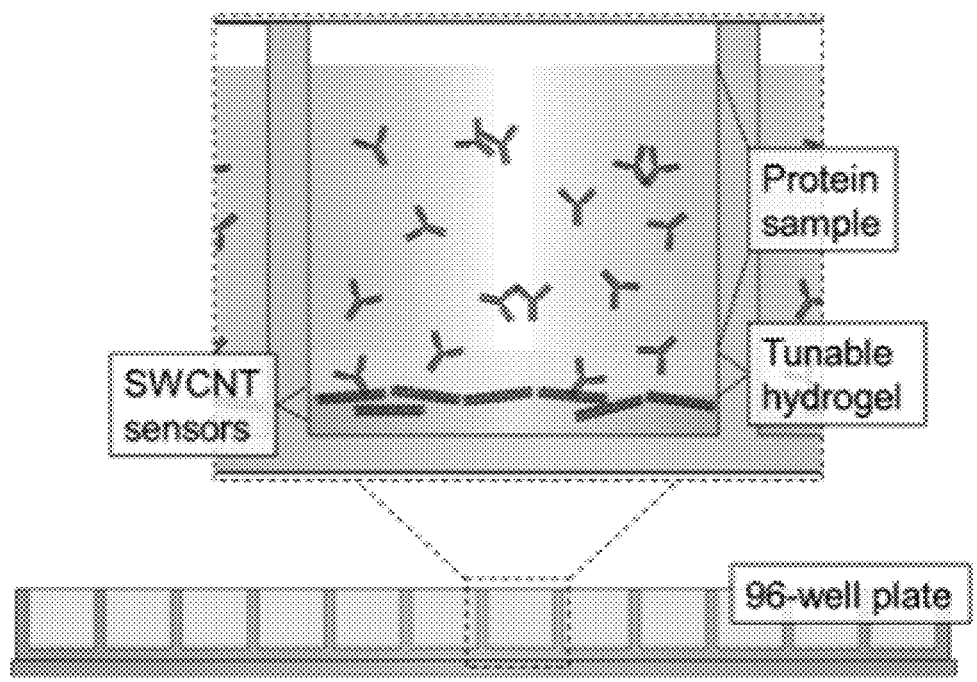

The approach to detect the presence of protein aggregates is shown in FIG. 5C, in which a tunable hydrogel layer was added atop a sensor hydrogel layer to modulate the diffusion of analyte. It was hypothesized that as a greater fraction of a protein sample contained high molecular weight species, the transient sensor response would be affected. To demonstrate this idea, the sensor response to 10 mg/ml human IgG$_1$ was measured with and without a tunable layer containing 30 µL of 0.2% agarose. The sensor response, R, was defined as the normalized change in SWCNT fluorescence, as defined by Equation 1, where I(t) is the fluorescence at time t and Jo is the initial fluorescence intensity.

$$R(t) = \frac{I(t) - I_0}{I_0} \quad (1)$$

Figure 5D:
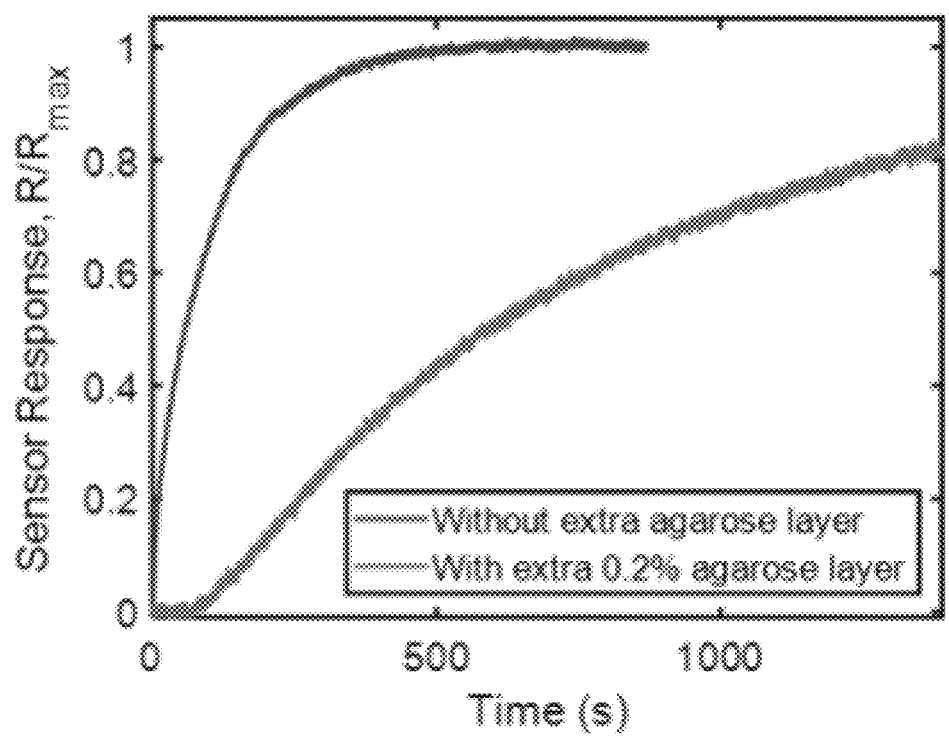
Figure 5E:
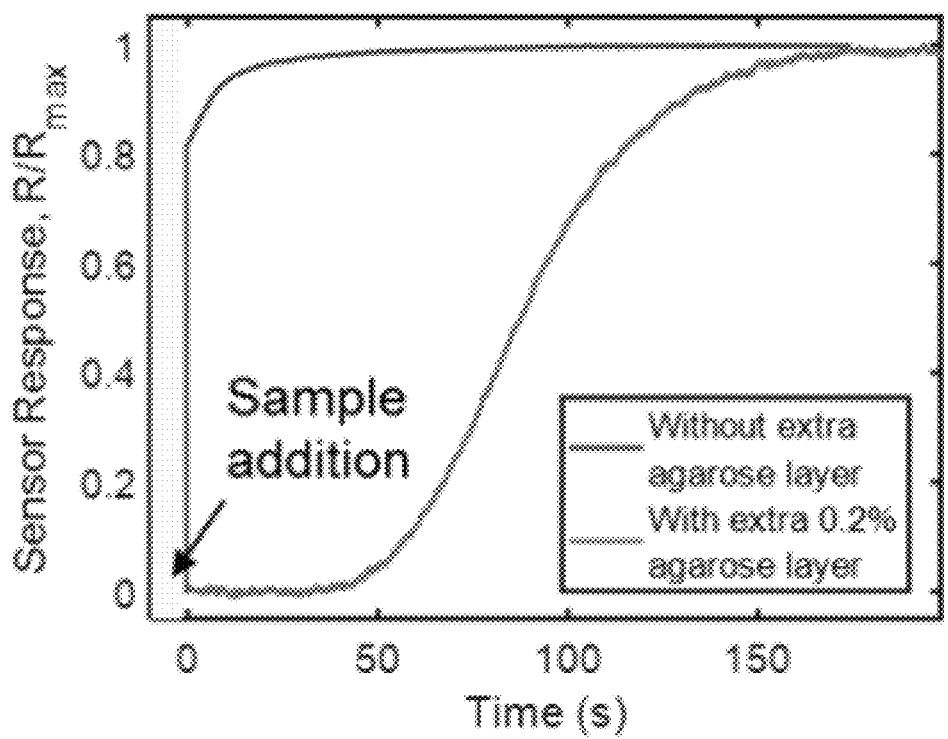

In addition, the normalized sensor response, R/R$_{max}$, was defined as the sensor response, R(t), divided by the maximum response, R$_{max}$. The results shown in FIG. 5D demonstrate that the addition of a tunable layer causes a time lag in the sensor response as well as a slowing of the sensor response dynamics. To measure the effect of the tunable layer on small molecule diffusion, the sensor response to 10 mM EDTA was measured. EDTA is known to cause a rapid turn-on response as the EDTA outcompetes the NTA groups for the Cu(II) ions so that they are no longer tethered near the SWCNT surface. In the absence of a tunable layer, addition of EDTA causes an immediate jump in the sensor signal that remains elevated over the course of several minutes (FIG. 5E). However, as shown in FIG. 5E, addition of the tunable hydrogel layer causes a time lag in the sensor response and a slowing of the response dynamics such that the sensor response levels out only after several minutes. The time scale of the experiment in FIG. 5E is on the order of the diffusive time scale for a small molecule calculated via Equation 2 below, assuming a hydrogel thickness of approximately 500 µm.

$$\tau_D = \frac{L^2}{D} \sim \frac{(500 \ \mu m)^2}{1 \times 10^5 \ cm^2/s} = 250 \ s \quad (2)$$

Model-Aided Sensor Design

In an effort to guide the design of the tunable hydrogel layer, a diffusion model was developed to predict the diffusion of monomeric, low molecular weight (LMW), and high molecular weight (HMW) species to the sensors. For this analysis, it was assumed that the protein solution was dilute and the diffusion of each species in the hydrogel was uncoupled. To estimate the diffusion coefficients, D$_{g,i}$, of all three species through the extra hydrogel layer, one of several different correlations can be used, all of which are influenced by the hydrogel pore size and protein hydrodynamic radius. See, for example, Amsden, B. Solute diffusion within hydrogels. Mechanisms and models. *Macromolecules* 31, 8382-8395, (1998), which is incorporated by reference in its entirety. Given the choice of agarose as the hydrogel material, Amsden's model was used to estimate the diffusion coefficients as described by Equation 3 below, which is an obstruction-based model that has been demonstrated to work well when describing protein diffusion in agarose hydrogels. See, for example, Amsden, B. Solute diffusion within hydrogels. Mechanisms and models. *Macromolecules* 31, 8382-8395, (1998); Amsden, B. An obstruction-scaling model for diffusion in homogeneous hydrogels. *Macromolecules* 32, 874-879, (1999); and Liang, S. M. et al. Protein diffusion in agarose hydrogel in situ measured by improved refractive index method. *J Control Release* 115, 189-196, (2006), which is incorporated by reference in its entirety.

$$\frac{D_g}{D_0} = \exp\left[-\pi\left(\frac{r_s + r_f}{k_s \varphi^{-1/2} + 2r_f}\right)^2\right] \quad (3)$$

In Equation 3, D$_0$ is the diffusion coefficient in solution (calculated using the Stokes-Einstein equation), r$_s$ is the hydrodynamic radius of the solute, r$_f$ is the radius of the polymer fiber (estimated at 19 Å)[40], $\varphi$ is the volume fraction of agarose in the gel, and k$_s$ is a hydrogel-specific scaling parameter (assumed to be 13.75 Å for agarose). The volume fraction of agarose was calculated using Equation 4, where w is the weight fraction of agarose in the gel, ρ is the density of dry agarose (1.64 g/ml) and m is the mass fraction of agarose in an agarose hydrogel fiber (0.625). See, for example, Liang, S. M. et al. Protein diffusion in agarose hydrogel in situ measured by improved refractive index method. *J Control Release* 115, 189-196, (2006); and Pluen, A., Netti, P. A., Jain, R. K. & Berk, D. A. Diffusion of macromolecules in agarose gels: Comparison of linear and globular configurations. *Biophys J* 77, 542-552, (1999), each of which is incorporated by reference in its entirety.

$$\varphi = \frac{w}{\rho \cdot m} \quad (4)$$

Figure 6A:
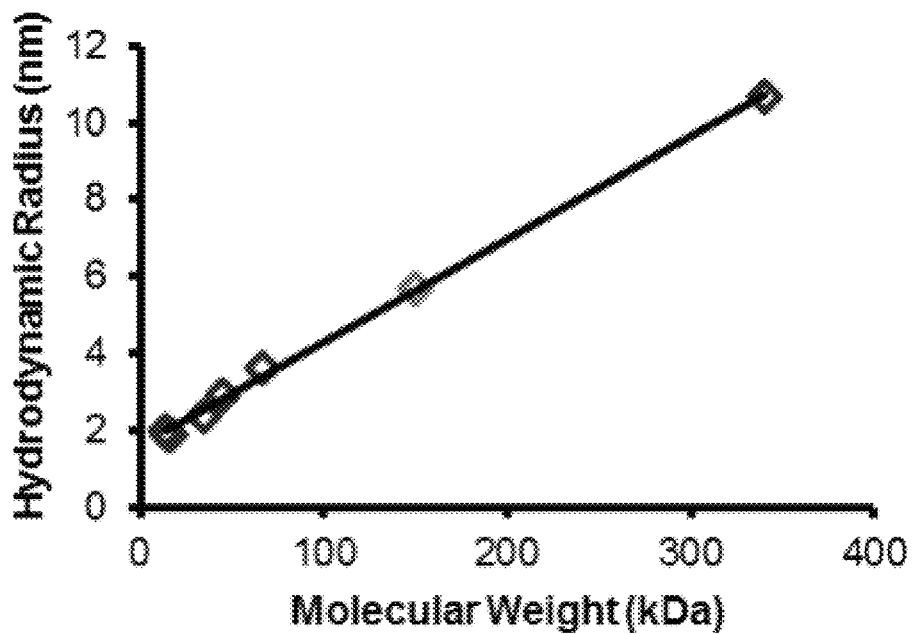
FIG. 6A shows published hydrodynamic radii of nine different proteins (IgG shown in green) versus molecular weight fitted to a linear correlation (R$^2$=0.993).

To estimate the hydrodynamic radii of various IgG$_1$ HMW or LMW species, the published hydrodynamic radii of nine different proteins (including IgG) spanning a wide range of molecular weights was plotted and fit a linear correlation (FIG. 6A). See, for example, Amsden, B. Solute diffusion within hydrogels. Mechanisms and models. *Macromolecules* 31, 8382-8395, (1998); and Pluen, A., Netti, P. A., Jain, R. K. & Berk, D. A. Diffusion of macromolecules in agarose gels: Comparison of linear and globular configurations. *Biophys J* 77, 542-552, (1999), each of which is incorporated by reference in its entirety. As an approximation during the preliminary modeling work, it was assumed that HMW species were dimers and LMW species were ½ fragments. The resulting hydrodynamic radii were approximated as 5.6 nm, 3.6 nm, and 9.6 nm for monomer, LMW, and HMW species, respectively.

For the initial model, only one-dimensional diffusion through the extra hydrogel layer was considered, governed by Equation 5 below.

$$\frac{\partial C}{\partial t} = D \frac{\partial^2 C}{\partial x^2} \quad (5)$$

Equation 5 was solved assuming x 0 at the gel-solution interface and x L at the sensors, subject to the following initial and boundary conditions.

$$C(x, 0) = 0$$

$$C(0, t) = C_0$$

$$\frac{\partial C}{\partial x}(L, t) = 0$$

Figure 6B:
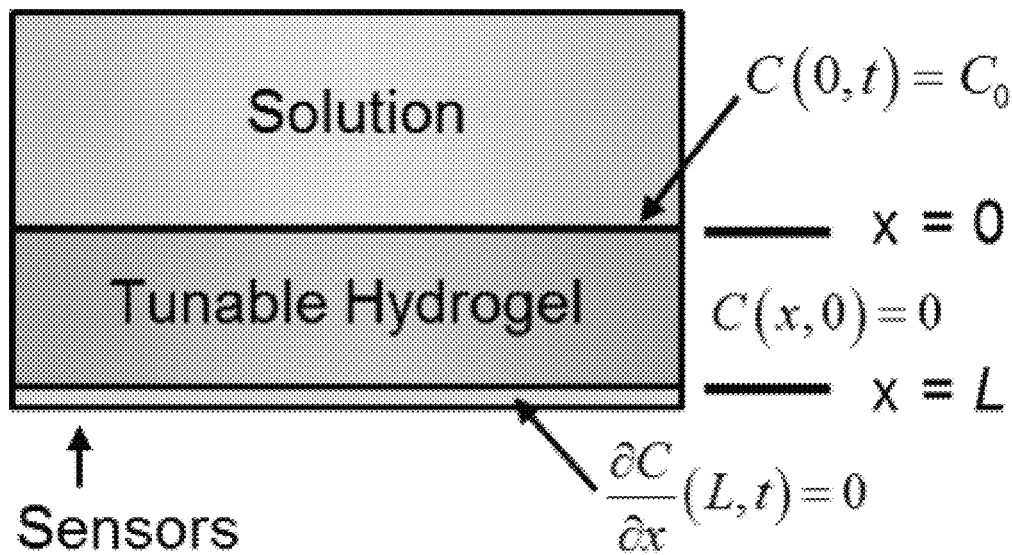
FIG. 6B shows a schematic of experimental system described by the diffusion model.

A schematic of this system is provided in FIG. 6B. Based on this formulation, the normalized concentration of species i at the sensors can be described by the following equation.

$$\frac{C_i(L, t)}{C_{i,0}} = 1 - \frac{4}{\pi} \sum_{n=0}^{\infty} \frac{(-1)^n}{2n+1} \exp\left(-\frac{D_{g,i}(2n+1)^2 \pi^2 t}{4L^2}\right) \quad (6)$$

To simulate the concentration profiles versus time of $IgG_1$ samples containing a varying distribution of monomeric, HMW, and LMW species, the compositional information collected from SE-UPLC for $IgG_1$ samples that underwent different levels of stress via UV light was used. UV light has been shown to induce both physical and chemical aggregation through the formation of chemical crosslinks, conformational changes in the protein structure, and oxidation of methionine and other residues. $IgG_1$ samples were stressed at a concentration of 100 mg/ml for 3-74 hours and the measured mass fractions of monomeric (main peak), HMW, and LMW species are provided in Table 1. See, for example, Mason, B. D., Schöneich, C. & Kerwin, B. A. Effect of pH and Light on Aggregation and Conformation of an IgG1 mAb. *Molecular Pharmaceutics* 9, 774-790 (2012); Shah, D. D., Zhang, J. M., Maity, H. & Mallela, K. M. G. Effect of photo-degradation on the structure, stability, aggregation, and function of an $IgG_1$ monoclonal antibody. *Int J Pharmaceut* 547, 438-449, (2018); Cockrell, G. M., Wolfe, M. S., Wolfe, J. L. & Schoneich, C. Photoinduced aggregation of a model antibody-drug conjugate. *Molecular Pharmaceutics* 12, 1784-1797 (2015); Liu, D. et al. Structure and stability changes of human IgG1 Fc as a consequence of methionine oxidation. *Biochemistry* 47, 5088-5100 (2008); and Lorenz, C. M. et al. The Effect of Low Intensity Ultraviolet-C Light on Monoclonal Antibodies. *Biotechnol Progr* 25, 476-482, doi:10.1021/bp.157 (2009), each of which is incorporated by reference in its entirety.

TABLE 1

SE-UPLC data from UV light-stressed $IgG_1$ samples providing the fraction of unaffected sample (monomer), high molecular weight aggregates (HMW), and low molecular weight fragments.

| Stress | Mass Fraction | | |
|---|---|---|---|
| Duration (h) | Monomer | HMW | LMW |
| 0 | 0.973 | 0.0037 | 0.0232 |
| 3 | 0.9535 | 0.0241 | 0.0225 |
| 7 | 0.9391 | 0.0389 | 0.022 |
| 26 | 0.8584 | 0.1214 | 0.0203 |
| 45 | 0.7764 | 0.2036 | 0.02 |
| 74 | 0.6483 | 0.3065 | 0.0452 |

Using the SE-UPLC data, it was possible to simulate the total molar concentration profile of a given $IgG_1$ sample as the weighted sum of the profiles for individual protein species, as shown by Equation 7.

$$\frac{C}{C_0}(L, t) = \alpha_M \left(\frac{C}{C_0}\right)_M + \alpha_{HMW} \left(\frac{C}{C_0}\right)_{HMW} + \alpha_{LMW} \left(\frac{C}{C_0}\right)_{LMW} \quad (7)$$

In Equation 7, the three $\alpha_i$ parameters pertain to the mole fractions of monomer (M), HMW, and LMW species calculated from Table 1.

With the diffusion model fully developed, two performance metrics of the tunable hydrogel layer were defined: (A) the maximum concentration resolution and (B) the response time as defined below:

$$\text{Criteria } A: \Delta C_{max} = \max_t \left[\left(\frac{C}{C_0}\right)_{0h} - \left(\frac{C}{C_0}\right)_{45h}\right]$$

$$\text{Criteria } B: t_{max} = \text{time at which } (\Delta C = \Delta C_{max})$$

Figure 6C:
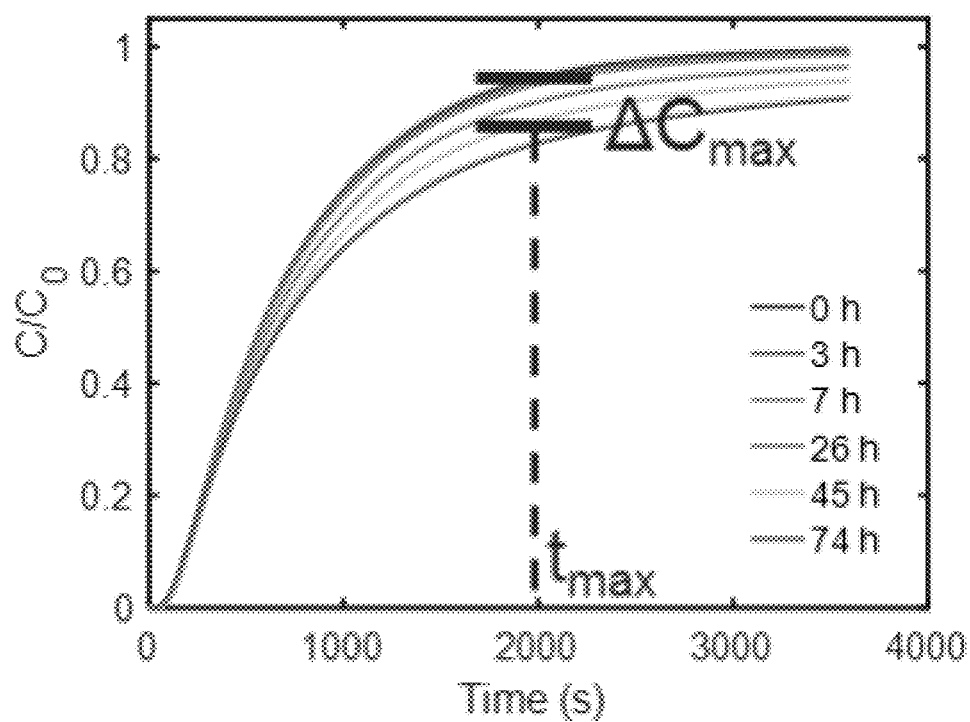
FIG. 6C shows graphical definition of $\Delta C_{max}$ and $t_{max}$. Concentration profiles at the agarose conditions of (FIG. 6D) 600 μm thickness, 0.2% concentration, and (FIG. 6E) 100 μm thickness, 3% concentration.

A graphical definition of these two parameters is provided in FIG. 6C. The optimal separation performance pertains to a large value of $\Delta C_{max}$ and a small value of $t_{max}$. While the definition of $\Delta C_{max}$ is somewhat arbitrary regarding which two samples are being compared, the 45-hour stressed material was chosen as a reference given that the concentration of LMW species in the 74-hour stressed sample was anomalously high relative to the other samples (Table 1). In addition, using less stressed material as a reference sample would yield the same overall trends, albeit different values of $\Delta C_{max}$ and $t_{max}$.

Figure 6D:
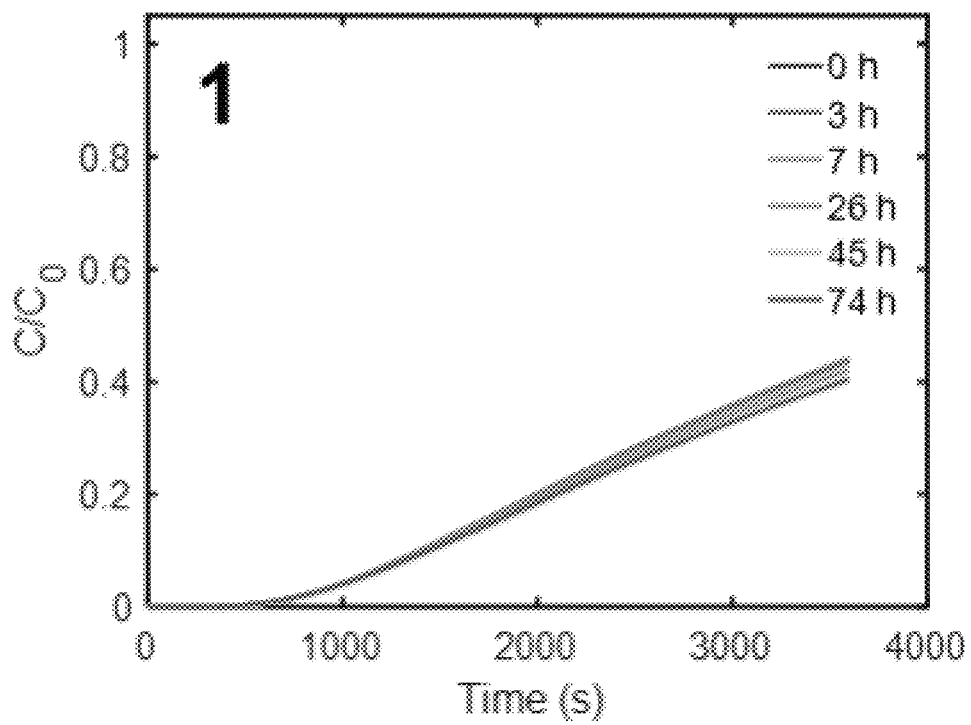
FIG. 6F shows simulated separation performance at various agarose concentrations and thicknesses of the extra tunable hydrogel layer.
FIG. 6G shows simulated time of maximum separation performance at various agarose concentrations and thicknesses.
Figure 6E:
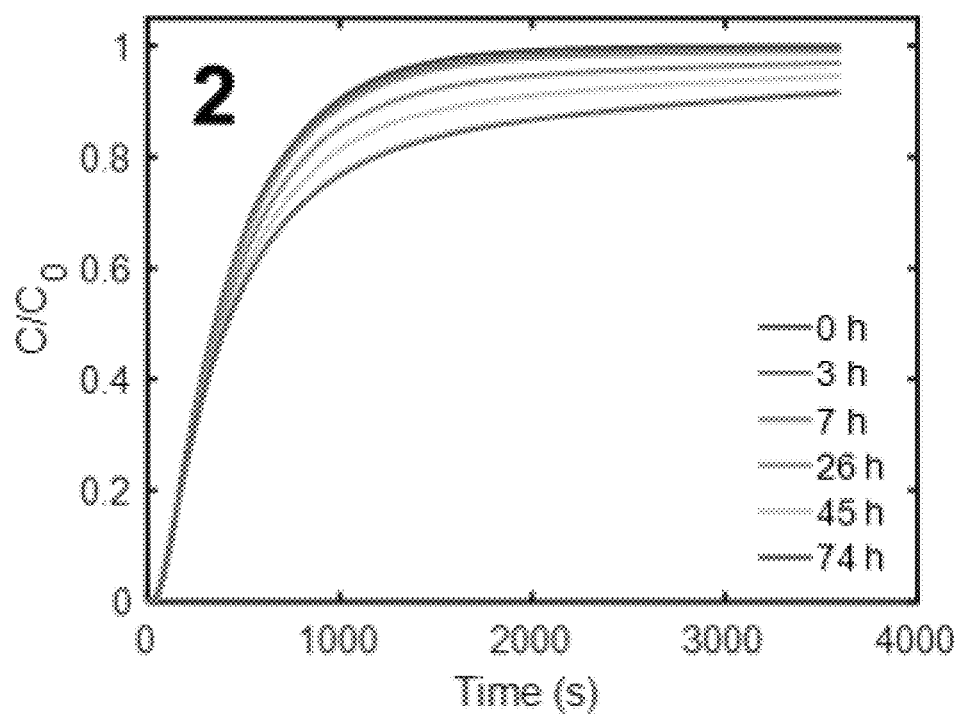
Figure 6F:
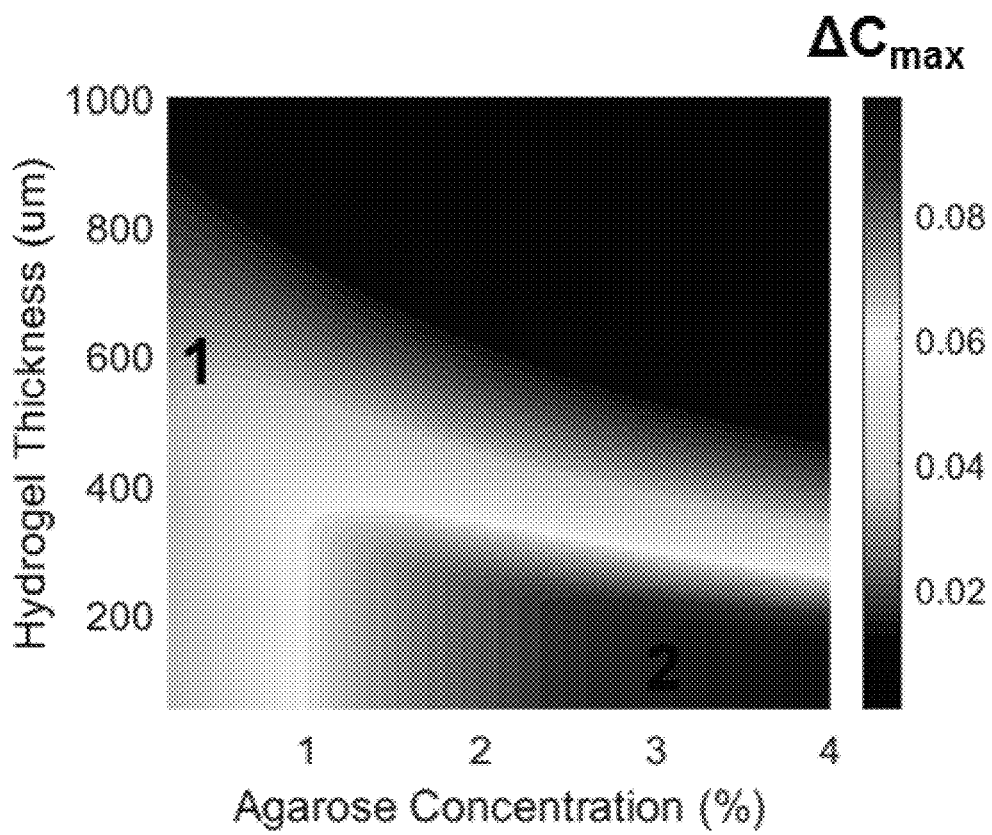
Figure 6G:
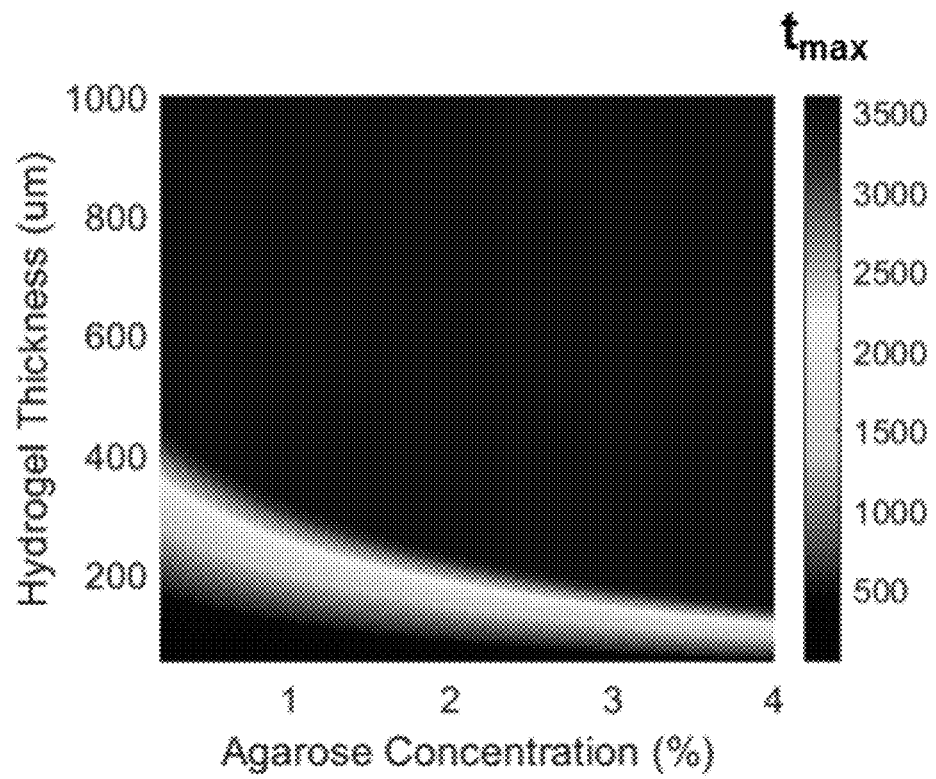

In the case of choosing agarose as the hydrogel material, the two hydrogel properties that influence analyte diffusion are the concentration (i.e., pore size) and thickness. As a result, hydrogel properties were systematically varied, simulated concentration profiles over the course of one hour, and generated maps of separation performance, as shown in FIG. 6F and FIG. 6G. The results indicate that separation performance, on a concentration basis, is optimized when using tunable hydrogel layers of high agarose concentration and low thickness. FIG. 6D and FIG. 6E provide concentration profiles of the various stressed samples under the conditions represented by the numbers 1 and 2 in FIG. 6F, respectively. Note that the results shown in FIG. 6F and FIG. 6G are influenced by the fact that the concentrations for up to one hour were simulated. Thus, the $\Delta C_{max}$ values plotted indicate the maximum separation over the course of an hour, not the maximum separation possible at a given set of agarose pore size and thickness.

While the preceding results indicate that a thin and concentrated agarose gel would achieve optimal separation performance in terms of the total concentration at the sensors, the dependence observed in FIG. 6F does not necessarily correspond to maximum sensor discrimination. In the case of SWCNT nIR fluorescent sensors, analyte diffusion must be coupled with sensor binding at the hydrogel boundary. For this model, it was assumed that a monovalent binding reaction between all $IgG_1$ species and the sensors (θ). Moreover, it was assumed that the sensors did not consume enough analyte to modify the analyte concentration profile and further aggregation did not take place in the hydrogel. This results in the binding reaction given below.

$$IgG + \theta \underset{k_r}{\overset{k_f}{\rightleftarrows}} IgG - \theta$$

The concentration of each bound $IgG_1$ species can be described by Equation 8.

$$\frac{d[IgG-\theta]}{dt} = k_f[IgG](\theta_T - [IgG-\theta]) - k_r([IgG-\theta]) \quad (8)$$

Normalizing each term in (8) by the total sensor concentration, $\theta_T$, yields Equation 9, which describes the fraction of bound sensor sites, f. This can ultimately be related to the sensor response, R, via Equation 10 where $R_{max}$ is equal to the maximum sensor response.

$$\frac{df}{dt} = k_f[IgG](1-f) - k_r f \quad (9)$$

$$R = R_{max} \cdot f \quad (10)$$

Figure 7A:
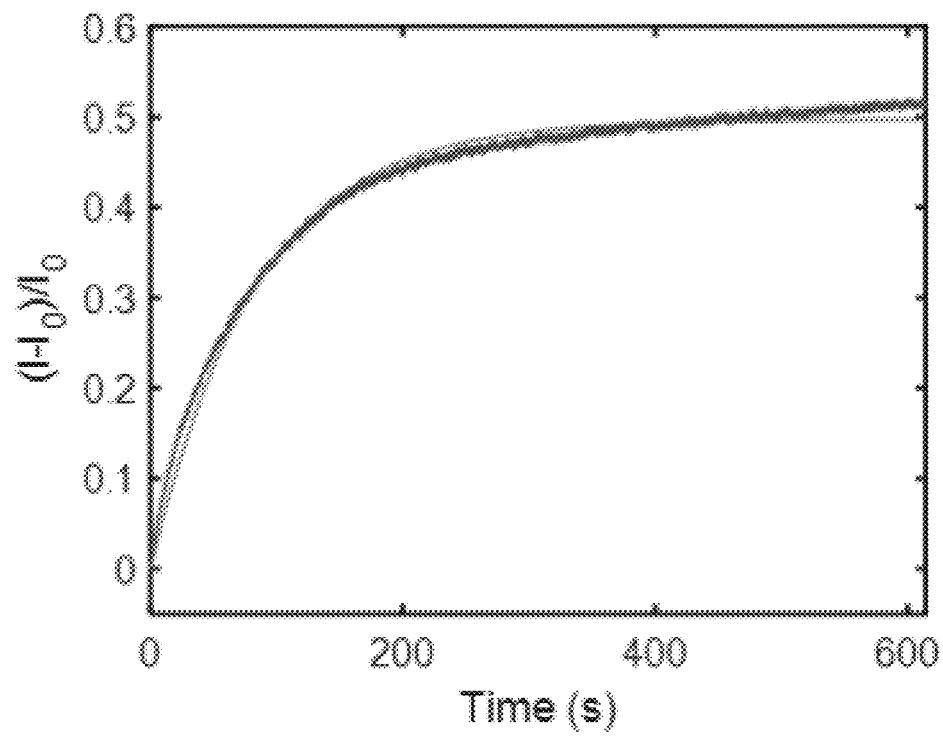
FIG. 7A shows dynamic sensor binding data for 10 mg/ml unstressed IgG$_1$ collected without an extra hydrogel layer, along with a fit to a 1:1 sensor binding model.
Figure 7B:
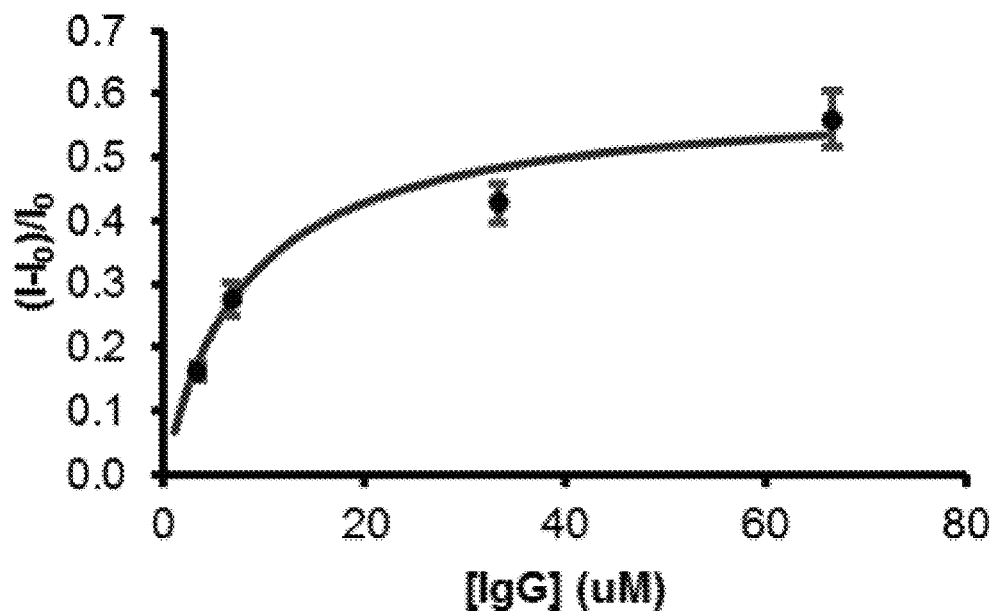
FIG. 7B shows equilibrium sensor response data without an extra hydrogel layer at different IgG$_1$ concentrations, along with a fit to a 1:1 binding model. Error bars represent the standard deviations from three replicates.

To simulate the sensor response, Equation 9 was coupled to the analyte diffusion model and solved numerically using the forward Euler method with a time step of one second. Based on data collected in the absence of a tunable layer using unstressed $IgG_1$, sensor parameter values of 0.6, 130 $M^{-1}$ $s^{-1}$, and 8 μM for $R_{max}$, $k_f$, and $K_D$, respectively (FIG. 7A and FIG. 7B) were used.

With the combined diffusion and sensor binding model, separation performance parameters were defined based on the sensor output.

$$\Delta R_{max} = \max_t \left[ \frac{R_{0h}}{R_{max}} - \frac{R_{45h}}{R_{max}} \right]. \quad A$$

$$t_{R,max} = \text{time at which } (\Delta R = \Delta R_{max}). \quad B$$

Figure 7C:
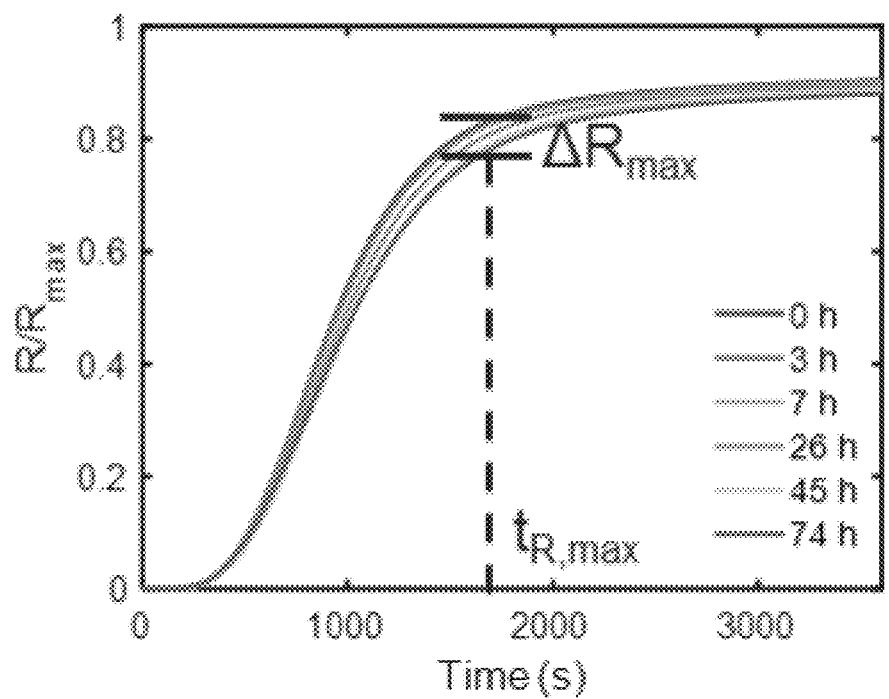
FIG. 7C shows graphical definition of $\Delta R_{max}$ and $t_{R,max}$. Simulated sensor responses at the agarose conditions of (FIG. 7D) 600 μm thickness, 0.2% concentration, and (FIG. 7E) 100 μm thickness, 3% concentration.
Figure 7D:
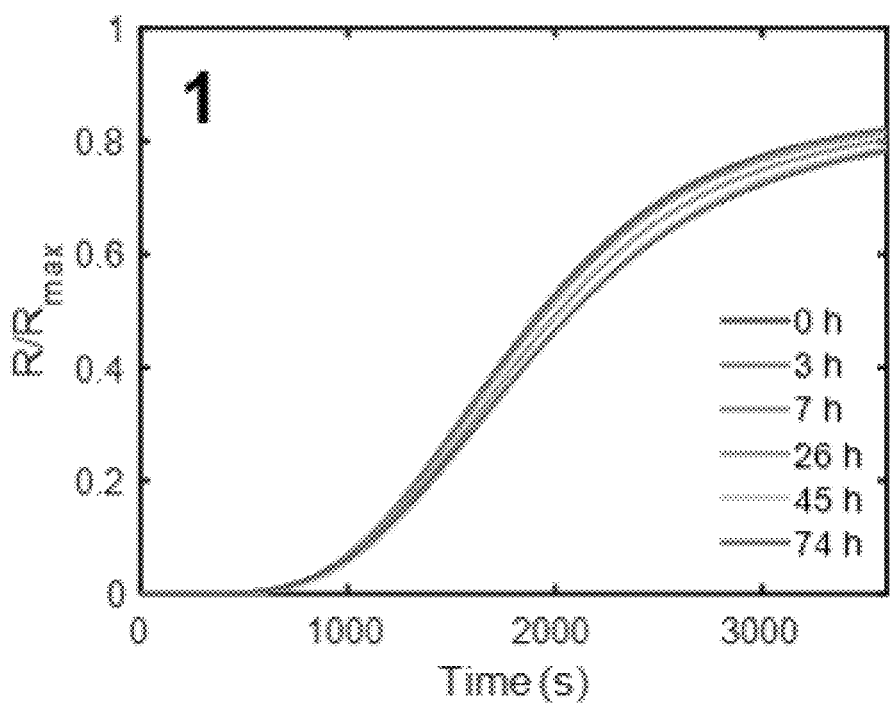
FIG. 7F shows simulated sensor response separation performance at various agarose concentrations and thicknesses of the extra tunable hydrogel layer.
FIG. 7G shows simulated time of maximum sensor response separation performance at various agarose concentrations and thicknesses.
Figure 7E:
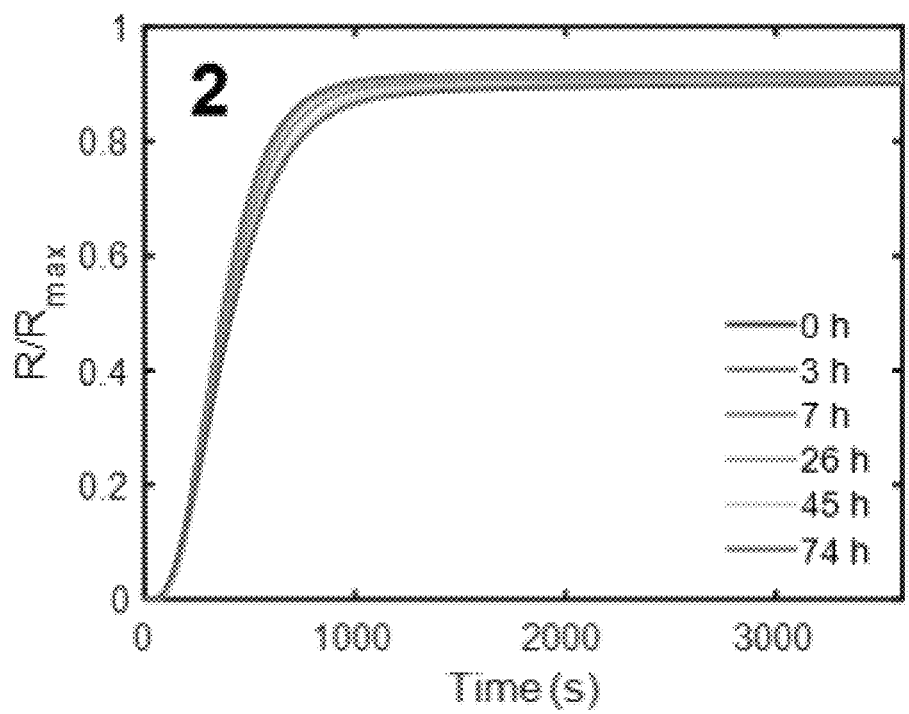
Figure 7F:
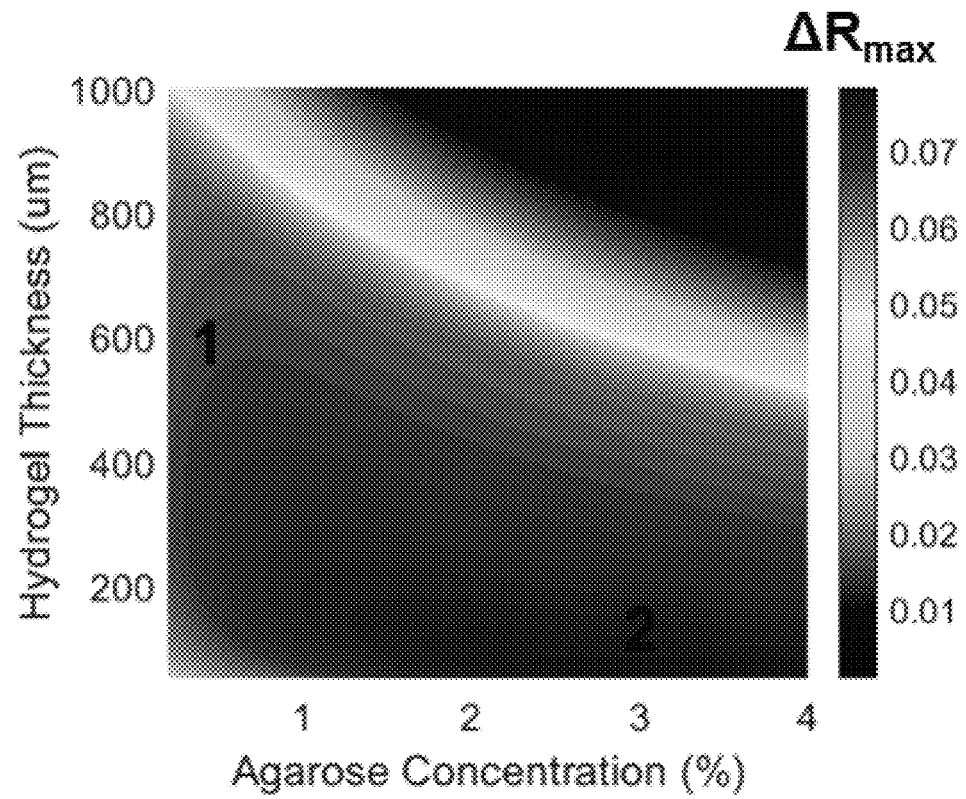
Figure 7G:
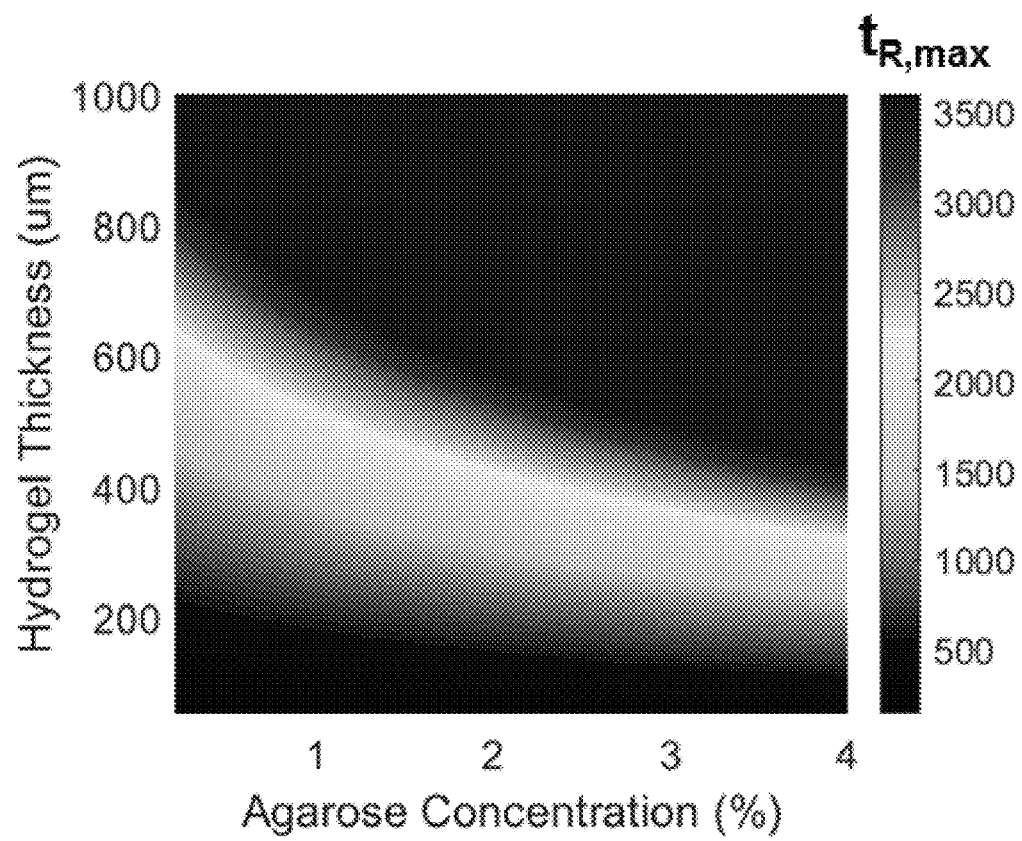

A graphical definition of these two parameters is provided in FIG. 7C. Sensor responses were simulated assuming a bulk $IgG_1$ concentration of 10 mg/ml. Molar concentrations of $IgG_1$ were calculated using the average molecular weight approximated from the SE-UPLC data. Surprisingly, incorporation of the sensor binding model significantly smears the optimal regions of the performance maps, as shown in FIG. 7F and FIG. 7G. FIG. 7D and FIG. 7E provide the simulated sensor responses at the same conditions as FIG. 6D and FIG. 6E, respectively. The maximum separation in sensor response is similar across many gel thicknesses and concentrations, with the main difference being the time at which the maximum separation is achieved (FIG. 7G).

Application of the Model to Experimental Data

In addition to using the previously developed model to guide sensor design, application of the model to experimental data in order to extract compositional information was ultimately of interest. Based on the results shown in FIGS. 7A-7G, the same agarose concentration in the tunable layer was used as was used in the base layer (0.2%). A comparison of the sensor binding curves obtained from different agarose concentrations is provided in FIGS. 13-17B.

Figure 8A:
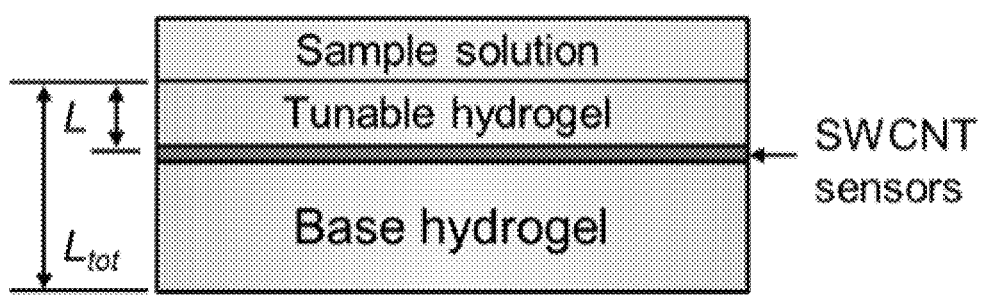
FIG. 8A shows a schematic of experimental system where a single tunable hydrogel thickness is assumed.

The schematic of the experimental system, shown in FIG. 8A, can be described by the following solution to the diffusion equation, where $L_{tot}$ is the total thickness of the tunable and base layers. The thickness of the base layer was estimated by dividing the volume of the base layer by the cross-sectional area of the well bottom.

$$\frac{C(L,t)}{C_0} = \quad (11)$$

$$1 - \frac{4}{\pi} \sum_{n=0}^{\infty} \frac{(-1)^n}{2n+1} \exp\left(-\frac{D(2n+1)^2\pi^2 t}{4L_{tot}^2}\right) \cos\left(\frac{(2n+1)\pi(L_{tot}-L)}{2L_{tot}}\right)$$

Figure 8B:
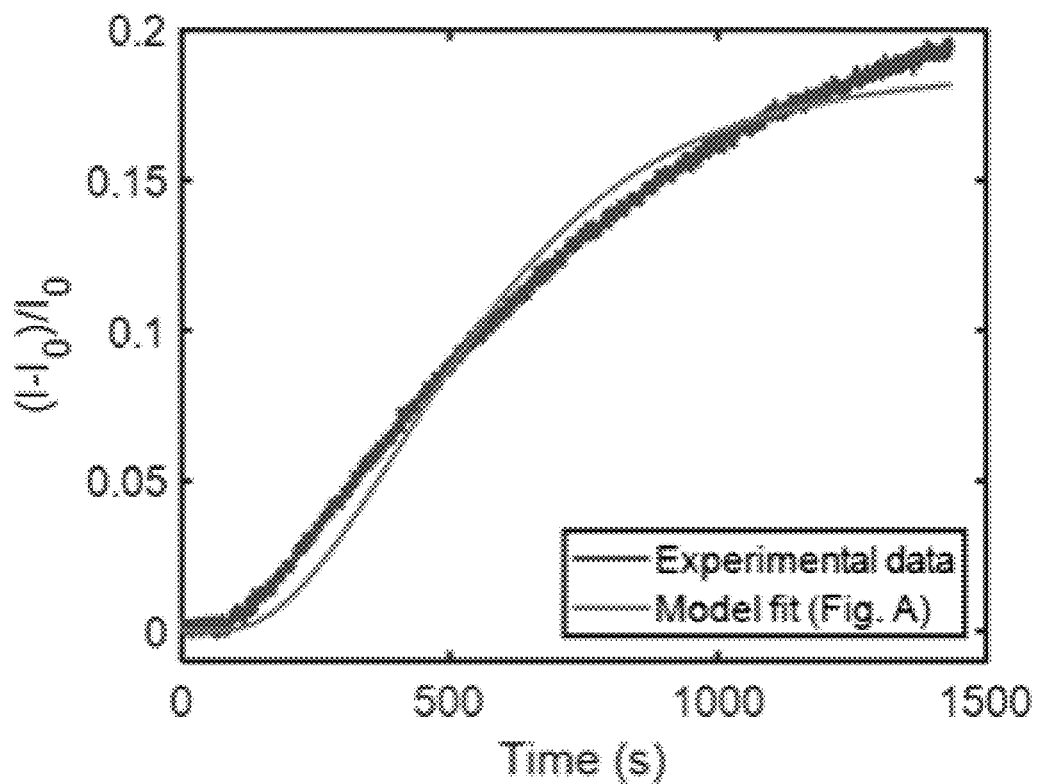
FIG. 8B shows a fit of the single-thickness model (Equation 11) to experimental binding data collected for 10 mg/ml unstressed human IgG$_1$ using a tunable layer of 30 μL 0.2% agarose in a 96-well plate.

This equation was coupled to the sensor binding model discussed previously and fit experimental data collected from 10 mg/ml unstressed $IgG_1$ using a tunable layer of 30 μL of 0.2% agarose. The composition of the $IgG_1$ sample was specified based on the SE-UPLC data and the thickness of the tunable layer, L, and the maximum sensor response, $R_{max}$, was fit. The experimental data and resulting fit are shown in FIG. 8B. While the coefficient of determination was calculated to be 0.986, systematic deviations between the experimental data and model fit can be observed. Specifically, it was found that the as-formulated model predicts a larger time lag than was experimentally observed, in addition to faster response dynamics after the time lag. This result was consistent across all experiments.

Figure 8C:
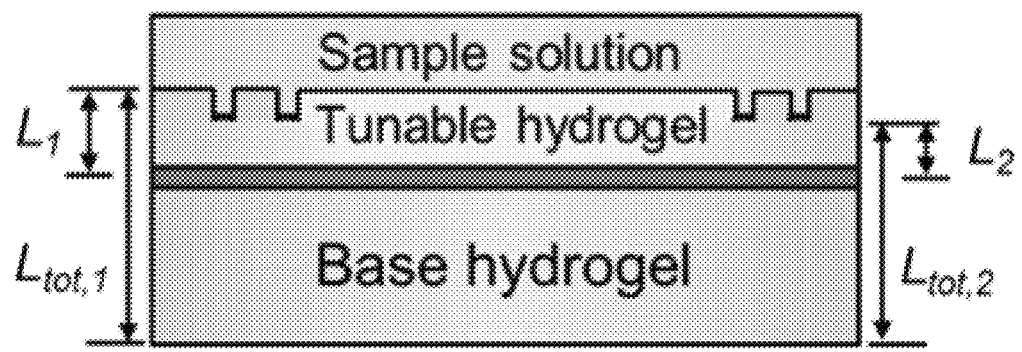
FIG. 8C shows a schematic of experimental system described by a two-thickness model that accounts for cracks that form within the hydrogel layer during casting and/or heterogeneity in the hydrogel thickness.

To address the systematic deviations observed in FIG. 8B, a revised diffusion model was developed that accounts for heterogeneity in the thickness of the tunable layer by approximating the system as having two effective thicknesses (FIG. 8C). Heterogeneity in the tunable layer thickness could be caused by several factors including the formation of a meniscus with the well plate wall, as well as incomplete spreading of the agarose layer due to viscosity effects. The average concentration at the sensors could then be specified by an additional parameter, β, according to the following equation.

$$\frac{C}{C_0}(t) = (1-\beta) \cdot \left(\frac{C}{C_0}\right)_{L1} + \beta \cdot \left(\frac{C}{C_0}\right)_{L2} \quad (12)$$

Figure 8D:
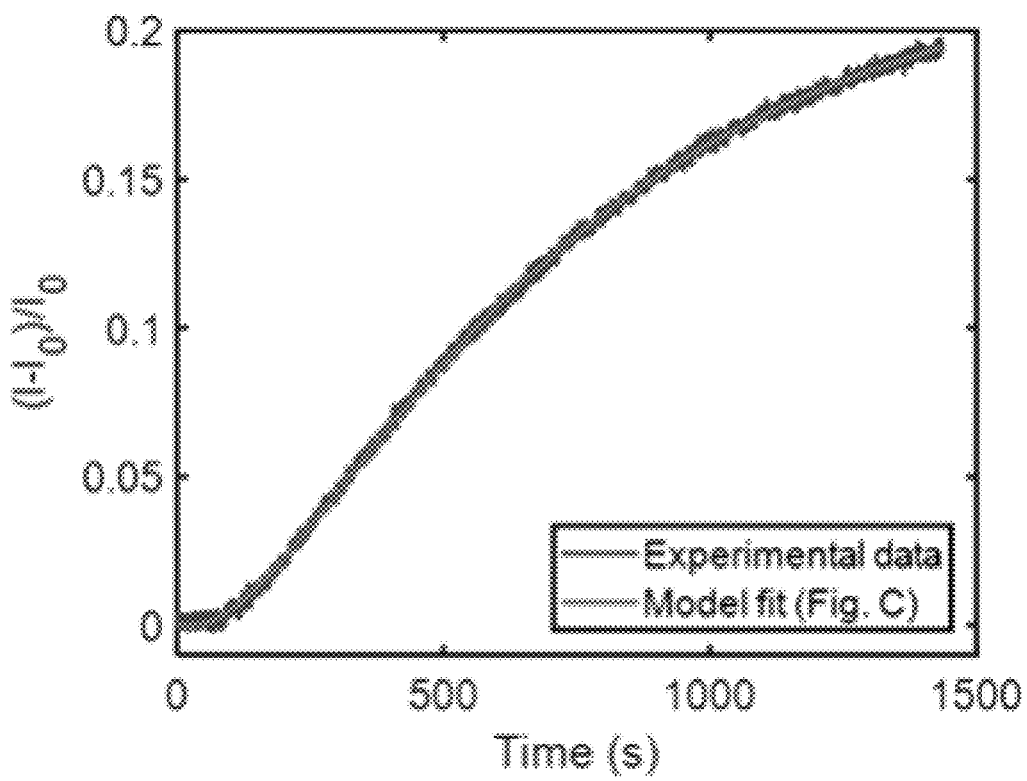
FIG. 8D shows a fit of the two-thickness model (Equations 11 and 12) to the same experimental data shown in FIG. 8B.
Figure 9A:
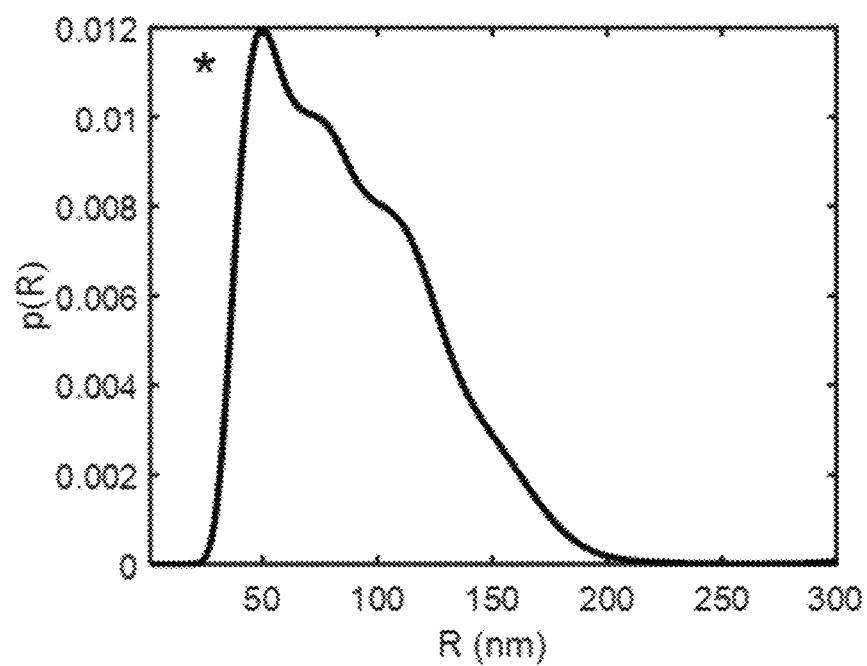
FIGS. 9A-9F show particle size distributions obtained from nanoparticle tracking analysis for (FIG. 9A) unstressed IgG$_1$, (FIG. 9B) 3-hour stressed IgG$_1$, (FIG. 9C) 7-hour stressed IgG$_1$, (FIG. 9D) 26-hour stressed IgG$_1$, (FIG. 9E) 45-hour stressed IgG$_1$, and (FIG. 9F) 74-hour stressed IgG$_1$. The asterisks denote the peak associated with buffer impurities.
Figure 9B:
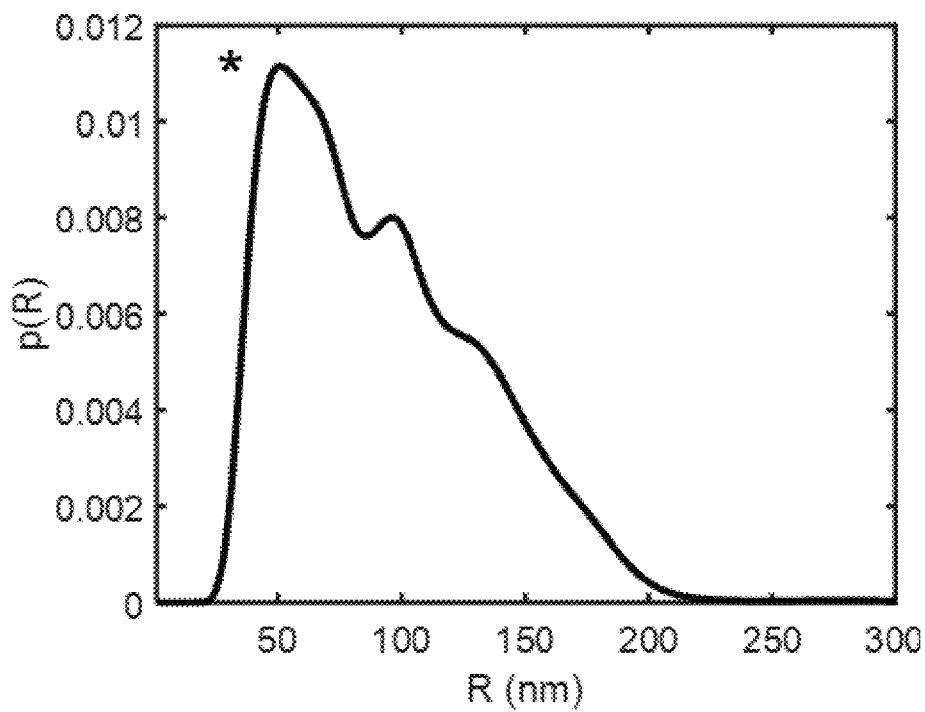
Figure 9C:
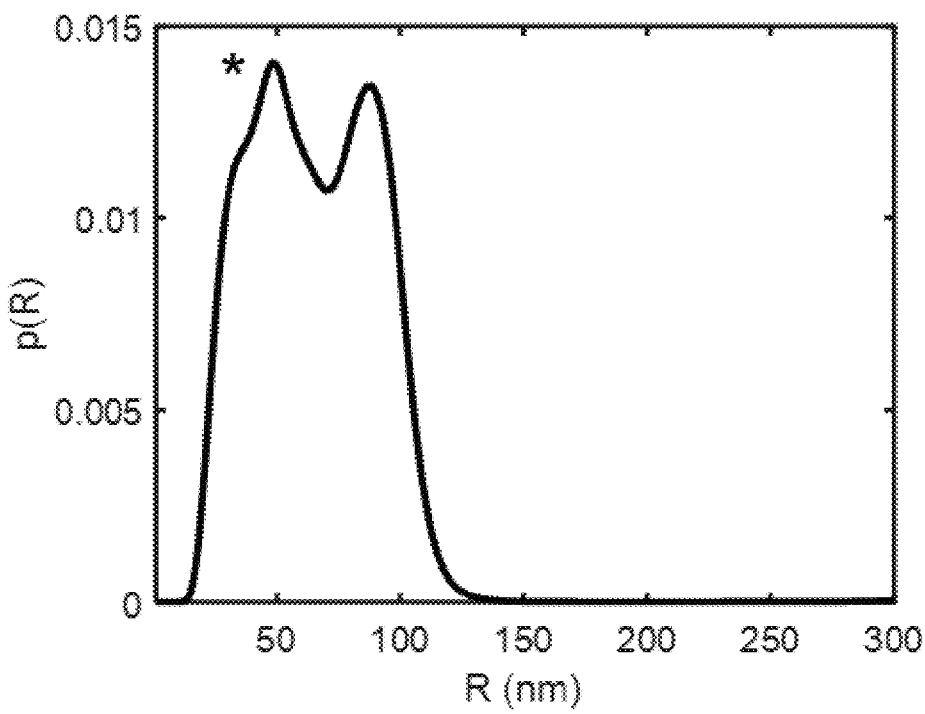
Figure 9D:
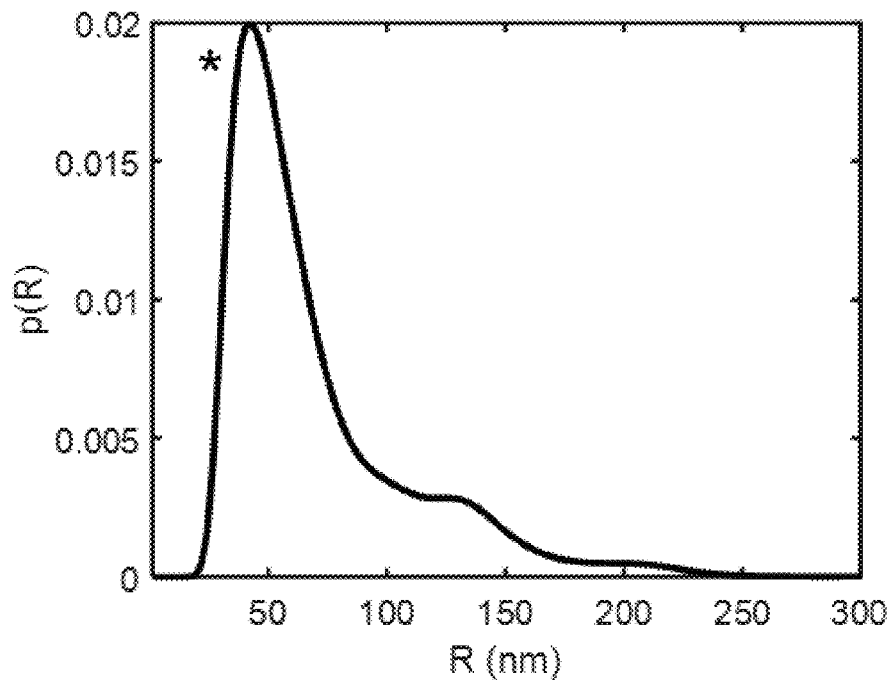
Figure 9E:
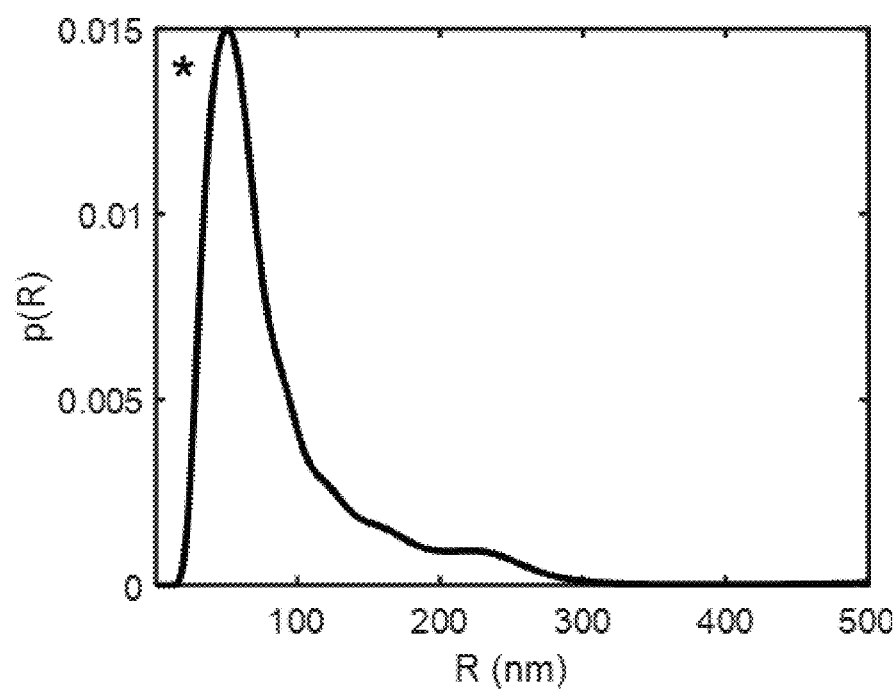
Figure 9F:
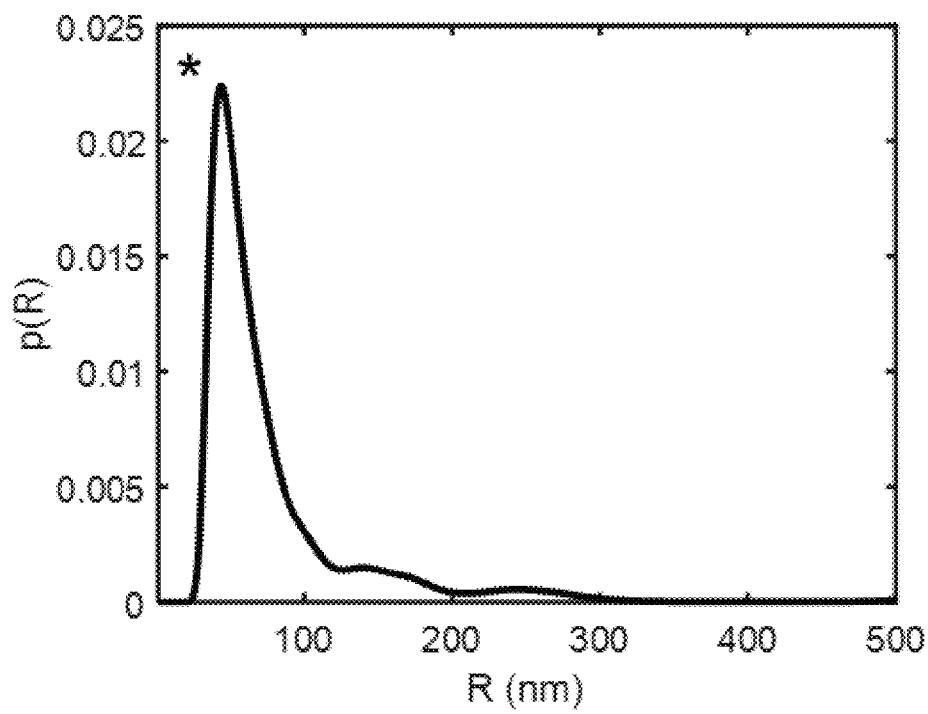

In Equation 12, $$\left(\frac{C}{C_0}\right)_{L1} \text{ and } \left(\frac{C}{C_0}\right)_{L2}$$

pertain to concentration profiles calculated from Equation 11 using tunable layer thicknesses of $L_1$ and $L_2$, respectively (FIG. 8C). As shown in FIG. 8D, this revised model provides a significantly improved fit of the experimental data (coefficient of determination equal to 0.9995).

Characterization of stressed $IgG_1$ samples

To supplement the SE-UPLC data and further elucidate the size distributions of the stressed $IgG_1$ material, nanoparticle tracking analysis on the stressed samples was performed, which can identify aggregate species between 30 nm and 1 μm. $IgG_1$ samples were characterized at a nominal concentration of 200 μg/ml and particle trajectory data was analyzed using the MApNTA algorithm that was introduced and implemented in Matlab. The resulting normalized particle size distributions are provided in FIGS. 9A-9F and clearly show a change in aggregate size and concentration with stress level. In particular, there is a significant change in the particle size distribution between 7 hours and 26 hours of UV stress, where it appears as though smaller aggregates may coalesce into larger species. The main peak at about 50 nm is attributed to components in the $IgG_1$ buffer, as this peak was present when testing buffer in the absence of protein (provided in FIGS. 13-17B). The particles to originate from excipients added to the formulation buffer, including sucrose, which have previously been detected and attributed to raw material impurities. See, for example, Weinbuch, D. et al. Nanoparticulate Impurities in Pharmaceutical-Grade Sugars and their Interference with Light Scattering-Based Analysis of Protein Formulations. *Pharm Res-Dordr* 32, 2419-2427, (2015), which is incorporated by reference in its entirety.

Figure 10A:
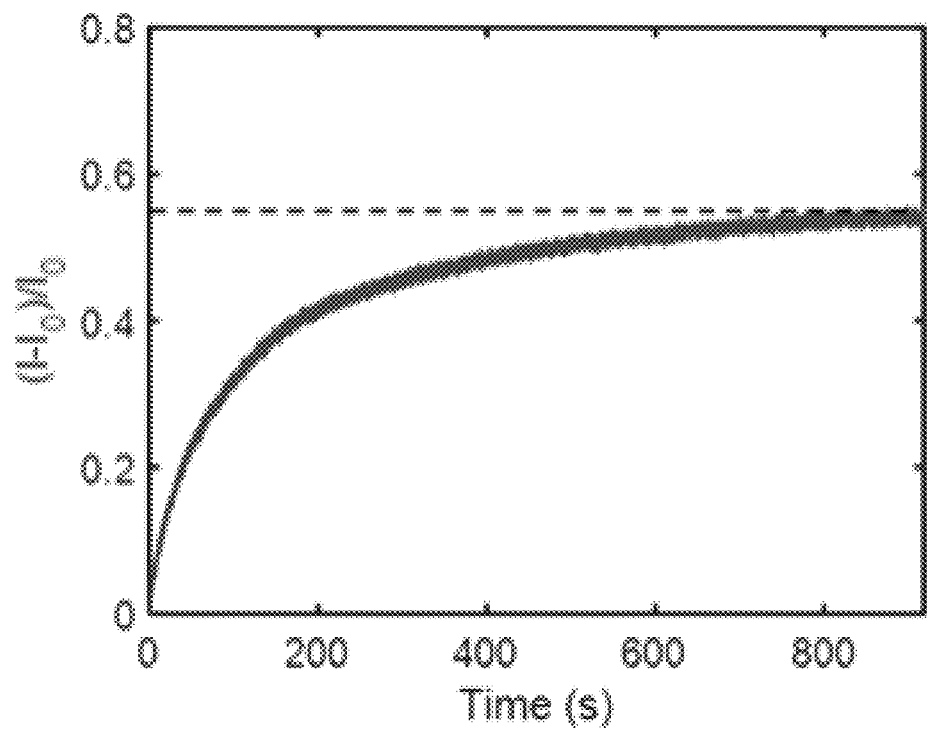
FIGS. 10A-10F show response of protein A-loaded sensors to 10 mg/ml (FIG. 10A) unstressed IgG$_1$, (FIG. 10B) 3-hour stressed IgG$_1$, (FIG. 10C) 7-hour stressed IgG$_1$, (FIG. 10D) 26-hour stressed IgG$_1$, (FIG. 10E) 45-hour stressed IgG$_1$, and (FIG. 10F) 74-hour stressed IgG$_1$. Experiments were performed without an extra tunable layer and the dotted black lines denote the maximum sensor response.
Figure 10B:
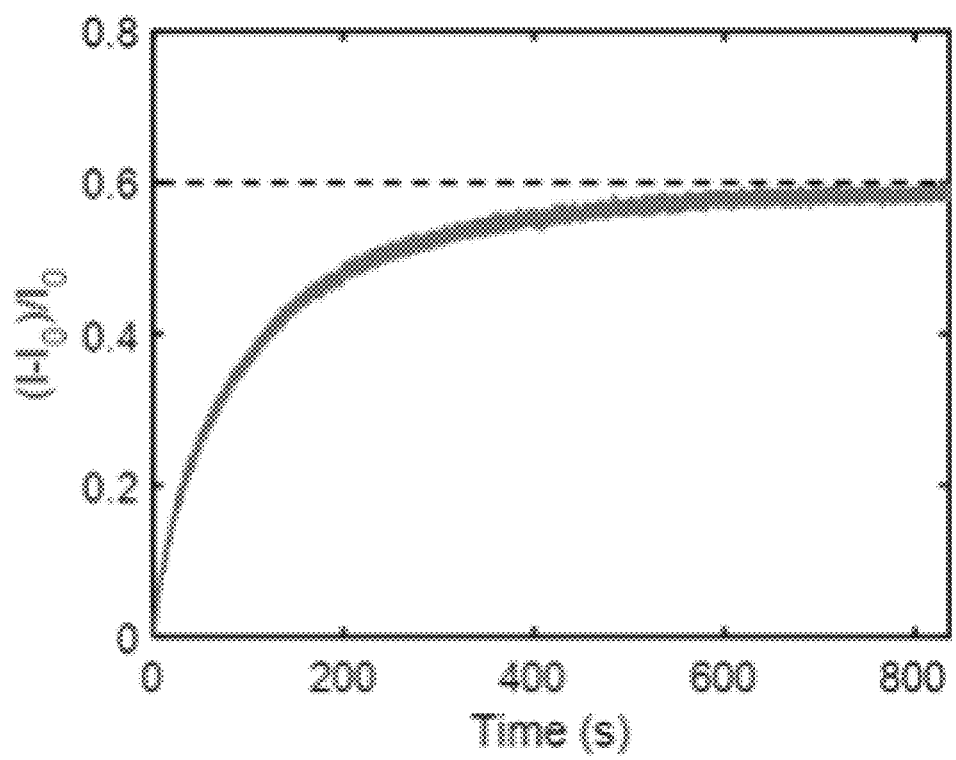
Figure 10C:
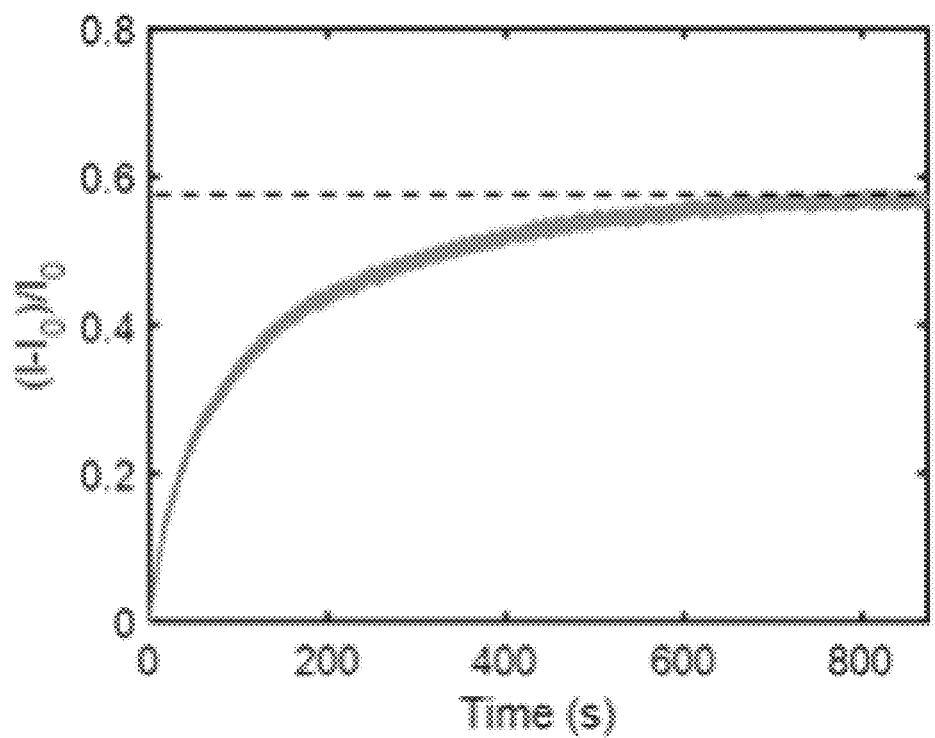
Figure 10D:
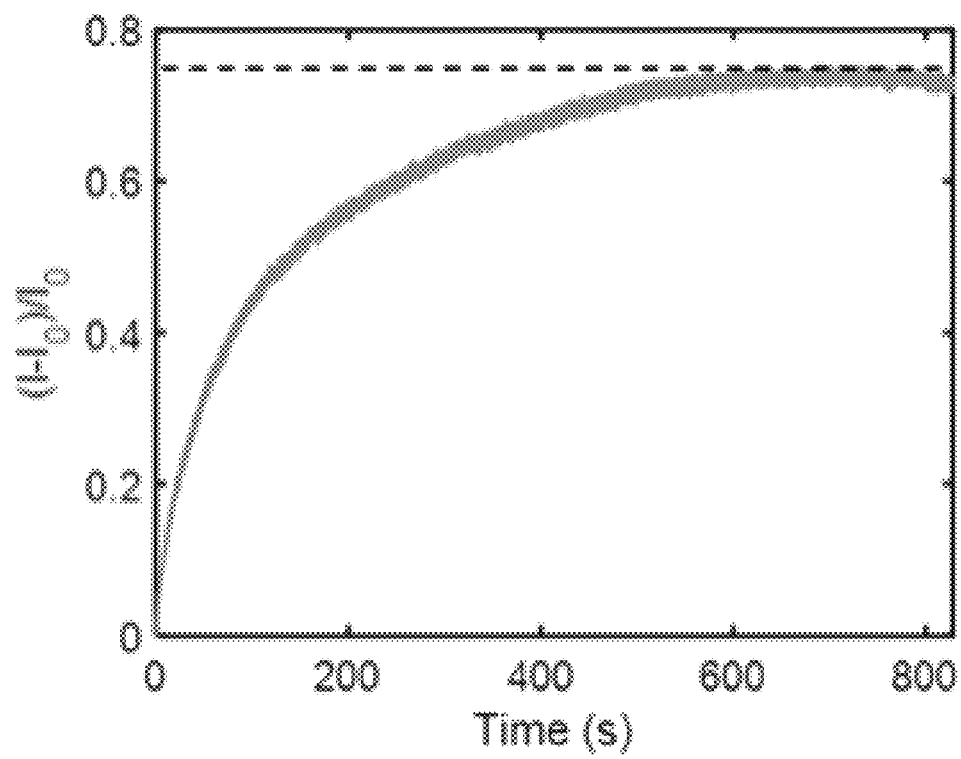
Figure 10E:
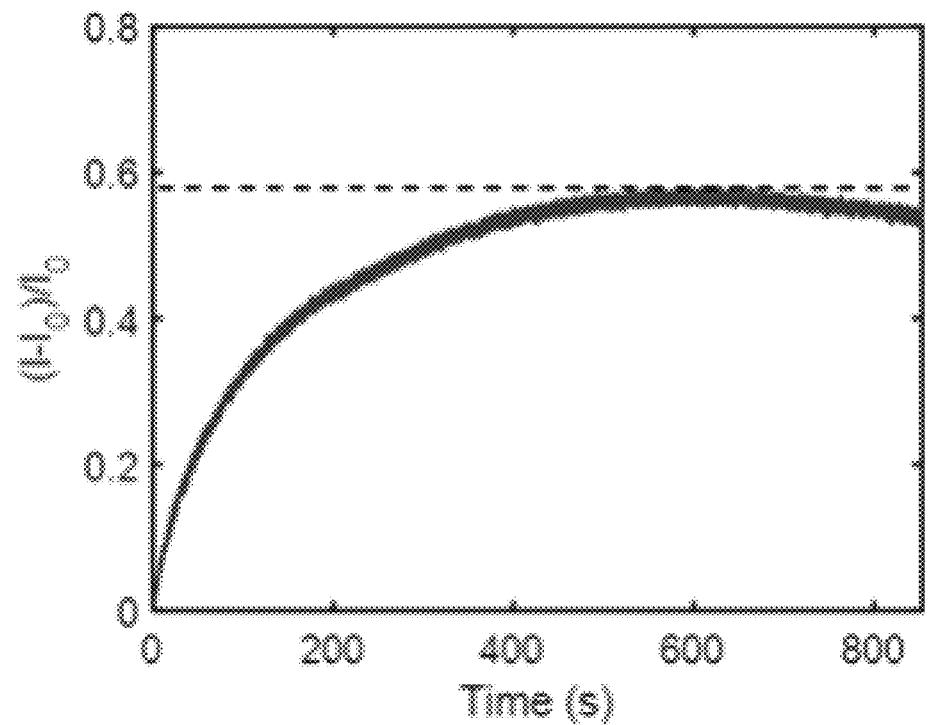
Figure 10F:
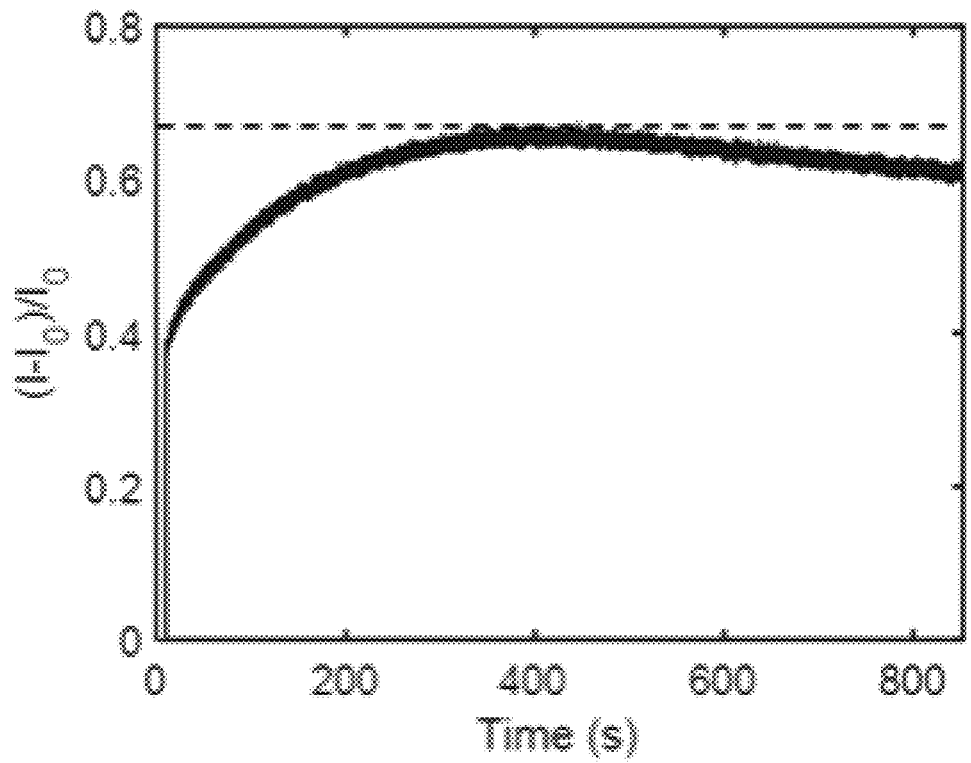

The response of protein A-loaded SWCNT sensors to the stressed $IgG_1$ samples were first evaluated in the absence of an extra tunable layer. All samples were tested at a nominal concentration of 10 mg/ml, and representative binding curves are provided in FIGS. 10A-10F for all six samples. While lower stressed sample responses leveled out, 26-hour, 45-hour, and 74-hour stressed samples began to decrease at long times (FIGS. OD-OF). Furthermore, addition of the 74-hour stressed material caused an immediate, discontinuous sensor response followed by a smaller binding curve (FIG. 10F). While the reason for this response behavior is currently unknown, it is likely that the highly stressed samples contain a high concentration of oxidized species, which have been shown to bind differently to protein A and protein G. See, for example, Gaza-Bulseco, G., Faidu, S., Hurkmans, K., Chumsae, C. & Liu, H. C. Effect of methionine oxidation of a recombinant monoclonal antibody on the binding affinity to protein A and protein G. *J Chromatogr B* 870, 55-62, (2008), which is incorporated by reference in its entirety. Moreover, the SE-UPLC results in Table 1 indicate that the concentration of LMW species is twice as high in the 74-hour stressed sample versus the other samples, which may have also contributed to the anomalous sensor binding curve shown in FIG. 10F. For samples that underwent low levels of stress, differences in the sensor response magnitude were attributed to variation in the concentration of the $IgG_1$ stock solutions, which was determined to be ±15% based on absorbance measurements.

Figure 11A:
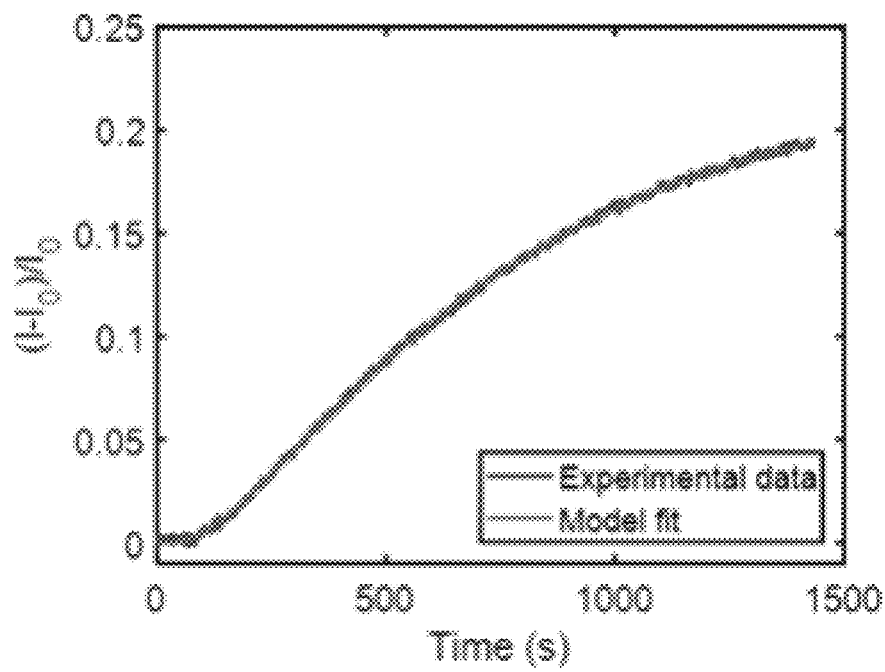
FIGS. 11A-11E show sensors response to 10 mg/ml (FIG. 11A) unstressed IgG$_1$, (FIG. 11B) 3-hour stressed IgG$_1$, and (FIG. 11C) 7-hour stressed IgG$_1$, with a tunable hydrogel layer of 30 μL of 0.2% agarose.
Figure 11B:
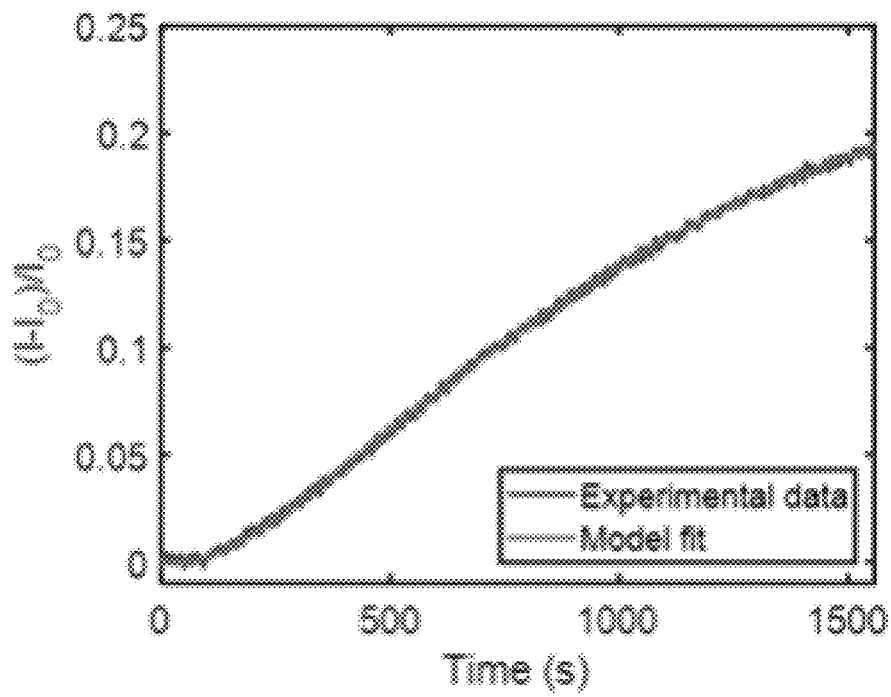
Figure 11C:
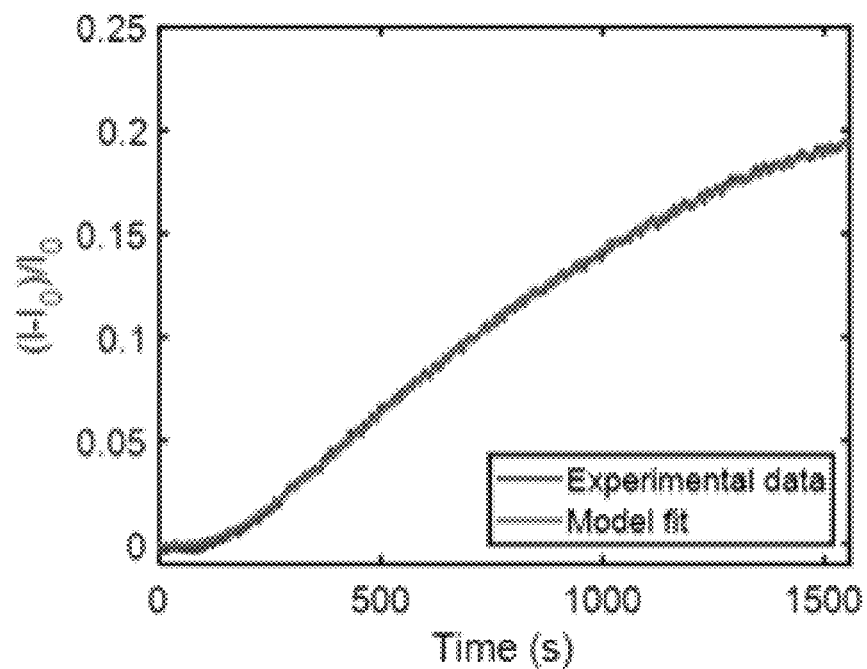
Figure 11D:
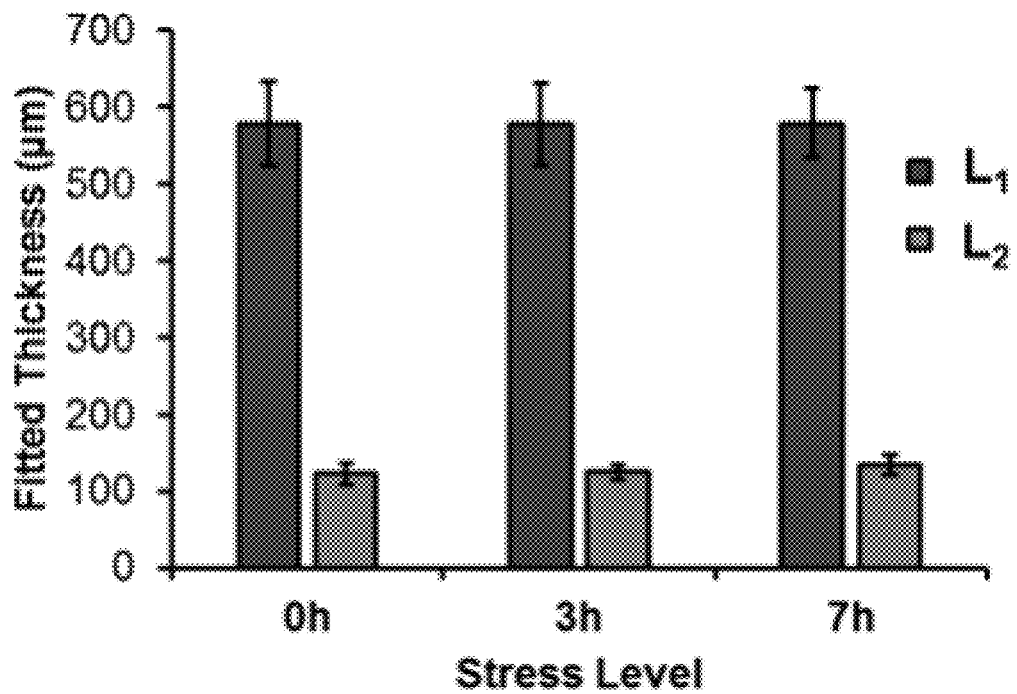

The results shown in FIGS. 9A-9F and FIGS. 10A-10F suggest that the more highly stressed $IgG_1$ samples contain a distribution of oxidized and/or higher order aggregate species that are not accounted for in the initial mathematical model. As a result, the analysis was limited to the low stress protein material (unstressed, 3-hour, and 7-hour). FIGS. 11A, 11B, and 11C provide representative sensor responses to unstressed, 3-hour stressed, and 7-hour stressed $IgG_1$, respectively, using a tunable layer containing 30 μL of 0.2% agarose. $IgG_1$ samples were tested at a nominal concentration of 10 mg/ml, and exact concentrations were measured using UV absorption spectroscopy. Experimental data were fit to the previously developed two-thickness model by specifying the protein concentration and composition (from Table 1), and fitting the values of $L_1$, $L_2$, $\beta$, and $R_{max}$. The model fits are provided in FIGS. 11A-11C along with the experimental data. The fitted $L_1$ and $L_2$ values were similar across all three samples, as shown in FIG. 11D. Moreover, the $L_1$ values were a similar magnitude to what would be expected based on the tunable layer volume and the microwell cross-sectional area. The fitted $\beta$ and $R_{max}$ values were also similar across the three samples and are provided in FIGS. 13-17B.

To extract compositional information from the experimental data, the monomer, LMW, and HMW mole fractions were fit using the $L_1$ and $L_2$ values fit from the unstressed data. The mole fractions were fit across an entire dataset (four replicates), while $\beta$ and $R_{max}$ were fit to each individual replicate. This was done so that the parameters $\beta$ and $R_{max}$ absorb any sensor-to-sensor variability that should not be attributed to sample composition. The resulting fitted mole fractions are provided in FIG. 11E. As expected, the fitted monomer mole fraction is much larger than the mole fractions of LMW and HMW species. Furthermore, the fitting procedure accurately predicts an increase in the concentration of HMW species with stress level. The mole fraction of LMW species remains relatively constant across all three stress levels, which is consistent with the SE-UPLC data presented in Table 1. To evaluate the significance of these results, one-way analysis of variance (ANOVA) was performed across four independent datasets (four replicates per dataset), obtaining an F-ratio of 7.82 and p value of 0.0107.

Figure 11E:
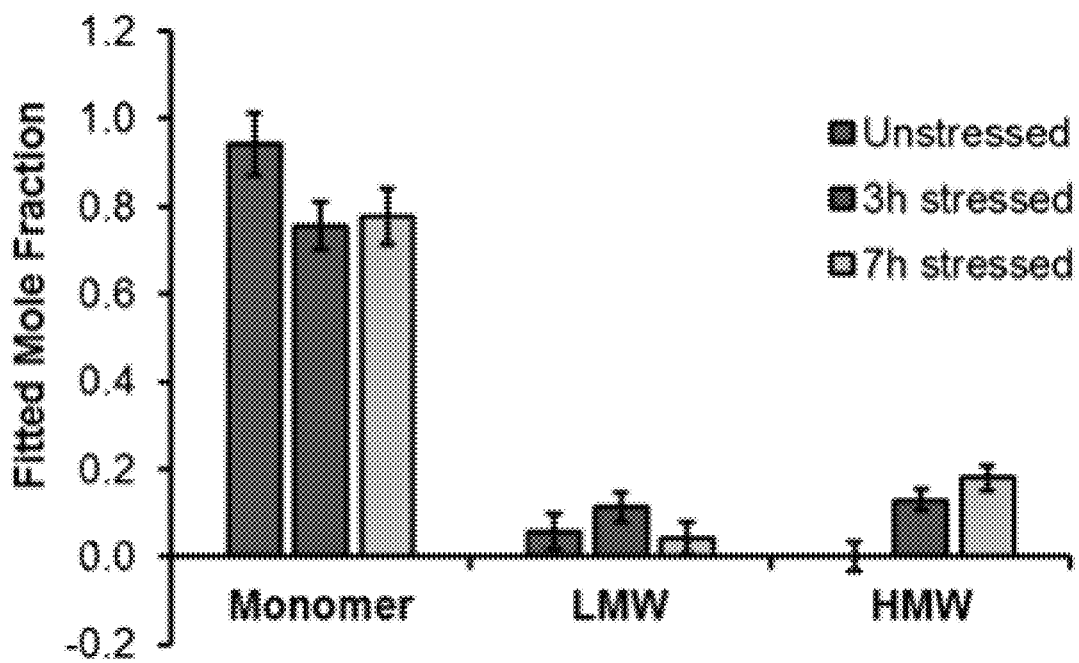
Figure 12A:
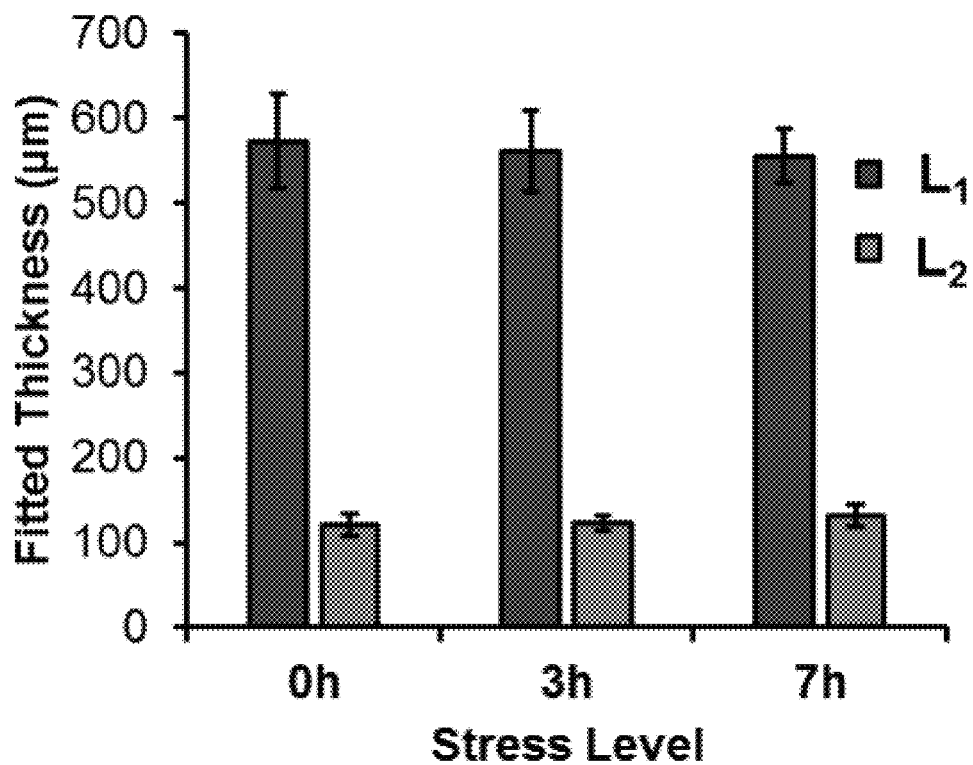
FIG. 12A shows fitted L$_1$ and L$_2$ values for each dataset obtained by specifying the composition from SE-UPLC data, assuming a two-species system of monomer and HMW species. Error bars represent the standard deviation from four replicates.

Extracting the mole fractions of three distinct diffusing species from a single binding curve (or small set of binding curves) results in the relatively large confidence intervals shown in FIG. 11E. While these confidence intervals, and resulting assay resolution, can be improved by collecting more replicates or measuring sensor responses from multiple tunable layer designs, the implementation of a simplified, two-species model in which it was assumed the protein samples were composed of monomeric and HMW species. This simplified model may be more representative of the experimental system given that the LMW species contain $IgG_1$ light chain and cleavage products that don't bind as strongly to protein A. Similarly to FIG. 11D, the $L_1$ and $L_2$ values were fit for each stressed sample based on the compositional information provided by the SE-UPLC data. For this analysis, the monomer mole fraction was assumed to be the sum of the monomer and LMW mole fractions calculated from Table 1. The resulting fitted thicknesses are provided in FIG. 12A and are very similar to those shown in FIG. 11D. Moreover, the coefficients of determination were nearly identical to those obtained from the three species model (>0.999), indicating that the goodness of fit was not reduced by the model simplification.

Figure 12B:
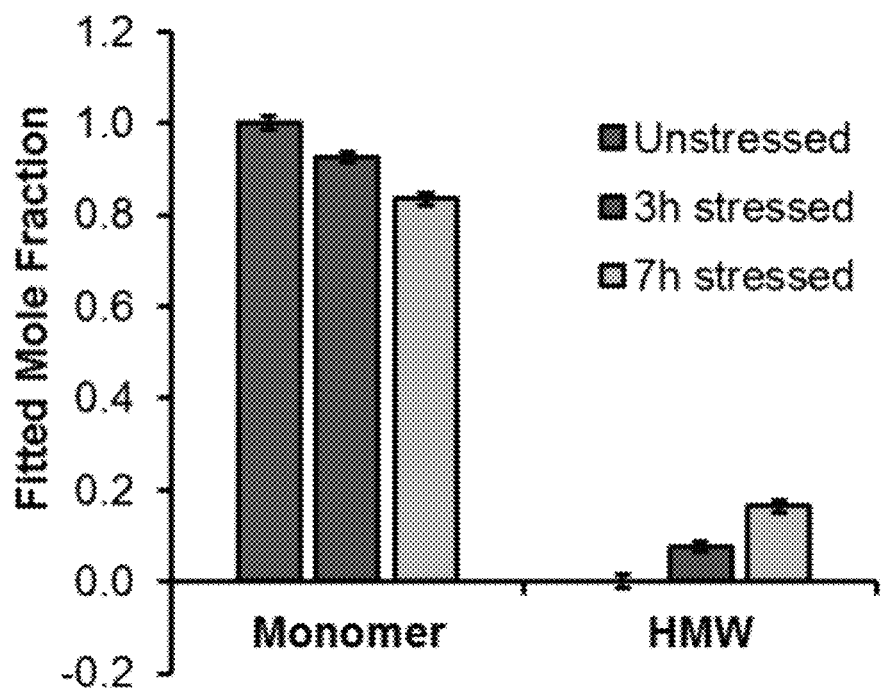
FIG. 12B shows fitted mole fractions of monomer and HMW species using the L$_1$ and L$_2$ values fitted to the unstressed data. Error bars represent the 95% confidence intervals. Parity plot of (FIG. 12C) Monomer and LMW species, and (FIG. 12D) HMW species, based on the SE-UPLC data and fitted values from the 3-species and 2-species models. Error bars represent the 95% confidence intervals.

Using the fitted $L_1$ and $L_2$ values from the unstressed $IgG_1$ material, the mole fractions of monomer and HMW species were fit to all three datasets. As shown in FIG. 12B, the simplified two-species model yields similar results as the three-species model shown in FIG. 11D, with the model accurately fitting an increase in HMW species concentration (and corresponding decrease in monomer concentration) with stress level. Moreover, the 95% confidence intervals of the resulting fits are much smaller than those shown in FIG. 11E. A one-way ANOVA analysis across four independent datasets yielded an F-ratio of 9.2 and p value of 0.0067, confirming that the sensor system can distinguish between the low-stressed samples.

Figure 12C:
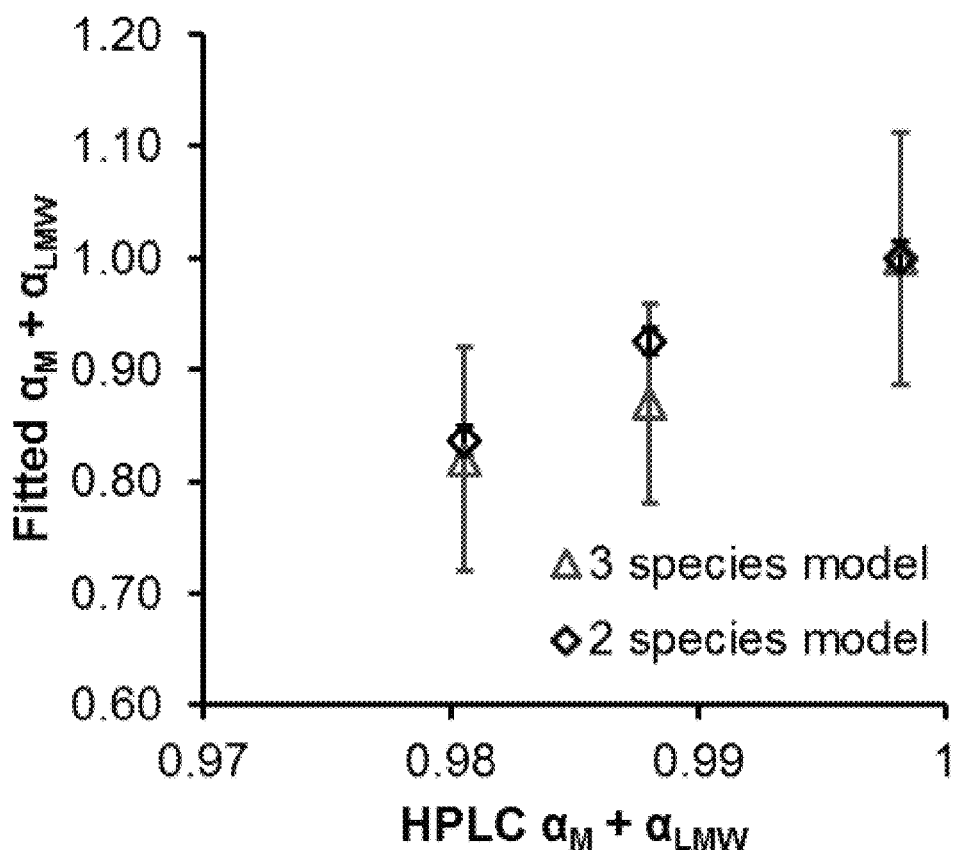
Figure 12D:
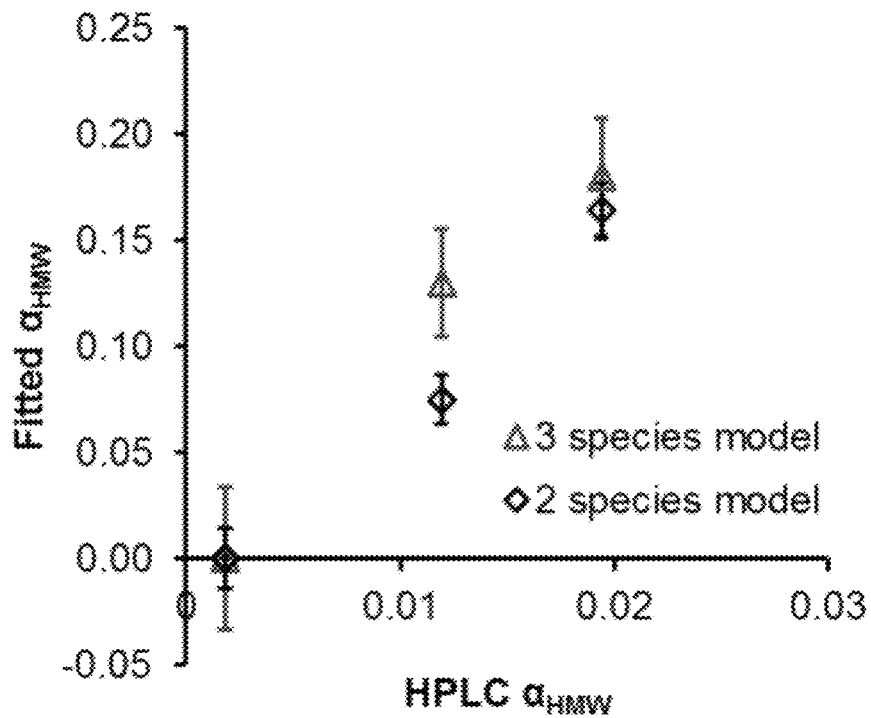
Figure 13:
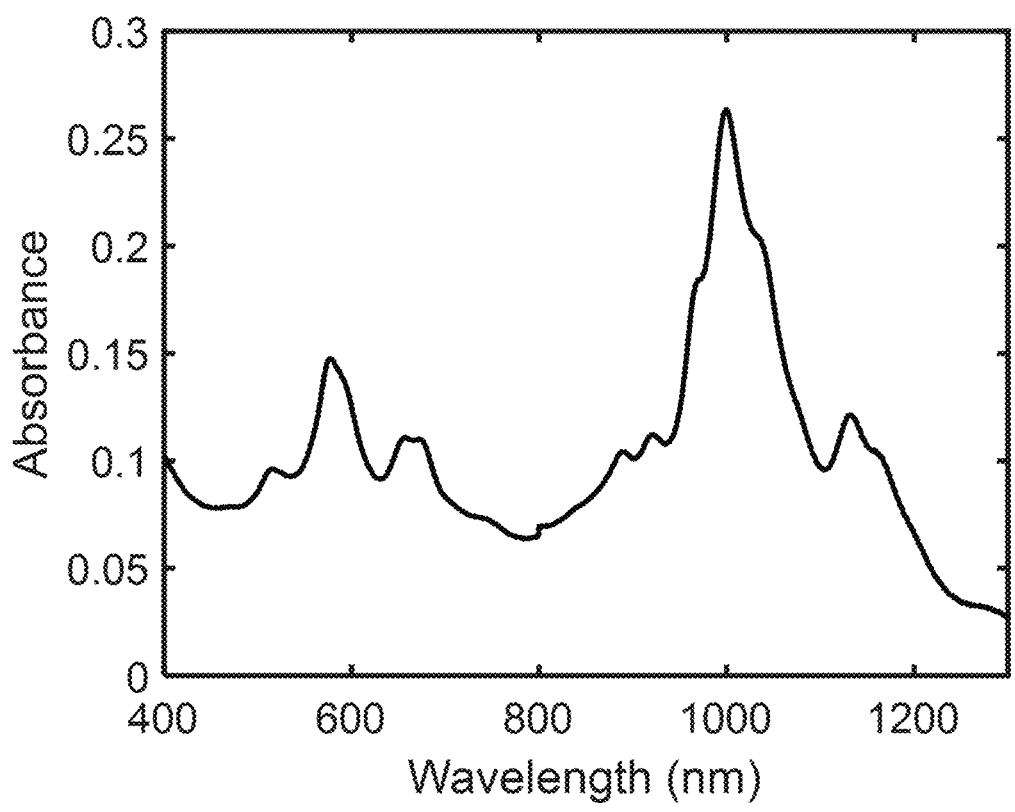
FIG. 13 shows a UV-Vis-nIR absorbance spectrum of chitosan-wrapped purified CoMoCAT SWCNTs used for all experiments.

To compare both models with the SE-UPLC data, parity plots for the fitted mole fractions were constructed. FIG. 12C compares the sum of the monomer and LMW mole fractions, while FIG. 12D compares the HMW mole fractions. In both cases, the models are well correlated with the SE-UPLC data. While an exact 1:1 correlation is not obtained, such a correlation would be highly unlikely given the assumptions of the model and the incomplete particle size distribution information obtained from SE-UPLC. Nevertheless, these results demonstrate the ability of the SWCNT sensor platform to detect levels of protein aggregation as low as one percent.

The current formulation of the mathematical model describing the experimental setup assumes a very simple particle size distribution of monomers, dimers, and ½ fragments. While the 2-species and 3-species models are able to well describe the experimental data, the stressed samples contain a wide distribution of particle shapes and sizes that span a range of diffusion coefficients within the tunable layer. Assuming species diffuse independently, greater elucidation of the particle size distribution is possible by simply incorporating more diffusing species into the mathematical model. However, as demonstrated in FIG. 12C and FIG. 12D, extraction of compositional information with narrow confidence intervals would most likely require sensor multiplexing with more than one distinct tunable layer design. Given that sensor multiplexing can be performed in parallel, greater elucidation of the particle size distribution is possible without an increase in assay time.

The development of a rapid analytical platform for the detection of protein aggregation using hydrogel-encapsulated, nIR-fluorescent SWCNT sensors is described herein. The feasibility of this approach was demonstrated by developing a diffusion model describing the transport of protein species to the sensor. By coupling the diffusion model to a sensor binding model, it is possible to predict the sensor response at a given set of hydrogel properties and protein particle size distributions. Moreover, mathematical modeling was used to map the influence of hydrogel properties on separation performance given the composition of UV-stressed $IgG_1$ samples.

Upon applying the mathematical model to experimental data collected from the stressed $IgG_1$ samples, the data are well fit by a modified two-thickness model which accounts for heterogeneity in the thickness of the tunable hydrogel layer. Using this modified model, the compositions of UV-stressed $IgG_1$ samples were fit to experimental data and correlated with SE-UPLC data. The results demonstrate the ability to detect the presence of high molecular weight protein species at a concentration as low as one percent. This work represents a significant step towards the development and deployment of rapid process analytical technologies for biopharmaceutical characterization.

A number of embodiments of the invention have been described. Nevertheless, it will be understood that various modifications may be made without departing from the spirit and scope of the invention. Accordingly, other embodiments are within the scope of the following claims.

What is claimed is:

1. A sensor comprising:
a housing including a chamber, a light port and a sample contact port, the chamber configured to contain a sensor composition; and
the sensor composition including a nanostructure, the nanostructure supported in a first hydrogel, which is a tunable sensor hydrogel and configured to interact with detect a protein aggregate, the sensor composition being in contact with the light port having a collimator and in direct immersion contact with a sample contact surface adjacent to the sample contact port and a fiber optic coupled to the sensor hydrogel and also coupled to both an excitation laser and a photodetector via a detection fiber configured to detect an emission wavelength from the nanostructure.

2. The sensor of claim 1, further comprising a second hydrogel between the first hydrogel and the sample contact port.

3. The sensor of claim 2, wherein the second hydrogel has a predetermined thickness.

4. The sensor of claim 2, wherein the second hydrogel is the same material as the first hydrogel.

5. The sensor of claim 1, wherein the first hydrogel is a polymeric hydrogel.

6. The sensor of claim 1, wherein the nanostructure includes a linker associated with the nanostructure, wherein the linker is configured to interact with a capture protein.

7. The sensor of claim 6, wherein the linker includes a polymer.

8. The sensor of claim 7, wherein the polymer includes a polypeptide, a polynucleotide or a polysaccharide.

9. The sensor of claim 8, wherein the polysaccharide is chitosan.

10. The sensor of claim 1, wherein the nanostructure is a photoluminescent carbon nanotube.

11. The sensor of claim 1, wherein the light port is configured to attach to a fiber optic.

12. The sensor of claim 11, wherein the fiber optic includes an excitation fiber configured to provide an excitation wavelength to the nanostructure.

13. The sensor of claim 11, wherein the fiber optic includes a detection fiber configured to detect an emission wavelength from the nanostructure.

14. A method for detecting a protein aggregate comprising:
providing the sensor of claim 1;
exposing the sensor to a sample;
monitoring a property of the composition; and
determining the presence of protein aggregate in the sample based on the monitored property.

15. A sensor device including a housing including a chamber, a light port having a collimator and a sample contact port; the chamber configured to contain a sensor composition including a nanostructure supported in a first hydrogel configured to interact with a protein aggregate, a second hydrogel between the first hydrogel and the sample contact port, wherein the second hydrogel and a fiber optic including an excitation fiber configured to provide an excitation wavelength and a detection fiber configured to detect an emission wavelength via a detection fiber configured to detect an emission wavelength from the nanostructure.

* * * * *